US006858585B1

(12) United States Patent
Yanai et al.

(10) Patent No.: US 6,858,585 B1
(45) Date of Patent: Feb. 22, 2005

(54) CYCLIC DEPSIPEPTIDES AND DRUGS CONTAINING THE SAME AS THE ACTIVE INGREDIENT

(75) Inventors: Makoto Yanai, Saitama-ken (JP); Masashi Suzuki, Saitama-ken (JP); Norio Oshida, Saitama-ken (JP); Koji Kawamura, Saitama-ken (JP); Shigeru Hiramoto, Saitama-ken (JP); Orie Yasuda, Saitama-ken (JP); Nobuhiro Kinoshita, Saitama-ken (JP); Akiko Shingai, Saitama-ken (JP); Masako Takasu, Saitama-ken (JP)

(73) Assignee: Nisshin Seifun Group Inc., Tokyo (JP)

( * ) Notice: Subject to any disclaimer, the term of this patent is extended or adjusted under 35 U.S.C. 154(b) by 0 days.

(21) Appl. No.: 09/147,434

(22) PCT Filed: Jun. 25, 1997

(86) PCT No.: PCT/JP97/02194

§ 371 (c)(1),
(2), (4) Date: Oct. 21, 1999

(87) PCT Pub. No.: WO97/49724

PCT Pub. Date: Dec. 31, 1997

(30) Foreign Application Priority Data

Jun. 25, 1996 (JP) ............................................. 8-164317
Sep. 24, 1996 (JP) ............................................. 8-271321

(51) Int. Cl.$^7$ ........................... A61K 38/15; C07K 7/00
(52) U.S. Cl. ............................. 514/11; 514/9; 530/317; 530/323
(58) Field of Search ....................... 514/9, 11; 530/317, 530/323

(56) References Cited

U.S. PATENT DOCUMENTS 5,801,143 A   9/1998   Hiramoto et al.
6,316,406 B1 * 11/2001   Yanai et al. ................... 514/11

FOREIGN PATENT DOCUMENTS

JP      7-291993 A      11/1995
WO      WO 95/32990 A1  12/1995

OTHER PUBLICATIONS (cont. X) Oct. 2002. Abstract Only.*
Okamoto et al. 'Treatment of Vacular Dementia', Ann. NY Acad. Sci. p 507–512. 2002.*
Pinderhuges et al. Evidence Based Approach to Management of Fever in Patients with End Stage Dementia. Journal of Palliative Medicine, Jun. 2003, vol. 6, Iss. 3, p351. Abstract Only.*
Patel Shirish V. Pharmacotherapy of Ognitive Impariment in Alzheimer's Disease: A Review J. of geriatric Physchiatry and Neurology, vol. 8, pp. 81–95. Apr. 1995.*
Fukuyama et al. 'Age–dependent decline in the apolipoprotein E level in cerebrospinal fluid from control subjects and its increase in cerebrospinal fluid from patients with Alzheimer's disease' European Neurology, vol. 43, 3, p. 161–169. Apr. 2000.*
File Medline on STN. An No. 97230053. Urabe et al. 'Effects of Estrogen Replacement Therapy on Hepatic Triglyceride Lipase, Lipoprotein Lipase and Lipids Including Apolipoprotein e In Climacteric and Elderly Women.' Endocrinology Journal, vol. 43, No. (V con.t)—6, pp. 737–742. Dec. 1996 Abstract Only.*
File Medline on STN. An No. 2002690364 Auld et al. 'Alzheimer's Disease and the Basal Forebrain Cholinergic System: Relations to Beta–Amyloid Peptides, Cognition, and Treatment Strategies.' Progress in Neurobiology, vol. 68, No. 3, p. 209–245.*
Jacqueline, A, et al. Halobacillin: A Cytotoxic Cyclic Acylpeptide of the Iturin Class Produced by a Marine Bacillus. Tetrahedron Letters, 1994, vol. 35, No. 31, (pp. 5571–5574).
Harrigan, G.G. et al., Kailuins A–D, New Cyclic Acyldepsipeptides from Cultures of a Marine–Derived Bacterium. Tetrahedron, Feb. 1997, vol. 53, No. 5 (pp. 1577–1582).
Proc. Natl. Acad. Sci. USA, "Expression of apolipoprotein E during nerve degeneration and regeneration", Michael J. Ignatius, et al. vol. 83, (pp. 1125–1129).

* cited by examiner

Primary Examiner—Brenda Brumback
Assistant Examiner—Anish Gupta
(74) Attorney, Agent, or Firm—Oblon, Spivak, McClelland, Maier & Neustadt, P.C.

(57) ABSTRACT

Cyclic depsipeptides represented by the formula $$\text{(structure with } O, A-B-W, (D)_m, Z-F-(E)_n, R \text{)} \tag{1}$$

wherein:

R is a straight or branched alkyl group of 5–20 carbon atoms or a straight or branched alkoxymethyl group of 5–15-carbon atoms; A, B, D, E and F independently each other are alanine, valine, leucine, isoleucine, phenylalanine, etc.; W and Z independently each other are aspartic acid, asparagine, glutamic acid or glutamine; and m and n independently each other is 0 or 1, or pharmacologically acceptable salts thereof. The present compounds are prepared according to a method conventionally used in peptide synthesis. The present compounds are useful as an agent for promoting the production of apolipoprotein E, a therapeutic agent for neurologic damages, a therapeutic agent for dementia, an agent for inhibiting the production of apolipoprotein B, an agent for promoting the production of apolipoprotein A1 or a therapeutic agent for hyperlipemia.

14 Claims, No Drawings

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (2)..(2)
<223> OTHER INFORMATION: OtBuAsp
<221> NAME/KEY: MOD_RES
<222> LOCATION: (4)..(4)
<223> OTHER INFORMATION: CH3(CH2)10CH(OIle)ch2COOBzl

<400> SEQUENCE: 1

Val Asp Leu Ile
1

<210> SEQ ID NO 2
<211> LENGTH: 5
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (3)..(3)
<223> OTHER INFORMATION: OtBuAsp
```

```
<221> NAME/KEY: MOD_RES
<222> LOCATION: (5)..(5)
<223> OTHER INFORMATION: CH3(CH2)10CH(OIle)CH2COOBzl

<400> SEQUENCE: 2

Leu Val Asp Leu Ile
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (4)..(4)
<223> OTHER INFORMATION: OtBuAsp
<221> NAME/KEY: MOD_RES
<222> LOCATION: (6)..(6)
<223> OTHER INFORMATION: CH3(CH2)10CH(OIle)CH2COOBzl

<400> SEQUENCE: 3

Leu Leu Val Asp Leu Ile
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (1)..(1)
<223> OTHER INFORMATION: MbhGln
<221> NAME/KEY: MOD_RES
<222> LOCATION: (5)..(5)
<223> OTHER INFORMATION: OtBuAsp
<221> NAME/KEY: MOD_RES
<222> LOCATION: (7)..(7)
<223> OTHER INFORMATION: CH3(CH2)10CH(OIle)CH2COOBzl

<400> SEQUENCE: 4

Gln Leu Leu Val Asp Leu Ile
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (1)..(1)
<223> OTHER INFORMATION: MbhGln
<221> NAME/KEY: MOD_RES
<222> LOCATION: (5)..(5)
<223> OTHER INFORMATION: OtBuAsp
<221> NAME/KEY: MOD_RES
<222> LOCATION: (7)..(7)
<223> OTHER INFORMATION: CH3(CH2)10CH(OIle)CH2COOBzl

<400> SEQUENCE: 5

Gln Leu Leu Val Asp Leu Ile
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide
```

```
<221> NAME/KEY: MOD_RES
<222> LOCATION: (1)..(1)
<223> OTHER INFORMATION: MbhGln
<221> NAME/KEY: MOD_RES
<222> LOCATION: (5)..(5)
<223> OTHER INFORMATION: OtBuAsp
<221> NAME/KEY: MOD_RES
<222> LOCATION: (7)..(7)
<223> OTHER INFORMATION: CH3(CH2)10CH(OILE)CH2CO linkage to residue 1

<400> SEQUENCE: 6

Gln Leu Leu Val Asp Leu Ile
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (7)..(7)
<223> OTHER INFORMATION: CH3(CH2)10CH(OIle)CH2CO linkage to residue 1

<400> SEQUENCE: 7

Gln Leu Leu Val Asp Leu Ile
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (6)..(6)
<223> OTHER INFORMATION: DLeu
<221> NAME/KEY: misc_feature
<222> LOCATION: (7)..(7)
<223> OTHER INFORMATION: Xaa can be Ala, Val, Leu, Iso, Ser, Thr, Lys,
      hydroxylysine, Arg, Cys, Met, Phe, Tyr, Trp, His, Pro, 4-
      hydroxyproline, piperizine- 4-carboxylic acid
<221> NAME/KEY: misc_feature
<222> LOCATION: (7)..(7)
<223> OTHER INFORMATION: Xaa can be homoproline, oxtahydroindole-2
      carboxylic acid, noraline, norleucine, alpha-t-butylglycine,
      cyclohexylglycine, azetidine -2-carboxylic acid, 3-(3-pyridyl)
      alanine
<221> NAME/KEY: misc_feature
<222> LOCATION: (7)..(7)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine, alpha-methylalanine, 2-aminobutanoic acid; or
      an N-(C1-C4)alkyl derivative of any of the above amino acid
      residues

<400> SEQUENCE: 8

Gln Leu Leu Val Asp Leu Xaa Ala
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
      hydroxylysine, Arg, Cys, Met, Phe, Tyr, Trp, His, Pro, 4-
      hydroxyproline, piperizine- 4-carboxylic acid
<221> NAME/KEY: misc_feature
<222> LOCATION: (3)..(3)
```

```
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (3)..(3)
<223> OTHER INFORMATION: Xaa can be (3-N-methyl)piperizylalanine, 3-(2-
      naphthyl)alanine, beta-cyclohexylalanine, beta-t-butylalanine, 9-
      antracenylalanine, alpha-methylalanine, 2-aminobutanoic acid; or
      an N-(C1-C4)alkyl derivative of any of the above amino acid
      residues
<221> NAME/KEY: misc_feature
<222> LOCATION: (8)..(8)
<223> OTHER INFORMATION: Xaa can be Ala, Val, Leu, Iso, Ser, Thr, Lys,
      hydroxylysine, Arg,Cys, Met, Phe, Tyr, Trp, His, Pro, 4-
      hydroxyproline, piperizine- 4-carboxylic acid
<221> NAME/KEY: misc_feature
<222> LOCATION: (8)..(8)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (8)..(8)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine, alpha-methylalanine, 2-aminobutanoic acid; or
      an N-(C1-C4)alkyl derivative of any of the above amino acid
      residues
<221> NAME/KEY: MOD_RES
<222> LOCATION: (9)..(9)
<223> OTHER INFORMATION: R(OAla)CH2CO linkage to residue 1

<400> SEQUENCE: 9

Gln Leu Xaa Leu Val Asp Leu Xaa Ala
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
      hydroxylysine, Arg, Cys, Met, Phe, Tyr, Trp, His, Pro, 4-
      hydroxyproline, piperizine-4-carboxylic acid
<221> NAME/KEY: misc_feature
<222> LOCATION: (3)..(3)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (3)..(3)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine, alpha-methylalanine, 2-aminobutanoic acid; or
      an N-(C1-C4)alkyl derivative of any of the above amino acid
      residues
<221> NAME/KEY: misc_feature
<222> LOCATION: (8)..(8)
<223> OTHER INFORMATION: Xaa can be Ala, Val, Leu, Iso, Ser, Thr, Lys,
      hydroxylysine, Arg, Cys, Met, Phe, Tyr, Trp, His, Pro, 4-
      hydroxyproline, piperizine- 4-carboxylic acid
<221> NAME/KEY: misc_feature
<222> LOCATION: (8)..(8)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (8)..(8)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine, alpha-methylalanine, 2-aminobutanoic acid; or
```

```
        an N-(C1-C4)alkyl derivative of any of the above amino acid
        residues
<221> NAME/KEY: MOD_RES
<222> LOCATION: (9)..(9)
<223> OTHER INFORMATION: R(OIle)Ch2CO linkage to residue 1

<400> SEQUENCE: 10

Gln Leu Xaa Leu Val Asp Ala Xaa Ile
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
        hydroxylysine, Arg,Cys, Met, Phe, Tyr, Trp, His, Pro, 4-
        hydroxyproline, piperizine- 4-carboxylic acid
<221> NAME/KEY: misc_feature
<222> LOCATION: (3)..(3)
<223> OTHER INFORMATION: Xaa can be homoproline, oxtahydroindole-2
        carboxylic acid, noraline, norleucine, alpha-t-butylglycine,
        cyclohexylglycine, azetidine-2-carboxylic acid, 3-(3-pyridyl)
        alanine
<221> NAME/KEY: misc_feature
<222> LOCATION: (3)..(3)
<223> OTHER INFORMATION: Xaa can be (3-N-methyl)piperizylalanine, 3-
        (2-naphthyl)alanine, beta-cyclohexylalanine, beta-t-butylalanine,
        9-antracenylalanine, alpha-methylalanine, 2-aminobutanoic acid; or
        an N-(C1-C4)alkyl derivative of any of the above amino acid
        residues
<221> NAME/KEY: misc_feature
<222> LOCATION: (8)..(8)
<223> OTHER INFORMATION: Xaa can be Ala, Val, Leu, Iso, Ser, Thr, Lys,
        hydroxylysine, Arg,Cys, Met, Phe, Tyr, Trp, His, Pro, 4-
        hydroxyproline, piperizine-4-carboxylic acid
<221> NAME/KEY: misc_feature
<222> LOCATION: (8)..(8)
<223> OTHER INFORMATION: Xaa can be homoproline, oxtahydroindole-2
        carboxylic acid, noraline, norleucine, alpha-t-butylglycine,
        cyclohexylglycine, azetidine-2-carboxylic acid, 3-(3-pyridyl)
        alanine
<221> NAME/KEY: misc_feature
<222> LOCATION: (8)..(8)
<223> OTHER INFORMATION: Xaa can be (3-N-methyl)piperizylalanine, 3-
        (2-naphthyl)alanine, beta-cyclohexylalanine, beta-t-butylalanine,
        9-antracenylalanine, alpha-methylalanine, 2-aminobutanoic acid; or
        an N-(C1-C4)alkyl derivative of any of the above amino acid
        residues
<221> NAME/KEY: MOD_RES
<222> LOCATION: (9)..(9)
<223> OTHER INFORMATION: R(OIle)CH2CO linkage to residue 1

<400> SEQUENCE: 11

Gln Leu Xaa Leu Val Asp Leu Xaa Ile
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
        hydroxylysine, Arg,Cys, Met, Phe, Tyr, Trp, His, Pro,
        4-hydroxyproline, piperizine-4-carboxylic acid
<221> NAME/KEY: misc_feature
<222> LOCATION: (3)..(3)
<223> OTHER INFORMATION: Xaa can be homoproline, octahydroindole-2-
        carboxylic acid, norvaline, norleucine, alpha-t-butylglycine,
```

```
       cyclohexylglycine, azetidine-2-carboxylic acid, 3-(3-pyridyl)
       alanine
<221> NAME/KEY: misc_feature
<222> LOCATION: (3)..(3)
<223> OTHER INFORMATION: Xaa can be (3-N-methyl)piperizylalanine, 3-
       (2-naphthyl)alanine, beta-cyclohexylalanine, beta-t-butylalanine,
       9-antracenylalanine, alpha-methylalanine, 2-aminobutanoic acid; or
       an N-(C1-C4)alkyl derivative of any of the above amino acid
       residues
<221> NAME/KEY: misc_feature
<222> LOCATION: (8)..(8)
<223> OTHER INFORMATION: Xaa can be Ala, Val, Leu, Iso, Ser, Thr, Lys,
       hydroxylysine, Arg, Cys, Met, Phe, Tyr, Trp, His, Pro,
       4-hydroxyproline, piperizine-4-carboxylic acid
<221> NAME/KEY: misc_feature
<222> LOCATION: (8)..(8)
<223> OTHER INFORMATION: Xaa can be homoproline, oxtahydroindole-2
       carboxylic acid, noraline, norleucine, alpha-t-butylglycine,
       cyclohexylglycine, azetidine-2-carboxylic acid, 3-(3-pyridyl)
       alanine
<221> NAME/KEY: misc_feature
<222> LOCATION: (8)..(8)
<223> OTHER INFORMATION: Xaa can be (3-N-methyl)piperizylalanine, 3-
       (2-naphthyl)alanine, beta-cyclohexylalanine, beta-t-butylalanine,
       9-antracenylalanine, alpha-methylalanine, 2-aminobutanoic acid; or
       an N-(C1-C4)alkyl derivative of any of the above amino acid
       residues
<221> NAME/KEY: MOD_RES
<222> LOCATION: (9)..(9)
<223> OTHER INFORMATION: R(OIle)CH2CO linkage to residue 1

<400> SEQUENCE: 12

Gln Leu Xaa Ala Val Asp Leu Xaa Ile
1               5

<210> SEQ ID NO 13
<211> LENGTH: 9
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
       hydroxylysine, Arg,Cys, Met, Phe, Tyr, Trp, His, Pro,
       4-hydroxyproline, piperizine-4-carboxylic acid
<221> NAME/KEY: misc_feature
<222> LOCATION: (3)..(3)
<223> OTHER INFORMATION: Xaa can be homoproline, octahydroindole-
       2-carboxylic acid, norvaline, norleucine, alpha-t-butylglycine,
       cyclohexylglycine, azetidine-2-carboxylic acid, 3-(3-pyridyl)
       alanine
<221> NAME/KEY: misc_feature
<222> LOCATION: (3)..(3)
<223> OTHER INFORMATION: Xaa can be (3-Neta-cyclohexylalanine, beta-t-
       butylalanine, 9-antracenylalanine,alpha-methylalanine,
       2-aminobutanoic acid; or an N-(C1-C4)alkyl derivative of any of
       the above amino acid residues
<221> NAME/KEY: misc_feature
<222> LOCATION: (8)..(8)
<223> OTHER INFORMATION: Xaa can be Ala, Val, Leu, Iso, Ser, Thr, Lys,
       hydroxylysine, Arg, Cys, Met, Phe, Tyr, Trp, His, Pro,
       4-hydroxyproline, piperizine-4-carboxylic acid
<221> NAME/KEY: misc_feature
<222> LOCATION: (8)..(8)
<223> OTHER INFORMATION: Xaa can be homoproline, oxtahydroindole-2
       carboxylic acid, noraline, norleucine, alpha-t-butylglycine,
       cyclohexylglycine, azetidine-2-carboxylic acid, 3-(3-pyridyl)
       alanine
<221> NAME/KEY: misc_feature
<222> LOCATION: (8)..(8)
<223> OTHER INFORMATION: Xaa can be (3-N-methyl)piperizylalanine,
       3-(2-naphthyl)alanine, beta-cyclohexylalanine,
       beta-t-butylalanine, 9-antracenylalanine, alpha-methylalanine,
       2-aminobutanoic acid; or an N-(C1-C4)alkyl derivative of any of
       the above amino acid residues
<221> NAME/KEY: MOD_RES
```

```
<222> LOCATION: (9)..(9)
<223> OTHER INFORMATION: R(OIle)CH2CO linkage to residue 1

<400> SEQUENCE: 13

Gln Ala Xaa Leu Val Asp Leu Xaa Ile
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (7)..(7)
<223> OTHER INFORMATION: Xaa can be Ala, Val, Leu, Iso, Ser, Thr, Lys,
      hydroxylysine, Arg, Cys, Met, Phe, Tyr, Trp, His, Pro,
      4-hydroxyproline, piperizine-4-carboxylic acid
<221> NAME/KEY: misc_feature
<222> LOCATION: (7)..(7)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (7)..(7)
<223> OTHER INFORMATION: Xaa can be (3-N-methyl)piperizylalanine,
      3-(2-naphthyl)alanine, beta-cyclohexylalanine,
      beta-t-butylalanine, 9-antracenylalanine, alpha-methylalanine,
      2-aminobutanoic acid; or an N-(C1-C4)alkyl derivative of any of
      the above amino acid residues
<221> NAME/KEY: MOD_RES
<222> LOCATION: (8)..(8)
<223> OTHER INFORMATION: R(OIle)CH2CO linkage to residue 1

<400> SEQUENCE: 14

Gln Leu Leu Val Asp Leu Xaa Ile
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
      hydroxylysine, Arg, Cys, Met, Phe, Tyr, Trp, His, Pro,
      4-hydroxyproline, piperizine-4-carboxylic acid
<221> NAME/KEY: misc_feature
<222> LOCATION: (3)..(3)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (3)..(3)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine, alpha-methylalanine, 2-aminobutanoic acid; or
      an N-(C1-C4)alkyl derivative of any of the above amino acid
      residues
<221> NAME/KEY: MOD_RES
<222> LOCATION: (8)..(8)
<223> OTHER INFORMATION: R(OIle)CH2CO linkage to residue 1

<400> SEQUENCE: 15

Gln Leu Xaa Leu Val Asp Leu Ile
1               5

<210> SEQ ID NO 16
<211> LENGTH: 7
```

```
<212> TYPE: PRT
<213> ORGANISM: Artificial Sequence
<220> FEATURE:
<223> OTHER INFORMATION: synthetic peptide
<221> NAME/KEY: MOD_RES
<222> LOCATION: (7)..(7)
<223> OTHER INFORMATION: R(OIle)CH2CO linkage to residue 1

<400> SEQUENCE: 16

Gln Leu Leu Val Asp Leu Ile
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (3)..(3)
<223> OTHER INFORMATION: Xaa can be Ala, Val, Leu, Iso, Ser, Thr, Lys,
     hydroxylysine, Arg, Cys, Met, Phe, Tyr, Trp, His, Pro,
     4-hydroxyproline, piperizine-4-carboxylic acid
<221> NAME/KEY: misc_feature
<222> LOCATION: (3)..(3)
<223> OTHER INFORMATION: Xaa can be homoproline, oxtahydroindole-2
     carboxylic acid, noraline, norleucine, alpha-t-butylglycine,
     cyclohexylglycine, azetidine-2-carboxylic acid, 3-(3-pyridyl)
     alanine
<221> NAME/KEY: misc_feature
<222> LOCATION: (3)..(3)
<223> OTHER INFORMATION: Xaa can be (3-N-methyl)piperizylalanine, 3-
     (2-naphthyl)alanine, beta-cyclohexylalanine, beta-t-butylalanine,
     9-antracenylalanine,alpha-methylalanine, 2-aminobutanoic acid; or
     an N-(C1-C4)alkyl derivative of any of the above amino acid
     residues
<221> NAME/KEY: misc_feature
<222> LOCATION: (8)..(8)
<223> OTHER INFORMATION: Xaa can be Ala, Val, Leu, Iso, Ser, Thr, Lys,
     hydroxylysine, Arg,Cys, Met, Phe, Tyr, Trp, His, Pro,
     4-hydroxyproline, piperizine-4-carboxylic acid
<221> NAME/KEY: misc_feature
<222> LOCATION: (8)..(8)
<223> OTHER INFORMATION: Xaa can be homoproline, oxtahydroindole-2
     carboxylic acid, noraline, norleucine, alpha-t-butylglycine,
     cyclohexylglycine, azetidine-2-carboxylic acid, 3-(3-pyridyl)
     alanine
<221> NAME/KEY: misc_feature
<222> LOCATION: (8)..(8)
<223> OTHER INFORMATION: Xaa can be (3-N-methyl)piperizylalanine, 3-
     (2-naphthyl)alanine, beta-cyclohexylalanine, beta-t-butylalanine,
     9-antracenylalanine, alpha-methylalanine, 2-aminobutanoic acid; or
     an N-(C1-C4)alkyl derivative of any of the above amino acid
     residues
<221> NAME/KEY: MOD_RES
<222> LOCATION: (9)..(9)
<223> OTHER INFORMATION: R(OIle)CH2CO linkage to residue 1

<400> SEQUENCE: 17

Gln Ala Xaa Ala Val Asp Ala Xaa Ile
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (2)..(2)
<223> OTHER INFORMATION: Xaa can be Ala, Val, Leu, Iso, Ser, Thr, Lys,
     hydroxylysine, Arg, Cys, Met, Phe, Tyr, Trp, His, Pro,
     4-hydroxyproline, piperizine-4-carboxylic acid
<221> NAME/KEY: misc_feature
<222> LOCATION: (2)..(2)
```

```
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (2)..(2)
<223> OTHER INFORMATION: Xaa can be (3-N-methyl)piperizylalanine, 3-
      (2-naphthyl)alanine, beta-cyclohexylalanine, beta-t-butylalanine,
      9-anthracenylalanine, alpha-methylalanine 2-aminobutanoic acid;
      or an N-(C1-C4)alkyl derivative of any of the above amino acid
      residues
<221> NAME/KEY: misc_feature
<222> LOCATION: (7)..(7)
<223> OTHER INFORMATION: Xaa can be Ala, Val, Leu, Iso, Ser, Thr, Lys,
      hydroxylysine, Arg,Cys, Met, Phe, Tyr, Trp, His, Pro,
      4-hydroxyproline, piperizine-4-carboxylic acid
<221> NAME/KEY: misc_feature
<222> LOCATION: (7)..(7)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (7)..(7)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine, alpha-methylalanine, 2-aminobutanoic acid;
      or an N-(C1-C4)alkyl derivative of any of the above amino acid
      residues
<221> NAME/KEY: MOD_RES
<222> LOCATION: (8)..(8)
<223> OTHER INFORMATION: R(OIle)CH2CO linkage to residue 1

<400> SEQUENCE: 18

Gln Xaa Leu Val Asp Leu Xaa Ile
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic peptide
<221> NAME/KEY: misc_feature
<222> LOCATION: (5)..(5)
<223> OTHER INFORMATION: Xaa can be Ala, Val, Leu, Iso, Ser, Thr, Lys,
      hydroxylysine, Arg, Cys, Met, Phe, Tyr, Trp, His, Pro,
      4-hydroxyproline, piperizine-4-carboxylic acid
<221> NAME/KEY: misc_feature
<222> LOCATION: (5)..(5)
<223> OTHER INFORMATION: Xaa can be homoproline, oxtahydroindole-2
      carboxylic acid, noraline, norleucine, alpha-t-butylglycine,
      cyclohexylglycine, azetidine-2-carboxylic acid, 3-(3-pyridyl)
      alanine
<221> NAME/KEY: misc_feature
<222> LOCATION: (5)..(5)
<223> OTHER INFORMATION: Xaa can be (3-N-methyl)piperizylalanine, 3-
      (2-naphthyl)alanine, beta-cyclohexylalanine, beta-t-butylalanine,
      9-antracenylalanine,alpha-methylalanine, 2-aminobutanoic acid; or
      an N-(C1-C4)alkyl derivative of any of the above amino acid
      residues
<221> NAME/KEY: MOD_RES
<222> LOCATION: (6)..(6)
<223> OTHER INFORMATION: R(OIle)CH2CO linkage to residue 1

<400> SEQUENCE: 19

Gln Val Asp Leu Xaa Ile
1               5
```

US 6,858,585 B1

CYCLIC DEPSIPEPTIDES AND DRUGS CONTAINING THE SAME AS THE ACTIVE INGREDIENT

BACKGROUND OF THE INVENTION

1. Field of the Invention

This invention relates to a cyclic depsipeptide and a pharmaceutical preparation containing the same as an active ingredient. The cyclic depsipeptides of the invention have a promoting activity on the production of apolipoprotein E, an inhibitory activity on the production of apolipoprotein B and a promoting activity on the production of apolipoprotein A1. Since apolipoprotein E has a repairing activity for neurological damages, the present cyclic depsipeptides having a promoting activity on the production of apolipoprotein E are useful as a therapeutic agent for neurological damages, especially, dementia. On the other hand, apolipoprotein B is a main apolipoprotein of a low-density lipoprotein cholesterol (LDL cholesterol) known as the "bad" cholesterol and apolipoprotein A1 is a main apolipoprotein of a high-density lipoprotein cholesterol (HDL cholesterol) known as the "good" cholesterol. Thus, the cyclic depsipeptides of the invention having an activity of inhibiting the production of apolipoprotein B and an activity of promoting the production of apolipoprotein A1 are useful as a therapeutic agent for hyperlipemia.

2. Description of the Background

As a therapeutic agent for senile dementia, there have been mainly used activators of cerebral circulation and metabolism, but these drugs have no improving effect on disintegration of the central nervous system which is believed to cause senile dementia. Consequently, they possess no improving effect on dysmnesia and acalculia which are said to be central symptoms of dementia. In view of the above, there has been desired a new therapeutic agent for senile dementia which promotes the repair and growth of nervous systems while inhibiting the disintegration of the central nervous system.

On the other hand, it was reported that apolipoprotein E may be generated at a high level at the sites of nervous systems which were damaged and are being repaired (For example, refer to M. J. Igunatius, et al., Proc. Natl. Acad. Sci. U.S.A., 83, 1125 (1986)), which suggests that apolipoprotein E will play an important role in repairing nervous systems.

SUMMARY OF THE INVENTION

We made our earnest studies in order to provide a drug which promotes the production of apolipoprotein E and has a repairing action on neurological damages. As a result, we have found that a certain cyclic depsipeptide possesses such actions, upon which the present invention has been completed.

DETAILED DESCRIPTION OF THE PREFERRED EMBODIMENTS

The present invention relates to an agent for promoting the production of apolipoprotein E which contains as an active ingredient a cyclic depsipeptide represented by the formula (1):

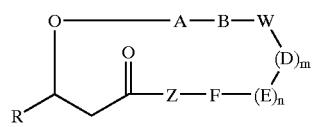

wherein:
R is a straight or branched alkyl group of 5–20 carbon atoms or a straight or branched alkoxymethyl group of 5–15 carbon atoms; A, B, D, E and F independently each other are a residue of an amino acid selected from alanine, valine, leucine, isoleucine, serine, threonine, lysine, hydroxylysine, arginine, cysteine, methionine, phenylalanine, tyrosine, tryptophan, histidine, proline, 4-hydroxyproline, piperizine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperizylalanine, 3-(2-naphthyl)alanine, β-cyclohexylalanine, β-t-butylalanine, 9-anthracenylalanine, α-methylalanine and 2-aminobutanoic acid or an N—($C_1$–$C_4$) alkyl derivative of said amino acid residue; W and Z independently each other are a residue of an amino acid selected from aspartic acid, asparagine, glutamic acid and glutamine; and m and n independently each other is 0 or 1; and wherein a free amino group, a free carboxyl group or a free ω-carbamido group of said amino acid residue may be protected by a protecting group commonly used in peptide chemistry and, when said amino acid residue in the above A, B, D, E, F, W and Z is a residue of lysine, hydroxylysine, glutamic acid or aspartic acid, the amino group or carboxyl group capable of being bound to an adjacent amino acid by peptide linkage may be located at either the α-position or the ω-position) or a pharmacologically acceptable salt thereof.

The invention also relates to a method for promoting the production of apolipoprotein E which comprises administering a cyclic depsipeptide represented by the above formula (1) or a pharmacologically acceptable salt thereof.

Further, the invention relates to a therapeutic agent for neurologic damages or an antidementia agent which comprises as an active ingredient a cyclic depsipeptide represented by the above formula (1) or a pharmacologically acceptable salt thereof.

The invention also relates to a method for the treatment of neurologic damages or dementia which comprises administering a cyclic depsipeptide represented by the above formula (1) or a pharmacologically acceptable salt thereof.

Moreover, the invention relates to a cyclic depsipeptide represented by the following formula (1'):

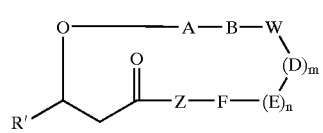

(wherein A, B, D, E, F, W, Z, m and n are as defined above, and R' has the same meanings as the above R; provided that there are excluded the cases wherein m and n are 1, A is isoleucine, B is leucine, W is aspartic acid, D is valine, E is leucine, F is leucine, Z is glutamic acid or glutamine, R' is a group of the formula $R_1$—$(CH_2)_p$— (wherein $R_1$ is methyl, isopropyl, sec-butyl or isobutyl and p is an integer of 5–15)) or a pharmaceutically acceptable salt thereof, and an inhibitory agent on the production of apolipoprotein B and a promoting agent for the production of apolipoprotein A1 or an antihyperlipemic agent.

The invention is also concerned with a method for inhibiting the production of apolipoprotein B, a method for promoting the production of apolipoprotein A1 and a method for treating hyperlipemia.

The aforementioned amino acids, of which the cyclic depsipeptides having the formula (1) of this invention are composed, may be any of L-isomer and D-isomer.

In the above formula (1), it is preferable that A is Ile or Ala, B is Leu, Ala, t-BuAla, Val or Phe, D is Val or Ala, E is Leu, Ala, t-BuAla, Val or Phe, F is Leu, Ala, t-BuAla, Val or Phe, W is Asp or Glu, Z is Gln or Asn, and m and n are 1, and R is a straight alkyl or alkoxymethyl group of 6–12 carbon atoms. The amino acids for A, D, F, W and Z may be preferably in the form of L-isomer, while the amino acids for B and E may be preferably in the form of D-isomer. In particular, it is preferable that A is Ile or Ala, B is D-Leu, D-Ala, D-t-BuAla, D-Val or D-Phe, D is Val or Ala, E is D-Leu, D-Ala, D-t-BuAla, D-Val or D-Phe, F is Leu, Ala, t-BuAla, Val or Phe, W is Asp or Glu and Z is Gln or Asn.

Preferable examples of the compounds of the formula (1) may include the cyclic depsipeptides represented by the following formulae or pharmacologically acceptable salts thereof (SEQ ID NOS: 8–19):

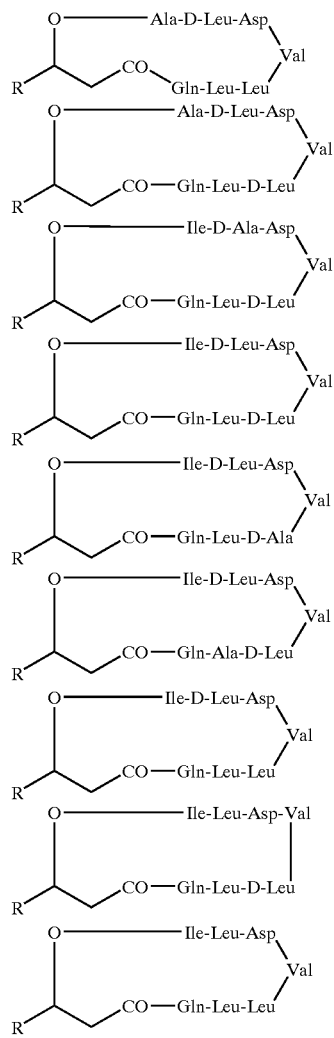

-continued

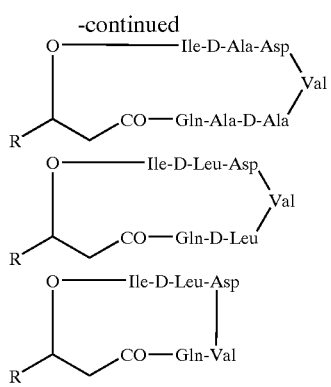

In the above formulae, R is as defined above.

As preferable examples of the cyclic depsipeptides represented by the formula (1) or (1') according to this invention, there may be mentioned those compounds wherein R is a straight alkyl or alkoxymethyl group of 6–12 carbon atoms, m and n are 0 or 1, and wherein A=Ile, B=Leu, W=Asp, D=Ala, E=Leu, F=Leu and Z=Gln;

A=Ile, B=Ala, W=Asp, D=Val, E=Leu, F=Leu and Z=Gln;

A=Ala, B=Leu, W=Asp, D=Val, E=Leu, F=Leu and Z=Gln;

A=Ile, B=Leu, W=Asp, D=Val, E=Ala, F=Leu and Z=Gln;

A=Ile, B=Leu, W=Asp, D=Val, E=Leu, F=Ala and Z=Gln;

or the like.

Of the compounds represented by the formula (1) or (1'), particularly preferable compounds will be listed hereinafter.

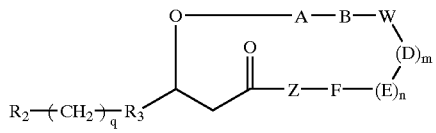

In the above formula, $R_2$ represents a methyl or isopropyl group, $R_3$ represents a direct bond or a group of $-OCH_2-$, and q is an integer of 2–10.

| A | B | W | D | E | F | Z | m | n |
|---|---|---|---|---|---|---|---|---|
| Ile | D-Phe | Glu | Val | D-Leu | Leu | Asn | 1 | 1 |
| Ile | D-Phe | Glu | Val | D-Leu | Leu | Gln | 1 | 1 |
| Ile | D-Phe | Glu | Val | D-Leu | Ala | Asn | 1 | 1 |
| Ile | D-Phe | Glu | Val | D-Leu | Ala | Gln | 1 | 1 |
| Ile | D-Phe | Glu | Val | D-Ala | Leu | Asn | 1 | 1 |
| Ile | D-Phe | Glu | Val | D-Ala | Leu | Gln | 1 | 1 |
| Ile | D-Phe | Glu | Val | D-Ala | Ala | Asn | 1 | 1 |
| Ile | D-Phe | Glu | Val | D-Ala | Ala | Gln | 1 | 1 |
| Ile | D-Phe | Glu | Val | D-Val | Leu | Asn | 1 | 1 |
| Ile | D-Phe | Glu | Val | D-Val | Leu | Gln | 1 | 1 |
| Ile | D-Phe | Glu | Val | D-Val | Ala | Asn | 1 | 1 |
| Ile | D-Phe | Glu | Val | D-Val | Ala | Gln | 1 | 1 |
| Ile | D-Phe | Glu | Val | D-Phe | Leu | Asn | 1 | 1 |
| Ile | D-Phe | Glu | Val | D-Phe | Leu | Gln | 1 | 1 |
| Ile | D-Phe | Glu | Val | D-Phe | Ala | Asn | 1 | 1 |
| Ile | D-Phe | Glu | Val | D-Phe | Ala | Gln | 1 | 1 |
| Ile | D-Phe | Glu | Ala | D-Leu | Leu | Asn | 1 | 1 |
| Ile | D-Phe | Glu | Ala | D-Leu | Leu | Gln | 1 | 1 |
| Ile | D-Phe | Glu | Ala | D-Leu | Ala | Asn | 1 | 1 |

-continued

| A | B | W | D | E | F | Z | m | n |
|---|---|---|---|---|---|---|---|---|
| Ile | D-Phe | Glu | Ala | D-Leu | Ala | Gln | 1 | 1 |
| Ile | D-Phe | Glu | Ala | D-Ala | Leu | Gln | 1 | 1 |
| Ile | D-Phe | Glu | Ala | D-Ala | Ala | Asn | 1 | 1 |
| Ile | D-Phe | Glu | Ala | D-Ala | Ala | Gln | 1 | 1 |
| Ile | D-Phe | Glu | Ala | D-Val | Leu | Asn | 1 | 1 |
| Ile | D-Phe | Glu | Ala | D-Val | Leu | Gln | 1 | 1 |
| Ile | D-Phe | Glu | Ala | D-Val | Ala | Asn | 1 | 1 |
| Ile | D-Phe | Glu | Ala | D-Val | Ala | Gln | 1 | 1 |
| Ile | D-Phe | Glu | Ala | D-Phe | Leu | Asn | 1 | 1 |
| Ile | D-Phe | Glu | Ala | D-Phe | Leu | Gln | 1 | 1 |
| Ile | D-Phe | Glu | Ala | D-Phe | Ala | Asn | 1 | 1 |
| Ile | D-Phe | Glu | Ala | D-Phe | Ala | Gln | 1 | 1 |
| Ile | D-Ala | Asp | Val | D-Leu | Leu | Asn | 1 | 1 |
| Ile | D-Ala | Asp | Val | D-Leu | Leu | Gln | 1 | 1 |
| Ile | D-Ala | Asp | Val | D-Leu | Ala | Asn | 1 | 1 |
| Ile | D-Ala | Asp | Val | D-Leu | Ala | Gln | 1 | 1 |
| Ile | D-Ala | Asp | Val | D-Ala | Leu | Asn | 1 | 1 |
| Ile | D-Ala | Asp | Val | D-Ala | Leu | Gln | 1 | 1 |
| Ile | D-Ala | Asp | Val | D-Ala | Ala | Asn | 1 | 1 |
| Ile | D-Ala | Asp | Val | D-Ala | Ala | Gln | 1 | 1 |
| Ile | D-Ala | Asp | Val | D-Val | Leu | Asn | 1 | 1 |
| Ile | D-Ala | Asp | Val | D-Val | Leu | Gln | 1 | 1 |
| Ile | D-Ala | Asp | Val | D-Val | Ala | Asn | 1 | 1 |
| Ile | D-Ala | Asp | Val | D-Val | Ala | Gln | 1 | 1 |
| Ile | D-Ala | Asp | Val | D-Phe | Leu | Asn | 1 | 1 |
| Ile | D-Ala | Asp | Val | D-Phe | Leu | Gln | 1 | 1 |
| Ile | D-Ala | Asp | Val | D-Phe | Ala | Asn | 1 | 1 |
| Ile | D-Ala | Asp | Val | D-Phe | Ala | Gln | 1 | 1 |
| Ile | D-Ala | Asp | Ala | D-Leu | Leu | Asn | 1 | 1 |
| Ile | D-Ala | Asp | Ala | D-Leu | Leu | Gln | 1 | 1 |
| Ile | D-Ala | Asp | Ala | D-Leu | Ala | Asn | 1 | 1 |
| Ile | D-Ala | Asp | Ala | D-Leu | Ala | Gln | 1 | 1 |
| Ile | D-Ala | Asp | Ala | D-Ala | Leu | Asn | 1 | 1 |
| Ile | D-Ala | Asp | Ala | D-Ala | Leu | Gln | 1 | 1 |
| Ile | D-Ala | Asp | Ala | D-Ala | Ala | Asn | 1 | 1 |
| Ile | D-Ala | Asp | Ala | D-Ala | Ala | Gln | 1 | 1 |
| Ile | D-Ala | Asp | Ala | D-Val | Leu | Asn | 1 | 1 |
| Ile | D-Ala | Asp | Ala | D-Val | Leu | Gln | 1 | 1 |
| Ile | D-Ala | Asp | Ala | D-Val | Ala | Asn | 1 | 1 |
| Ile | D-Ala | Asp | Ala | D-Val | Ala | Gln | 1 | 1 |
| Ile | D-Ala | Asp | Ala | D-Phe | Leu | Asn | 1 | 1 |
| Ile | D-Ala | Asp | Ala | D-Phe | Leu | Gln | 1 | 1 |
| Ile | D-Ala | Asp | Ala | D-Phe | Ala | Asn | 1 | 1 |
| Ile | D-Ala | Asp | Ala | D-Phe | Ala | Gln | 1 | 1 |
| Ile | D-Ala | Glu | Val | D-Leu | Leu | Asn | 1 | 1 |
| Ile | D-Ala | Glu | Val | D-Leu | Leu | Gln | 1 | 1 |
| Ile | D-Ala | Glu | Val | D-Leu | Ala | Asn | 1 | 1 |
| Ile | D-Ala | Glu | Val | D-Leu | Ala | Gln | 1 | 1 |
| Ile | D-Ala | Glu | Val | D-Ala | Leu | Asn | 1 | 1 |
| Ile | D-Ala | Glu | Val | D-Ala | Leu | Gln | 1 | 1 |
| Ile | D-Ala | Glu | Val | D-Ala | Ala | Asn | 1 | 1 |
| Ile | D-Ala | Glu | Val | D-Ala | Ala | Gln | 1 | 1 |
| Ile | D-Ala | Glu | Val | D-Val | Leu | Asn | 1 | 1 |
| Ile | D-Ala | Glu | Val | D-Val | Leu | Gln | 1 | 1 |
| Ile | D-Ala | Glu | Val | D-Val | Ala | Asn | 1 | 1 |
| Ile | D-Ala | Glu | Val | D-Val | Ala | Gln | 1 | 1 |
| Ile | D-Ala | Glu | Val | D-Phe | Leu | Asn | 1 | 1 |
| Ile | D-Ala | Glu | Val | D-Phe | Leu | Gln | 1 | 1 |
| Ile | D-Ala | Glu | Val | D-Phe | Ala | Asn | 1 | 1 |
| Ile | D-Ala | Glu | Val | D-Phe | Ala | Gln | 1 | 1 |
| Ile | D-Ala | Glu | Ala | D-Leu | Leu | Asn | 1 | 1 |
| Ile | D-Ala | Glu | Ala | D-Leu | Leu | Gln | 1 | 1 |
| Ile | D-Ala | Glu | Ala | D-Leu | Ala | Asn | 1 | 1 |
| Ile | D-Ala | Glu | Ala | D-Leu | Ala | Gln | 1 | 1 |
| Ile | D-Ala | Glu | Ala | D-Ala | Leu | Asn | 1 | 1 |
| Ile | D-Ala | Glu | Ala | D-Ala | Leu | Gln | 1 | 1 |
| Ile | D-Ala | Glu | Ala | D-Ala | Ala | Asn | 1 | 1 |
| Ile | D-Ala | Glu | Ala | D-Ala | Ala | Gln | 1 | 1 |
| Ile | D-Ala | Glu | Ala | D-Val | Leu | Asn | 1 | 1 |
| Ile | D-Ala | Glu | Ala | D-Val | Leu | Gln | 1 | 1 |
| Ile | D-Ala | Glu | Ala | D-Val | Ala | Asn | 1 | 1 |
| Ile | D-Ala | Glu | Ala | D-Val | Ala | Gln | 1 | 1 |
| Ile | D-Ala | Glu | Ala | D-Phe | Leu | Asn | 1 | 1 |
| Ile | D-Ala | Glu | Ala | D-Phe | Leu | Gln | 1 | 1 |
| Ile | D-Ala | Glu | Ala | D-Phe | Ala | Asn | 1 | 1 |
| Ile | D-Ala | Glu | Ala | D-Phe | Ala | Gln | 1 | 1 |

-continued

| A | B | W | D | E | F | Z | m | n |
|---|---|---|---|---|---|---|---|---|
| Ile | D-Val | Glu | Val | D-Leu | Leu | Asn | 1 | 1 |
| Ile | D-Val | Glu | Val | D-Leu | Leu | Gln | 1 | 1 |
| Ile | D-Val | Glu | Val | D-Leu | Ala | Asn | 1 | 1 |
| Ile | D-Val | Glu | Val | D-Leu | Ala | Gln | 1 | 1 |
| Ile | D-Val | Glu | Val | D-Ala | Leu | Asn | 1 | 1 |
| Ile | D-Val | Glu | Val | D-Ala | Leu | Gln | 1 | 1 |
| Ile | D-Val | Glu | Val | D-Ala | Ala | Asn | 1 | 1 |
| Ile | D-Val | Glu | Val | D-Ala | Ala | Gln | 1 | 1 |
| Ile | D-Val | Glu | Val | D-Val | Leu | Asn | 1 | 1 |
| Ile | D-Val | Glu | Val | D-Val | Leu | Gln | 1 | 1 |
| Ile | D-Val | Glu | Val | D-Val | Ala | Asn | 1 | 1 |
| Ile | D-Val | Glu | Val | D-Val | Ala | Gln | 1 | 1 |
| Ile | D-Val | Glu | Val | D-Phe | Leu | Asn | 1 | 1 |
| Ile | D-Val | Glu | Val | D-Phe | Leu | Gln | 1 | 1 |
| Ile | D-Val | Glu | Val | D-Phe | Ala | Asn | 1 | 1 |
| Ile | D-Val | Glu | Val | D-Phe | Ala | Gln | 1 | 1 |
| Ile | D-Val | Glu | Ala | D-Leu | Leu | Asn | 1 | 1 |
| Ile | D-Val | Glu | Ala | D-Leu | Leu | Gln | 1 | 1 |
| Ile | D-Val | Glu | Ala | D-Leu | Ala | Asn | 1 | 1 |
| Ile | D-Val | Glu | Ala | D-Leu | Ala | Gln | 1 | 1 |
| Ile | D-Val | Glu | Ala | D-Ala | Leu | Asn | 1 | 1 |
| Ile | D-Val | Glu | Ala | D-Ala | Leu | Gln | 1 | 1 |
| Ile | D-Val | Glu | Ala | D-Ala | Ala | Asn | 1 | 1 |
| Ile | D-Val | Glu | Ala | D-Ala | Ala | Gln | 1 | 1 |
| Ile | D-Val | Glu | Ala | D-Val | Leu | Asn | 1 | 1 |
| Ile | D-Val | Glu | Ala | D-Val | Leu | Gln | 1 | 1 |
| Ile | D-Val | Glu | Ala | D-Val | Ala | Asn | 1 | 1 |
| Ile | D-Val | Glu | Ala | D-Val | Ala | Gln | 1 | 1 |
| Ile | D-Val | Glu | Ala | D-Phe | Leu | Asn | 1 | 1 |
| Ile | D-Val | Glu | Ala | D-Phe | Leu | Gln | 1 | 1 |
| Ile | D-Val | Glu | Ala | D-Phe | Ala | Asn | 1 | 1 |
| Ile | D-Val | Glu | Ala | D-Phe | Ala | Gln | 1 | 1 |
| Ile | D-Leu | Glu | Val | D-Leu | Leu | Asn | 1 | 1 |
| Ile | D-Leu | Glu | Val | D-Leu | Leu | Gln | 1 | 1 |
| Ile | D-Leu | Glu | Val | D-Leu | Ala | Asn | 1 | 1 |
| Ile | D-Leu | Glu | Val | D-Leu | Ala | Gln | 1 | 1 |
| Ile | D-Leu | Glu | Val | D-Ala | Leu | Asn | 1 | 1 |
| Ile | D-Leu | Glu | Val | D-Ala | Leu | Gln | 1 | 1 |
| Ile | D-Leu | Glu | Val | D-Ala | Ala | Asn | 1 | 1 |
| Ile | D-Leu | Glu | Val | D-Ala | Ala | Gln | 1 | 1 |
| Ile | D-Leu | Glu | Val | D-Val | Leu | Asn | 1 | 1 |
| Ile | D-Leu | Glu | Val | D-Val | Leu | Gln | 1 | 1 |
| Ile | D-Leu | Glu | Val | D-Val | Ala | Asn | 1 | 1 |
| Ile | D-Leu | Glu | Val | D-Val | Ala | Gln | 1 | 1 |
| Ile | D-Leu | Glu | Val | D-Phe | Leu | Asn | 1 | 1 |
| Ile | D-Leu | Glu | Val | D-Phe | Leu | Gln | 1 | 1 |
| Ile | D-Leu | Glu | Val | D-Phe | Ala | Asn | 1 | 1 |
| Ile | D-Leu | Glu | Val | D-Phe | Ala | Gln | 1 | 1 |
| Ile | D-Leu | Glu | Ala | D-Leu | Leu | Asn | 1 | 1 |
| Ile | D-Leu | Glu | Ala | D-Leu | Leu | Gln | 1 | 1 |
| Ile | D-Leu | Glu | Ala | D-Leu | Ala | Asn | 1 | 1 |
| Ile | D-Leu | Glu | Ala | D-Leu | Ala | Gln | 1 | 1 |
| Ile | D-Leu | Glu | Ala | D-Ala | Leu | Asn | 1 | 1 |
| Ile | D-Val | Glu | Ala | D-Ala | Leu | Gln | 1 | 1 |
| Ile | D-Leu | Glu | Ala | D-Ala | Ala | Asn | 1 | 1 |
| Ile | D-Leu | Glu | Ala | D-Ala | Ala | Gln | 1 | 1 |
| Ile | D-Leu | Glu | Ala | D-Val | Leu | Asn | 1 | 1 |
| Ile | D-Leu | Glu | Ala | D-Val | Leu | Gln | 1 | 1 |
| Ile | D-Leu | Glu | Ala | D-Val | Ala | Asn | 1 | 1 |
| Ile | D-Leu | Glu | Ala | D-Val | Ala | Gln | 1 | 1 |
| Ile | D-Leu | Glu | Ala | D-Phe | Leu | Asn | 1 | 1 |
| Ile | D-Leu | Glu | Ala | D-Phe | Leu | Gln | 1 | 1 |
| Ile | D-Leu | Glu | Ala | D-Phe | Ala | Asn | 1 | 1 |
| Ile | D-Leu | Glu | Ala | D-Phe | Ala | Gln | 1 | 1 |
| Ile | D-Phe | Asp | Val | D-Leu | Leu | Asn | 1 | 1 |
| Ile | D-Phe | Asp | Val | D-Leu | Leu | Gln | 1 | 1 |
| Ile | D-Phe | Asp | Val | D-Leu | Ala | Asn | 1 | 1 |
| Ile | D-Phe | Asp | Val | D-Leu | Ala | Gln | 1 | 1 |
| Ile | D-Phe | Asp | Val | D-Ala | Leu | Asn | 1 | 1 |
| Ile | D-Phe | Asp | Val | D-Ala | Leu | Gln | 1 | 1 |
| Ile | D-Phe | Asp | Val | D-Ala | Ala | Asn | 1 | 1 |
| Ile | D-Phe | Asp | Val | D-Ala | Ala | Gln | 1 | 1 |
| Ile | D-Phe | Asp | Val | D-Val | Leu | Asn | 1 | 1 |
| Ile | D-Phe | Asp | Val | D-Val | Leu | Gln | 1 | 1 |
| Ile | D-Phe | Asp | Val | D-Val | Ala | Asn | 1 | 1 |
| Ile | D-Phe | Asp | Val | D-Val | Ala | Gln | 1 | 1 |
| Ile | D-Phe | Asp | Val | D-Phe | Leu | Asn | 1 | 1 |

-continued

| A | B | W | D | E | F | Z | m | n |
|---|---|---|---|---|---|---|---|---|
| Ile | D-Phe | Asp | Val | D-Phe | Leu | Gln | 1 | 1 |
| Ile | D-Phe | Asp | Val | D-Phe | Ala | Asn | 1 | 1 |
| Ile | D-Phe | Asp | Ala | D-Leu | Leu | Asn | 1 | 1 |
| Ile | D-Phe | Asp | Ala | D-Leu | Leu | Gln | 1 | 1 |
| Ile | D-Phe | Asp | Ala | D-Leu | Ala | Asn | 1 | 1 |
| Ile | D-Phe | Asp | Ala | D-Leu | Ala | Gln | 1 | 1 |
| Ile | D-Phe | Asp | Ala | D-Ala | Leu | Asn | 1 | 1 |
| Ile | D-Phe | Asp | Ala | D-Ala | Leu | Gln | 1 | 1 |
| Ile | D-Phe | Asp | Ala | D-Ala | Ala | Asn | 1 | 1 |
| Ile | D-Phe | Asp | Ala | D-Ala | Ala | Gln | 1 | 1 |
| Ile | D-Phe | Asp | Ala | D-Val | Leu | Asn | 1 | 1 |
| Ile | D-Phe | Asp | Ala | D-Val | Leu | Gln | 1 | 1 |
| Ile | D-Phe | Asp | Ala | D-Val | Ala | Asn | 1 | 1 |
| Ile | D-Phe | Asp | Ala | D-Val | Ala | Gln | 1 | 1 |
| Ile | D-Phe | Asp | Ala | D-Phe | Leu | Asn | 1 | 1 |
| Ile | D-Phe | Asp | Ala | D-Phe | Leu | Gln | 1 | 1 |
| Ile | D-Phe | Asp | Ala | D-Phe | Ala | Asn | 1 | 1 |
| Ile | D-Phe | Asp | Ala | D-Phe | Ala | Gln | 1 | 1 |
| Ile | D-Val | Asp | Val | D-Leu | Leu | Asn | 1 | 1 |
| Ile | D-Val | Asp | Val | D-Leu | Leu | Gln | 1 | 1 |
| Ile | D-Val | Asp | Val | D-Leu | Ala | Asn | 1 | 1 |
| Ile | D-Val | Asp | Val | D-Leu | Ala | Gln | 1 | 1 |
| Ile | D-Val | Asp | Val | D-Ala | Leu | Asn | 1 | 1 |
| Ile | D-Val | Asp | Val | D-Ala | Leu | Gln | 1 | 1 |
| Ile | D-Val | Asp | Val | D-Ala | Ala | Asn | 1 | 1 |
| Ile | D-Val | Asp | Val | D-Ala | Ala | Gln | 1 | 1 |
| Ile | D-Val | Asp | Val | D-Val | Leu | Asn | 1 | 1 |
| Ile | D-Val | Asp | Val | D-Val | Leu | Gln | 1 | 1 |
| Ile | D-Val | Asp | Val | D-Val | Ala | Asn | 1 | 1 |
| Ile | D-Val | Asp | Val | D-Val | Ala | Gln | 1 | 1 |
| Ile | D-Val | Asp | Val | D-Phe | Leu | Asn | 1 | 1 |
| Ile | D-Val | Asp | Val | D-Phe | Leu | Gln | 1 | 1 |
| Ile | D-Val | Asp | Val | D-Phe | Ala | Asn | 1 | 1 |
| Ile | D-Val | Asp | Val | D-Phe | Ala | Gln | 1 | 1 |
| Ile | D-Val | Asp | Ala | D-Leu | Leu | Asn | 1 | 1 |
| Ile | D-Val | Asp | Ala | D-Leu | Leu | Gln | 1 | 1 |
| Ile | D-Val | Asp | Ala | D-Leu | Ala | Asn | 1 | 1 |
| Ile | D-Val | Asp | Ala | D-Leu | Ala | Gln | 1 | 1 |
| Ile | D-Val | Asp | Ala | D-Ala | Leu | Asn | 1 | 1 |
| Ile | D-Val | Asp | Ala | D-Ala | Leu | Gln | 1 | 1 |
| Ile | D-Val | Asp | Ala | D-Ala | Ala | Asn | 1 | 1 |
| Ile | D-Val | Asp | Ala | D-Ala | Ala | Gln | 1 | 1 |
| Ile | D-Val | Asp | Ala | D-Val | Leu | Asn | 1 | 1 |
| Ile | D-Val | Asp | Ala | D-Val | Leu | Gln | 1 | 1 |
| Ile | D-Val | Asp | Ala | D-Val | Ala | Asn | 1 | 1 |
| Ile | D-Val | Asp | Ala | D-Val | Ala | Gln | 1 | 1 |
| Ile | D-Val | Asp | Ala | D-Phe | Leu | Asn | 1 | 1 |
| Ile | D-Val | Asp | Ala | D-Phe | Leu | Gln | 1 | 1 |
| Ile | D-Val | Asp | Ala | D-Phe | Ala | Asn | 1 | 1 |
| Ile | D-Val | Asp | Ala | D-Phe | Ala | Gln | 1 | 1 |
| Ile | D-Leu | Asp | Val | D-Leu | Leu | Asn | 1 | 1 |
| Ile | D-Leu | Asp | Val | D-Leu | Leu | Gln | 1 | 1 |
| Ile | D-Leu | Asp | Val | D-Leu | Ala | Asn | 1 | 1 |
| Ile | D-Leu | Asp | Val | D-Leu | Ala | Gln | 1 | 1 |
| Ile | D-Leu | Asp | Val | D-Ala | Leu | Asn | 1 | 1 |
| Ile | D-Leu | Asp | Val | D-Ala | Leu | Gln | 1 | 1 |
| Ile | D-Leu | Asp | Val | D-Ala | Ala | Asn | 1 | 1 |
| Ile | D-Leu | Asp | Val | D-Ala | Ala | Gln | 1 | 1 |
| Ile | D-Leu | Asp | Val | D-Val | Leu | Asn | 1 | 1 |
| Ile | D-Leu | Asp | Val | D-Val | Leu | Gln | 1 | 1 |
| Ile | D-Leu | Asp | Val | D-Val | Ala | Asn | 1 | 1 |
| Ile | D-Leu | Asp | Val | D-Val | Ala | Gln | 1 | 1 |
| Ile | D-Leu | Asp | Val | D-Phe | Leu | Asn | 1 | 1 |
| Ile | D-Leu | Asp | Val | D-Phe | Leu | Gln | 1 | 1 |
| Ile | D-Leu | Asp | Val | D-Phe | Ala | Asn | 1 | 1 |
| Ile | D-Leu | Asp | Val | D-Phe | Ala | Gln | 1 | 1 |
| Ile | D-Leu | Asp | Ala | D-Leu | Leu | Asn | 1 | 1 |
| Ile | D-Leu | Asp | Ala | D-Leu | Leu | Gln | 1 | 1 |
| Ile | D-Leu | Asp | Ala | D-Leu | Ala | Asn | 1 | 1 |
| Ile | D-Leu | Asp | Ala | D-Leu | Ala | Gln | 1 | 1 |
| Ile | D-Leu | Asp | Ala | D-Ala | Leu | Asn | 1 | 1 |
| Ile | D-Leu | Asp | Ala | D-Ala | Leu | Gln | 1 | 1 |
| Ile | D-Leu | Asp | Ala | D-Ala | Ala | Asn | 1 | 1 |
| Ile | D-Leu | Asp | Ala | D-Ala | Ala | Gln | 1 | 1 |
| Ile | D-Leu | Asp | Ala | D-Val | Leu | Asn | 1 | 1 |
| Ile | D-Leu | Asp | Ala | D-Val | Leu | Gln | 1 | 1 |
| Ile | D-Leu | Asp | Ala | D-Val | Ala | Asn | 1 | 1 |
| Ile | D-Leu | Asp | Ala | D-Val | Ala | Gln | 1 | 1 |
| Ile | D-Leu | Asp | Ala | D-Phe | Leu | Asn | 1 | 1 |
| Ile | D-Leu | Asp | Ala | D-Phe | Leu | Gln | 1 | 1 |
| Ile | D-Leu | Asp | Ala | D-Phe | Ala | Asn | 1 | 1 |
| Ile | D-Leu | Asp | Ala | D-Phe | Ala | Gln | 1 | 1 |
| Ala | D-Val | Glu | Val | D-Leu | Leu | Asn | 1 | 1 |
| Ala | D-Val | Glu | Val | D-Leu | Leu | Gln | 1 | 1 |
| Ala | D-Val | Glu | Val | D-Leu | Ala | Asn | 1 | 1 |
| Ala | D-Val | Glu | Val | D-Leu | Ala | Gln | 1 | 1 |
| Ala | D-Val | Glu | Val | D-Ala | Leu | Asn | 1 | 1 |
| Ala | D-Val | Glu | Val | D-Ala | Leu | Gln | 1 | 1 |
| Ala | D-Val | Glu | Val | D-Ala | Ala | Asn | 1 | 1 |
| Ala | D-Val | Glu | Val | D-Ala | Ala | Gln | 1 | 1 |
| Ala | D-Val | Glu | Val | D-Val | Leu | Asn | 1 | 1 |
| Ala | D-Val | Glu | Val | D-Val | Leu | Gln | 1 | 1 |
| Ala | D-Val | Glu | Val | D-Val | Ala | Asn | 1 | 1 |
| Ala | D-Val | Glu | Val | D-Val | Ala | Gln | 1 | 1 |
| Ala | D-Val | Glu | Val | D-Phe | Leu | Asn | 1 | 1 |
| Ala | D-Val | Glu | Val | D-Phe | Leu | Gln | 1 | 1 |
| Ala | D-Val | Glu | Val | D-Phe | Ala | Asn | 1 | 1 |
| Ala | D-Val | Glu | Val | D-Phe | Ala | Gln | 1 | 1 |
| Ala | D-Val | Glu | Ala | D-Leu | Leu | Asn | 1 | 1 |
| Ala | D-Val | Glu | Ala | D-Leu | Leu | Gln | 1 | 1 |
| Ala | D-Val | Glu | Ala | D-Leu | Ala | Asn | 1 | 1 |
| Ala | D-Val | Glu | Ala | D-Leu | Ala | Gln | 1 | 1 |
| Ala | D-Val | Glu | Ala | D-Ala | Leu | Asn | 1 | 1 |
| Ala | D-Val | Glu | Ala | D-Ala | Leu | Gln | 1 | 1 |
| Ala | D-Val | Glu | Ala | D-Ala | Ala | Asn | 1 | 1 |
| Ala | D-Val | Glu | Ala | D-Ala | Ala | Gln | 1 | 1 |
| Ala | D-Val | Glu | Ala | D-Val | Leu | Asn | 1 | 1 |
| Ala | D-Val | Glu | Ala | D-Val | Leu | Gln | 1 | 1 |
| Ala | D-Val | Glu | Ala | D-Val | Ala | Asn | 1 | 1 |
| Ala | D-Val | Glu | Ala | D-Val | Ala | Gln | 1 | 1 |
| Ala | D-Val | Glu | Ala | D-Phe | Leu | Asn | 1 | 1 |
| Ala | D-Val | Glu | Ala | D-Phe | Leu | Gln | 1 | 1 |
| Ala | D-Val | Glu | Ala | D-Phe | Ala | Asn | 1 | 1 |
| Ala | D-Val | Glu | Ala | D-Phe | Ala | Gln | 1 | 1 |
| Ala | D-Leu | Glu | Val | D-Leu | Leu | Asn | 1 | 1 |
| Ala | D-Leu | Glu | Val | D-Leu | Leu | Gln | 1 | 1 |
| Ala | D-Leu | Glu | Val | D-Leu | Ala | Asn | 1 | 1 |
| Ala | D-Leu | Glu | Val | D-Leu | Ala | Gln | 1 | 1 |
| Ala | D-Leu | Glu | Val | D-Ala | Leu | Asn | 1 | 1 |
| Ala | D-Leu | Glu | Val | D-Ala | Leu | Gln | 1 | 1 |
| Ala | D-Leu | Glu | Val | D-Ala | Ala | Asn | 1 | 1 |
| Ala | D-Leu | Glu | Val | D-Ala | Ala | Gln | 1 | 1 |
| Ala | D-Leu | Glu | Val | D-Val | Leu | Asn | 1 | 1 |
| Ala | D-Leu | Glu | Val | D-Val | Leu | Gln | 1 | 1 |
| Ala | D-Leu | Glu | Val | D-Val | Ala | Asn | 1 | 1 |
| Ala | D-Leu | Glu | Val | D-Val | Ala | Gln | 1 | 1 |
| Ala | D-Leu | Glu | Val | D-Phe | Leu | Asn | 1 | 1 |
| Ala | D-Leu | Glu | Val | D-Phe | Leu | Gln | 1 | 1 |
| Ala | D-Leu | Glu | Val | D-Phe | Ala | Asn | 1 | 1 |
| Ala | D-Leu | Glu | Val | D-Phe | Ala | Gln | 1 | 1 |
| Ala | D-Leu | Glu | Ala | D-Leu | Leu | Asn | 1 | 1 |
| Ala | D-Leu | Glu | Ala | D-Leu | Leu | Gln | 1 | 1 |
| Ala | D-Leu | Glu | Ala | D-Leu | Ala | Asn | 1 | 1 |
| Ala | D-Leu | Glu | Ala | D-Leu | Ala | Gln | 1 | 1 |
| Ala | D-Leu | Glu | Ala | D-Ala | Leu | Asn | 1 | 1 |
| Ala | D-Leu | Glu | Ala | D-Ala | Leu | Gln | 1 | 1 |
| Ala | D-Leu | Glu | Ala | D-Ala | Ala | Asn | 1 | 1 |
| Ala | D-Leu | Glu | Ala | D-Ala | Ala | Gln | 1 | 1 |
| Ala | D-Leu | Glu | Ala | D-Val | Leu | Asn | 1 | 1 |
| Ala | D-Leu | Glu | Ala | D-Val | Leu | Gln | 1 | 1 |
| Ala | D-Leu | Glu | Ala | D-Val | Ala | Asn | 1 | 1 |
| Ala | D-Leu | Glu | Ala | D-Val | Ala | Gln | 1 | 1 |
| Ala | D-Leu | Glu | Ala | D-Phe | Leu | Asn | 1 | 1 |
| Ala | D-Leu | Glu | Ala | D-Phe | Leu | Gln | 1 | 1 |
| Ala | D-Leu | Glu | Ala | D-Phe | Ala | Asn | 1 | 1 |
| Ala | D-Leu | Glu | Ala | D-Phe | Ala | Gln | 1 | 1 |
| Ala | D-Ala | Glu | Val | D-Leu | Leu | Asn | 1 | 1 |
| Ala | D-Ala | Glu | Val | D-Leu | Leu | Gln | 1 | 1 |
| Ala | D-Ala | Glu | Val | D-Leu | Ala | Asn | 1 | 1 |
| Ala | D-Ala | Glu | Val | D-Leu | Ala | Gln | 1 | 1 |
| Ala | D-Ala | Glu | Val | D-Ala | Leu | Asn | 1 | 1 |
| Ala | D-Ala | Glu | Val | D-Ala | Leu | Gln | 1 | 1 |
| Ala | D-Ala | Glu | Val | D-Ala | Ala | Asn | 1 | 1 |

-continued

| A | B | W | D | E | F | Z | m | n |
|---|---|---|---|---|---|---|---|---|
| Ala | D-Ala | Glu | Val | D-Ala | Ala | Gln | 1 | 1 |
| Ala | D-Ala | Glu | Val | D-Val | Leu | Asn | 1 | 1 |
| Ala | D-Ala | Glu | Val | D-Val | Leu | Gln | 1 | 1 |
| Ala | D-Ala | Glu | Val | D-Val | Ala | Asn | 1 | 1 |
| Ala | D-Ala | Glu | Val | D-Val | Ala | Gln | 1 | 1 |
| Ala | D-Ala | Glu | Val | D-Phe | Leu | Asn | 1 | 1 |
| Ala | D-Ala | Glu | Val | D-Phe | Leu | Gln | 1 | 1 |
| Ala | D-Ala | Glu | Val | D-Phe | Ala | Asn | 1 | 1 |
| Ala | D-Ala | Glu | Val | D-Phe | Ala | Gln | 1 | 1 |
| Ala | D-Ala | Glu | Ala | D-Leu | Leu | Asn | 1 | 1 |
| Ala | D-Ala | Glu | Ala | D-Leu | Leu | Gln | 1 | 1 |
| Ala | D-Ala | Glu | Ala | D-Leu | Ala | Asn | 1 | 1 |
| Ala | D-Ala | Glu | Ala | D-Leu | Ala | Gln | 1 | 1 |
| Ala | D-Ala | Glu | Ala | D-Ala | Leu | Asn | 1 | 1 |
| Ala | D-Ala | Glu | Ala | D-Ala | Leu | Gln | 1 | 1 |
| Ala | D-Ala | Glu | Ala | D-Ala | Ala | Asn | 1 | 1 |
| Ala | D-Ala | Glu | Ala | D-Ala | Ala | Gln | 1 | 1 |
| Ala | D-Ala | Glu | Ala | D-Val | Leu | Asn | 1 | 1 |
| Ala | D-Ala | Glu | Ala | D-Val | Leu | Gln | 1 | 1 |
| Ala | D-Ala | Glu | Ala | D-Val | Ala | Asn | 1 | 1 |
| Ala | D-Ala | Glu | Ala | D-Val | Ala | Gln | 1 | 1 |
| Ala | D-Ala | Glu | Ala | D-Phe | Leu | Asn | 1 | 1 |
| Ala | D-Ala | Glu | Ala | D-Phe | Leu | Gln | 1 | 1 |
| Ala | D-Ala | Glu | Ala | D-Phe | Ala | Asn | 1 | 1 |
| Ala | D-Ala | Glu | Ala | D-Phe | Ala | Gln | 1 | 1 |
| Ala | D-Phe | Glu | Val | D-Leu | Leu | Asn | 1 | 1 |
| Ala | D-Phe | Glu | Val | D-Leu | Leu | Gln | 1 | 1 |
| Ala | D-Phe | Glu | Val | D-Leu | Ala | Asn | 1 | 1 |
| Ala | D-Phe | Glu | Val | D-Leu | Ala | Gln | 1 | 1 |
| Ala | D-Phe | Glu | Val | D-Ala | Leu | Asn | 1 | 1 |
| Ala | D-Phe | Glu | Val | D-Ala | Leu | Gln | 1 | 1 |
| Ala | D-Phe | Glu | Val | D-Ala | Ala | Asn | 1 | 1 |
| Ala | D-Phe | Glu | Val | D-Ala | Ala | Gln | 1 | 1 |
| Ala | D-Phe | Glu | Val | D-Val | Leu | Asn | 1 | 1 |
| Ala | D-Phe | Glu | Val | D-Val | Leu | Gln | 1 | 1 |
| Ala | D-Phe | Glu | Val | D-Val | Ala | Asn | 1 | 1 |
| Ala | D-Phe | Glu | Val | D-Val | Ala | Gln | 1 | 1 |
| Ala | D-Phe | Glu | Val | D-Phe | Leu | Asn | 1 | 1 |
| Ala | D-Phe | Glu | Val | D-Phe | Leu | Gln | 1 | 1 |
| Ala | D-Phe | Glu | Val | D-Phe | Ala | Asn | 1 | 1 |
| Ala | D-Phe | Glu | Val | D-Phe | Ala | Gln | 1 | 1 |
| Ala | D-Phe | Glu | Ala | D-Leu | Leu | Asn | 1 | 1 |
| Ala | D-Phe | Glu | Ala | D-Leu | Leu | Gln | 1 | 1 |
| Ala | D-Phe | Glu | Ala | D-Leu | Ala | Asn | 1 | 1 |
| Ala | D-Phe | Glu | Ala | D-Leu | Ala | Gln | 1 | 1 |
| Ala | D-Phe | Glu | Ala | D-Ala | Leu | Asn | 1 | 1 |
| Ala | D-Phe | Glu | Ala | D-Ala | Leu | Gln | 1 | 1 |
| Ala | D-Phe | Glu | Ala | D-Ala | Ala | Asn | 1 | 1 |
| Ala | D-Phe | Glu | Ala | D-Ala | Ala | Gln | 1 | 1 |
| Ala | D-Phe | Glu | Ala | D-Val | Leu | Asn | 1 | 1 |
| Ala | D-Phe | Glu | Ala | D-Val | Leu | Gln | 1 | 1 |
| Ala | D-Phe | Glu | Ala | D-Val | Ala | Asn | 1 | 1 |
| Ala | D-Phe | Glu | Ala | D-Val | Ala | Gln | 1 | 1 |
| Ala | D-Phe | Glu | Ala | D-Phe | Leu | Asn | 1 | 1 |
| Ala | D-Phe | Glu | Ala | D-Phe | Leu | Gln | 1 | 1 |
| Ala | D-Phe | Glu | Ala | D-Phe | Ala | Asn | 1 | 1 |
| Ala | D-Phe | Glu | Ala | D-Phe | Ala | Gln | 1 | 1 |
| Ala | D-Leu | Asp | Val | D-Leu | Leu | Asn | 1 | 1 |
| Ala | D-Leu | Asp | Val | D-Leu | Leu | Gln | 1 | 1 |
| Ala | D-Leu | Asp | Val | D-Leu | Ala | Asn | 1 | 1 |
| Ala | D-Leu | Asp | Val | D-Leu | Ala | Gln | 1 | 1 |
| Ala | D-Leu | Asp | Val | D-Ala | Leu | Asn | 1 | 1 |
| Ala | D-Leu | Asp | Val | D-Ala | Leu | Gln | 1 | 1 |
| Ala | D-Leu | Asp | Val | D-Ala | Ala | Asn | 1 | 1 |
| Ala | D-Leu | Asp | Val | D-Ala | Ala | Gln | 1 | 1 |
| Ala | D-Leu | Asp | Val | D-Val | Leu | Asn | 1 | 1 |
| Ala | D-Leu | Asp | Val | D-Val | Leu | Gln | 1 | 1 |
| Ala | D-Leu | Asp | Val | D-Val | Ala | Asn | 1 | 1 |
| Ala | D-Leu | Asp | Val | D-Val | Ala | Gln | 1 | 1 |
| Ala | D-Leu | Asp | Val | D-Phe | Leu | Asn | 1 | 1 |
| Ala | D-Leu | Asp | Val | D-Phe | Leu | Gln | 1 | 1 |
| Ala | D-Leu | Asp | Val | D-Phe | Ala | Asn | 1 | 1 |
| Ala | D-Leu | Asp | Val | D-Phe | Ala | Gln | 1 | 1 |
| Ala | D-Leu | Asp | Ala | D-Leu | Leu | Asn | 1 | 1 |
| Ala | D-Leu | Asp | Ala | D-Leu | Leu | Gln | 1 | 1 |
| Ala | D-Leu | Asp | Ala | D-Leu | Ala | Asn | 1 | 1 |
| Ala | D-Leu | Asp | Ala | D-Leu | Ala | Gln | 1 | 1 |
| Ala | D-Leu | Asp | Ala | D-Ala | Leu | Asn | 1 | 1 |
| Ala | D-Leu | Asp | Ala | D-Ala | Leu | Gln | 1 | 1 |
| Ala | D-Leu | Asp | Ala | D-Ala | Ala | Asn | 1 | 1 |
| Ala | D-Leu | Asp | Ala | D-Ala | Ala | Gln | 1 | 1 |
| Ala | D-Leu | Asp | Ala | D-Val | Leu | Asn | 1 | 1 |
| Ala | D-Leu | Asp | Ala | D-Val | Leu | Gln | 1 | 1 |
| Ala | D-Leu | Asp | Ala | D-Val | Ala | Asn | 1 | 1 |
| Ala | D-Leu | Asp | Ala | D-Val | Ala | Gln | 1 | 1 |
| Ala | D-Leu | Asp | Ala | D-Phe | Leu | Asn | 1 | 1 |
| Ala | D-Leu | Asp | Ala | D-Phe | Leu | Gln | 1 | 1 |
| Ala | D-Leu | Asp | Ala | D-Phe | Ala | Asn | 1 | 1 |
| Ala | D-Leu | Asp | Ala | D-Phe | Ala | Gln | 1 | 1 |
| Ala | D-Ala | Asp | Val | D-Leu | Leu | Asn | 1 | 1 |
| Ala | D-Ala | Asp | Val | D-Leu | Leu | Gln | 1 | 1 |
| Ala | D-Ala | Asp | Val | D-Leu | Ala | Asn | 1 | 1 |
| Ala | D-Ala | Asp | Val | D-Leu | Ala | Gln | 1 | 1 |
| Ala | D-Ala | Asp | Val | D-Ala | Leu | Asn | 1 | 1 |
| Ala | D-Ala | Asp | Val | D-Ala | Leu | Gln | 1 | 1 |
| Ala | D-Ala | Asp | Val | D-Ala | Ala | Asn | 1 | 1 |
| Ala | D-Ala | Asp | Val | D-Ala | Ala | Gln | 1 | 1 |
| Ala | D-Ala | Asp | Val | D-Val | Leu | Asn | 1 | 1 |
| Ala | D-Ala | Asp | Val | D-Val | Leu | Gln | 1 | 1 |
| Ala | D-Ala | Asp | Val | D-Val | Ala | Asn | 1 | 1 |
| Ala | D-Ala | Asp | Val | D-Val | Ala | Gln | 1 | 1 |
| Ala | D-Ala | Asp | Val | D-Phe | Leu | Asn | 1 | 1 |
| Ala | D-Ala | Asp | Val | D-Phe | Leu | Gln | 1 | 1 |
| Ala | D-Ala | Asp | Val | D-Phe | Ala | Asn | 1 | 1 |
| Ala | D-Ala | Asp | Val | D-Phe | Ala | Gln | 1 | 1 |
| Ala | D-Ala | Asp | Ala | D-Leu | Leu | Asn | 1 | 1 |
| Ala | D-Ala | Asp | Ala | D-Leu | Leu | Gln | 1 | 1 |
| Ala | D-Ala | Asp | Ala | D-Leu | Ala | Asn | 1 | 1 |
| Ala | D-Ala | Asp | Ala | D-Leu | Ala | Gln | 1 | 1 |
| Ala | D-Ala | Asp | Ala | D-Ala | Leu | Asn | 1 | 1 |
| Ala | D-Ala | Asp | Ala | D-Ala | Leu | Gln | 1 | 1 |
| Ala | D-Ala | Asp | Ala | D-Ala | Ala | Asn | 1 | 1 |
| Ala | D-Ala | Asp | Ala | D-Ala | Ala | Gln | 1 | 1 |
| Ala | D-Ala | Asp | Ala | D-Val | Leu | Asn | 1 | 1 |
| Ala | D-Ala | Asp | Ala | D-Val | Leu | Gln | 1 | 1 |
| Ala | D-Ala | Asp | Ala | D-Val | Ala | Asn | 1 | 1 |
| Ala | D-Ala | Asp | Ala | D-Val | Ala | Gln | 1 | 1 |
| Ala | D-Ala | Asp | Ala | D-Phe | Leu | Asn | 1 | 1 |
| Ala | D-Ala | Asp | Ala | D-Phe | Leu | Gln | 1 | 1 |
| Ala | D-Ala | Asp | Ala | D-Phe | Ala | Asn | 1 | 1 |
| Ala | D-Ala | Asp | Ala | D-Phe | Ala | Gln | 1 | 1 |
| Ala | D-Phe | Asp | Val | D-Leu | Leu | Asn | 1 | 1 |
| Ala | D-Phe | Asp | Val | D-Leu | Leu | Gln | 1 | 1 |
| Ala | D-Phe | Asp | Val | D-Leu | Ala | Asn | 1 | 1 |
| Ala | D-Phe | Asp | Val | D-Leu | Ala | Gln | 1 | 1 |
| Ala | D-Phe | Asp | Val | D-Ala | Leu | Asn | 1 | 1 |
| Ala | D-Phe | Asp | Val | D-Ala | Leu | Gln | 1 | 1 |
| Ala | D-Phe | Asp | Val | D-Ala | Ala | Asn | 1 | 1 |
| Ala | D-Phe | Asp | Val | D-Ala | Ala | Gln | 1 | 1 |
| Ala | D-Phe | Asp | Val | D-Val | Leu | Asn | 1 | 1 |
| Ala | D-Phe | Asp | Val | D-Val | Leu | Gln | 1 | 1 |
| Ala | D-Phe | Asp | Val | D-Val | Ala | Asn | 1 | 1 |
| Ala | D-Phe | Asp | Val | D-Val | Ala | Gln | 1 | 1 |
| Ala | D-Phe | Asp | Val | D-Phe | Leu | Asn | 1 | 1 |
| Ala | D-Phe | Asp | Val | D-Phe | Leu | Gln | 1 | 1 |
| Ala | D-Phe | Asp | Val | D-Phe | Ala | Asn | 1 | 1 |
| Ala | D-Phe | Asp | Val | D-Phe | Ala | Gln | 1 | 1 |
| Ala | D-Phe | Asp | Ala | D-Leu | Leu | Asn | 1 | 1 |
| Ala | D-Phe | Asp | Ala | D-Leu | Leu | Gln | 1 | 1 |
| Ala | D-Phe | Asp | Ala | D-Leu | Ala | Asn | 1 | 1 |
| Ala | D-Phe | Asp | Ala | D-Leu | Ala | Gln | 1 | 1 |
| Ala | D-Phe | Asp | Ala | D-Ala | Leu | Asn | 1 | 1 |
| Ala | D-Phe | Asp | Ala | D-Ala | Leu | Gln | 1 | 1 |
| Ala | D-Phe | Asp | Ala | D-Ala | Ala | Asn | 1 | 1 |
| Ala | D-Phe | Asp | Ala | D-Ala | Ala | Gln | 1 | 1 |
| Ala | D-Phe | Asp | Ala | D-Val | Leu | Asn | 1 | 1 |
| Ala | D-Phe | Asp | Ala | D-Val | Leu | Gln | 1 | 1 |
| Ala | D-Phe | Asp | Ala | D-Val | Ala | Asn | 1 | 1 |
| Ala | D-Phe | Asp | Ala | D-Val | Ala | Gln | 1 | 1 |
| Ala | D-Phe | Asp | Ala | D-Phe | Leu | Asn | 1 | 1 |
| Ala | D-Phe | Asp | Ala | D-Phe | Leu | Gln | 1 | 1 |
| Ala | D-Phe | Asp | Ala | D-Phe | Ala | Asn | 1 | 1 |
| Ala | D-Phe | Asp | Ala | D-Phe | Ala | Gln | 1 | 1 |
| Ala | D-Val | Asp | Val | D-Leu | Leu | Asn | 1 | 1 |

-continued

| A | B | W | D | E | F | Z | m | n |
|---|---|---|---|---|---|---|---|---|
| Ala | D-Val | Asp | Val | D-Leu | Leu | Gln | 1 | 1 |
| Ala | D-Val | Asp | Val | D-Leu | Ala | Asn | 1 | 1 |
| Ala | D-Val | Asp | Val | D-Leu | Ala | Gln | 1 | 1 |
| Ala | D-Val | Asp | Val | D-Ala | Leu | Asn | 1 | 1 |
| Ala | D-Val | Asp | Val | D-Ala | Leu | Gln | 1 | 1 |
| Ala | D-Val | Asp | Val | D-Ala | Ala | Asn | 1 | 1 |
| Ala | D-Val | Asp | Val | D-Ala | Ala | Gln | 1 | 1 |
| Ala | D-Val | Asp | Val | D-Val | Leu | Asn | 1 | 1 |
| Ala | D-Val | Asp | Val | D-Val | Leu | Gln | 1 | 1 |
| Ala | D-Val | Asp | Val | D-Val | Ala | Asn | 1 | 1 |
| Ala | D-Val | Asp | Val | D-Val | Ala | Gln | 1 | 1 |
| Ala | D-Val | Asp | Val | D-Phe | Leu | Asn | 1 | 1 |
| Ala | D-Val | Asp | Val | D-Phe | Leu | Gln | 1 | 1 |
| Ala | D-Val | Asp | Val | D-Phe | Ala | Asn | 1 | 1 |
| Ala | D-Val | Asp | Val | D-Phe | Ala | Gln | 1 | 1 |
| Ala | D-Val | Asp | Ala | D-Leu | Leu | Asn | 1 | 1 |
| Ala | D-Val | Asp | Ala | D-Leu | Leu | Gln | 1 | 1 |
| Ala | D-Val | Asp | Ala | D-Leu | Ala | Asn | 1 | 1 |
| Ala | D-Val | Asp | Ala | D-Leu | Ala | Gln | 1 | 1 |
| Ala | D-Val | Asp | Ala | D-Ala | Leu | Asn | 1 | 1 |
| Ala | D-Val | Asp | Ala | D-Ala | Leu | Gln | 1 | 1 |
| Ala | D-Val | Asp | Ala | D-Ala | Ala | Asn | 1 | 1 |
| Ala | D-Val | Asp | Ala | D-Ala | Ala | Gln | 1 | 1 |
| Ala | D-Val | Asp | Ala | D-Val | Leu | Asn | 1 | 1 |
| Ala | D-Val | Asp | Ala | D-Val | Leu | Gln | 1 | 1 |
| Ala | D-Val | Asp | Ala | D-Val | Ala | Asn | 1 | 1 |
| Ala | D-Val | Asp | Ala | D-Val | Ala | Gln | 1 | 1 |
| Ala | D-Val | Asp | Ala | D-Phe | Leu | Asn | 1 | 1 |
| Ala | D-Val | Asp | Ala | D-Phe | Leu | Gln | 1 | 1 |
| Ala | D-Val | Asp | Ala | D-Phe | Ala | Asn | 1 | 1 |
| Ala | D-Val | Asp | Ala | D-Phe | Ala | Gln | 1 | 1 |
| Ile | D-Leu | Asp | — | — | Val | Gln | 0 | 0 |
| Ile | D-Leu | Asp | — | Val | D-Leu | Gln | 0 | 1 |
| Ala | D-Leu | Asp | — | — | Val | Gln | 0 | 0 |
| Ala | D-Leu | Asp | — | Val | D-Leu | Gln | 0 | 1 |

In the description of the above formulae and the following Examples and others, the amino acid or amino acid residue constituting the peptides is referred to herein by means of the triliteral expression system generally employed for the indication of amino acids.

More specifically, there are applied the following expressions such as alanine=Ala, valine=Val, leucine=Leu, isoleucine=Ile, serine=Ser, threonine=Thr, aspartic acid=Asp, asparagine=Asn, glutamic acid=Glu, glutamine=Gln, lysine=Lys, cysteine=Cys, phenylalanine=Phe, tyrosine=Tyr, tryptophan=Trp, histidine=His, proline=Pro, 4-hydroxyproline=4Hyp, etc.

Agr. Biol. Chem., Vol. 33, No. 10, pp. 1523–1524, 1969, discloses the compound of the above formula (1) wherein m and n are 1, A is isoleucine, B is leucine, W is aspartic acid, D is valine, E is leucine, F is leucine, Z is glutamic acid and R is a group of the formula $R_1$—$(CH_2)_p$— (wherein $R_1$ is isopropyl and p is 9) as a surfactant having an anticoagulant activity. Tetrahedron Letters, Vol. 35, No. 31, pp. 5571–5574, 1994, discloses the compound of the above formula (1) wherein m, n, A, B, W, D, E, and F are as defined above, Z is glutamine and R is a group having the formula $R_1$—$(CH_2)_p$— (wherein $R_1$ is methyl and p is 11) as having an antifungal, antibacterial or anti-tumor activity. WO 95/32990 discloses the compound of the above formula (1) wherein m, n, A, B, W, D, E, and F are as defined above, Z is glutamine and R is a group having the formula $R_1$—$(CH_2)_p$— (wherein $R_1$ is isopropyl and p is 5–15) as a useful antihyperlipemic agent, an agent for inhibiting lipid secretion, or an agent for inhibiting the production of apolipoprotein B. Further, JP-A-7-291993 discloses that the compound of the above formula (1) wherein m, n, A, B, W, D, E, and F are as defined above, Z is glutamine and R is a group of the formula $R_1$—$(CH_2)_p$— (wherein $R_1$ is isopropyl, sec-butyl or isobutyl and p is 8) has an endothelin-antagonistic activity and is useful as a vasodilating agent, an antihyperlipemic agent and others. However, none of the above references discloses that these compounds have a promoting activity on the production of apolipoprotein E.

Of the cyclic depsipeptides of the present invention, the known compounds as described above can be produced by cultivating a microorganism capable of producing said depsipeptides which belongs to the genus of Bacillus (for example, Bacillus sp. No. 4691 strain (FERM BP-5101) and others) according to the processes as disclosed in WO95/32990, JP-A-7-291993 and others.

Alternatively, the cyclic depsipeptides of the invention can be also prepared, for example, according to the conventional procedures for the synthesis of peptides as mentioned below.

More specifically, the cyclic depsipeptides represented by the above formula (1) can be prepared according to the following steps comprising:

condensing a 3-hydroxy-middle chain or -long chain aliphatic acid having a protected carboxyl group represented by the formula (3)

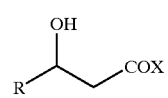

(3)

(wherein X is a protecting group for carboxyl group and R is as defined above), which is obtained by protecting the carboxyl group of a 3-hydroxy-middle chain or -long chain aliphatic acid represented by the formula (2)

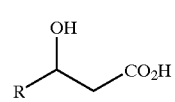

(2)

(wherein R is as defined above) with a suitable protecting group, with an amino acid A having a protected amino group to form a compound represented by the formula (4)

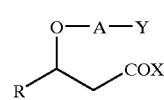

(4)

(wherein Y is an amino-protecting group and A, X and R are as defined above);

removing the amino-protecting group in the amino acid A of the compound to form a compound represented by the formula (5)

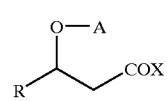

(5)

(wherein A, X and R are as defined above);

condensing the compound with an amino acid B having a protected amino group to form a depsipeptide represented by the formula (6)

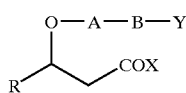 (6)

(wherein A, B, Y, X and R are as defined above);

removing the amino-protecting group in the amino acid B of the depsipeptide to form a depsipeptide represented by the formula (7)

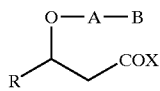 (7)

(wherein A, B, X and R are as defined above);

condensing the depsipeptide with aspartic acid having a protected amino group and a protected carboxyl group at the β-position, asparagine having a protected amino group and a protected carbamido group at the β-position, glutamic acid having a protected amino group and a protected carboxyl group at the γ-position or glutamine having a protected amino group and a protected carbamide group at the γ-position to form a depsipeptide represented by the formula

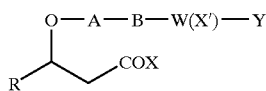 (8)

(wherein X' is a protecting group for a carboxyl group at the β-position of aspartic acid, a carboxyl group at the γ-position of glutamic acid, a carbamido group at the β-position of asparagine or a carbamido group at the γ-position of glutamine and A, B, W, X, Y and R are as defined above);

removing the amino-protecting group in aspartic acid, asparagine, glutamic acid or glutamine of the depsipeptide to form a depsipeptide represented by the formula (9)

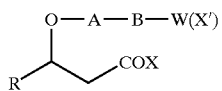 (9)

(wherein A, B, W, X, X' and R are as defined above);

condensing the depsipeptide with an amino acid D having a protected amino group to form a depsipeptide represented by the formula (10)

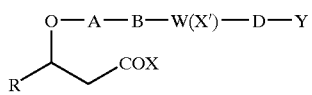 (10)

(wherein A, B, W, D, Y, X, X' and R are as defined above);

removing the amino-protecting group in the amino acid D of the depsipeptide to form a depsipeptide represented by the formula (11)

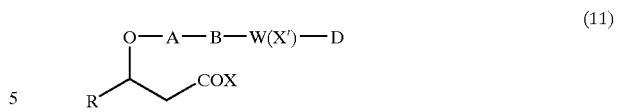 (11)

(wherein A, B, W, D, X, X' and R are as defined above);

condensing the depsipeptide with an amino acid E having a protected amino group or condensing the depsipeptide of the formula (9) with an amino acid E having a protected amino group, without the condensation step of the amino acid D, to form a compound represented by the formula (12)

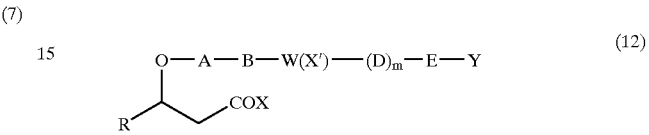 (12)

(wherein A, B, W, D, E, Y, X, X', R and m are as defined above);

removing the amino-protecting group in the amino acid E of the depsipeptide thus obtained to form a depsipeptide represented by the formula (13)

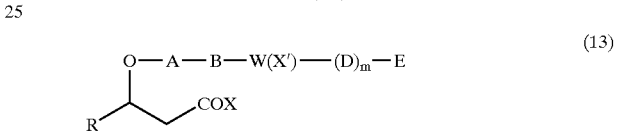 (13)

(wherein A, B, W, D, E, X, X' and R are as defined above);

condensing the depsipeptide with an amino acid F having a protected amino group or condensing the depsipeptide of the formula (11) or the formula (9) with an amino acid F having a protected amino group, without the condensation step of the amino acid E, to form a compound represented by the formula (14)

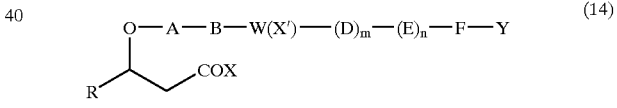 (14)

(wherein A, B, W, D, E, F, Y, X, X', R, m and n are as defined above);

removing the amino-protecting group in the amino acid F of the depsipeptide thus obtained to form a depsipeptide represented by the formula (15)

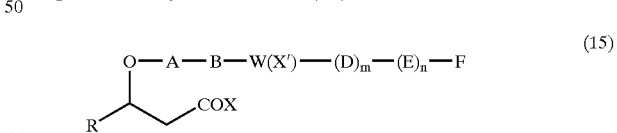 (15)

(wherein A, B, W, D, E, F, Y, X, X', R, m and n are as defined above);

condensing the depsipeptide with aspartic acid having a protected amino group and a protected carboxyl group at the β-position, asparagine having a protected amino group and a protected carbamido group at the β-position, glutamic acid having a protected amino group and a protected carboxyl group at the γ-position or glutamine having a protected amino group and a protected carbamide group at the γ-position to form a depsipeptide represented by the formula (16)

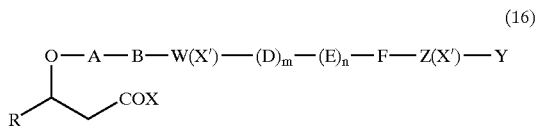
(16)

(wherein X" is a protecting group for a carboxyl group at the β-position of aspartic acid, a carboxyl group at the γ-position of glutamic acid, a carbamido group at the β-position of asparagine or a carbamido group at the γ-position of glutamine and A, B, W, D, E, F, Z, X, X', Y, R, m and n are as defined above);

removing the protecting group for the amino group of aspartic acid, asparagine, glutamic acid or glutamine of the depsipeptide to form a depsipeptide represented by the formula (17)

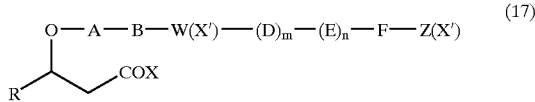
(17)

(wherein A, B, W, D, E, F, Z, X, X', X", R, m and n are as defined above);

removing the carboxyl-protecting group X of the depsipeptide followed by self-condensation to form a cyclic depsipeptide represented by the formula (18)

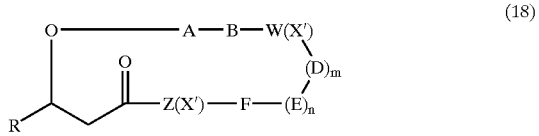
(18)

(wherein A, B, W, D, E, F, Z, X', X", R, m and n are as defined above); and deprotecting the carboxyl group at the β-position of the aspartic acid, the carboxyl group at the γ-position of the glutamic acid, the carbamido group at the β-position of asparagine or the carbamido group at the γ-position of glutamine of the cyclic depsipeptide.

The cyclic depsipeptides of the formula (1') can be prepared by condensing several synthesized oligopeptides followed by self-condensation, besides a process for the stepwise condensations of amino acids followed by self-condensation according to the conventional peptide synthesis as mentioned above.

According to this alternative process, the cyclic depsipeptides can be also prepared, for example, by the following steps comprising:

condensing the depsipeptide represented by the formula (9), which is obtained in the first half of the above-mentioned stepwise condensations,

(9)

(wherein A, B, W, X, X' and R are as defined above) with a tetrapeptide (or a tripeptide or a dipeptide) represented by the formula (19)

$(D)_m$—$(E)_n$—F—Z(X")—Y  (19)

(wherein D, E, F, Z, X", Y, m and n are as defined above), or condensing a depsipeptide represented by the formula (5)

(5)

(wherein A, X and R are as defined above) with a tripeptide (or a dipeptide) represented by the formula (19')

B—W(X')—$(D')_m$—Y  (19')

(wherein B, D, W, X', Y and m are as defined above), removing the amino-protecting group Y in the depsipeptide thus obtained, and further condensing with a tripeptide (or a dipeptide) represented by the formula (19")

$(E)_n$—F—Z(X")—Y  (19")

(wherein E, F, Z, X", Y and n are as defined above) to form the depsipeptide represented by the above formula (16);

removing the amino-protecting group of the aspartic acid, asparagine, glutamic acid or glutamine in the depsipeptide to form a depsipeptide represented by the formula (17)

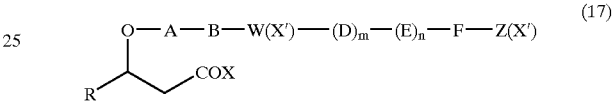
(17)

(wherein A, B, W, D, E, F, Z, X, X', X" and R are as defined above);

removing the carboxyl-protecting group X in the depsipeptide and subsequent self-condensation to form a cyclic depsipeptide represented by the formula (18)

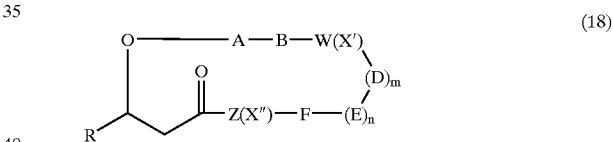
(18)

(wherein A, B, W, D, E, F, Z, X', X" and R are as defined above); and deprotecting the carboxyl group at the β-position of the aspartic acid, the carboxyl group at the γ-position of the glutamic acid, the carbamido group at the β-position of asparagine or the carbamido group at the γ-position of glutamine of the cyclic depsipeptide.

The cyclic depsipeptides thus prepared may be converted, if required, to pharmacologically acceptable salts thereof.

Any of the conventional processes adopted in peptide synthesis may be applied in the above synthesis steps for preparing the cyclic depsipeptides of the invention.

For instance, condensation reaction for forming a peptide bond includes a process using a condensing agent, azide process, a process using an acid anhydride, a process using an active ester, a process by redox, a process using an enzyme or the like.

Where peptide synthesis is to be carried out by the process using a condensing agent, there may be preferably employed N,N-dicyclohexyl-carbodiimide (hereinafter referred to as "DCC") or 1-ethyl-3-(3-dimethylaminopropyl)carbodiimide hydrochloride, i.e., water-soluble carbodiimide (hereinafter referred to as "WSCI"), O-(1H-benzotriazole-1-yl)-N,N,N', N'-tetramethyluronium tetrafluoroborate (hereinafter referred to as "TBTU"), benzotriazole-1-yl-oxy-tris (dimethylamino)-phosphonium hexafluorophosphate (hereinafter referred to as "BOP") and the like. It is also preferable to simultaneously add an additive commonly employed for preventing racemization such as N-hydroxysuccinimide, N-hydroxybenzotriazole (hereinafter referred to as "HOBt"), N-hydroxy-5-norbornene-2,3-dicarbodiimide-benzotriazole and the like.

Main condensing agents which may be employed in the azide process include diphenylphosphoryl azide (hereinafter referred to as "DPPA"), diethylphosphoryl cyanide and the like.

It is generally preferable to apply any known protection procedures to the carboxyl group, amino group, ω-carbamido group and the like, which do not participate in the said condensation reaction.

The protecting group which may be used in the protection procedures includes, for example, a t-butoxycarbonyl (hereinafter referred to as "Boc") group, a benzyloxycarbonyl group, a p-methoxy-benzyloxycarbonyl group or a 9-fluorenylmethoxy-carbonyl (hereinafter referred to as "FMoc") or the like as an amino-protecting group; a benzyloxy group or a t-butoxy (hereinafter referred to as "OtBu") or the like as a carboxyl-protecting group; 4,4-dimethoxy-benzhydryl (hereinafter referred to as "Mbh") group, a trityl group or the like as a terminal carbamido-protecting group.

Removal of the protecting groups in the preparation of the cyclic depsipeptide according to the present invention should be carried out without affecting the peptide linkage and it should be well chosen depending on the type of protecting groups used.

The solvent which may be employed in each peptide synthesis as depicted above includes, for example, anhydrous or hydrous chloroform, dichloromethane, ethyl acetate, N,N-dimethylformamide (hereinafter referred to as "DMF"), dimethyl sulfoxide, pyridine, dioxane, tetrahydrofuran (hereinafter referred to as "THF"), dimethoxyethane, acetonitrile and the like and they may be used in combination with two or more thereof if necessary. The condensation reaction may be carried out in a temperature range of from about −20 to 50° C. as usual Peptide synthesis may be carried out according to any of the liquid phase method and the solid phase method, and a column method or a batch method may be also applicable.

The cyclic depsipeptides of the present invention may be converted by a method known per se to pharmacologically acceptable salts thereof such as metal salts, e.g. sodium, potassium or calcium salt, ammonium salts or organic amine salts, e.g. triethylamine salts, and these pharmacologically acceptable salts may be also used as an agent for promoting the production of apolipoprotein E.

Illustrative examples of the 3-hydroxy-middle chain or -long chain aliphatic acid of the formula (2) as a starting material to be used for the synthesis of cyclic depsipeptides of the above formula (1) may be 3-hydroxy-capric acid, 3-hydroxy-lauric acid, 3-hydroxy-myristic acid and the like.

The 3-hydroxy-middle chain or -long chain aliphatic acid may be in any of D-isomer, L-isomer and racemate forms.

One example of the synthesis routes of the cyclic depsipeptides of the invention using 3-hydroxy-myristic acid as a starting material is illustrated by the following Reaction Scheme (SEQ ID NOS:1–7):

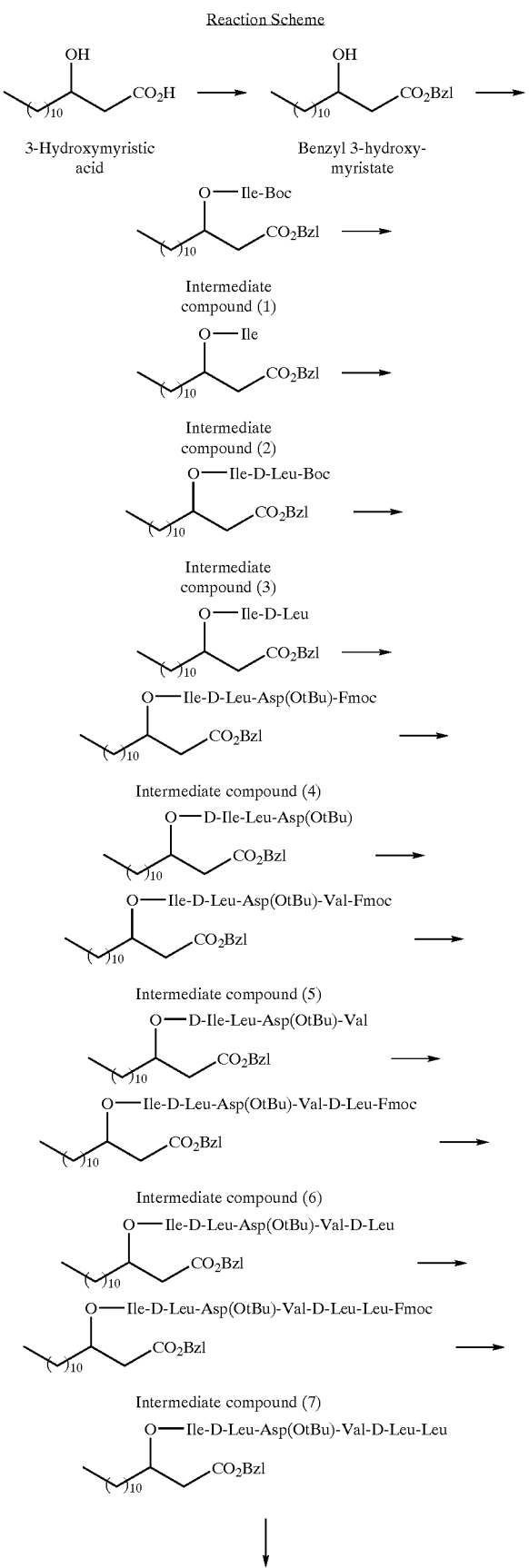

-continued

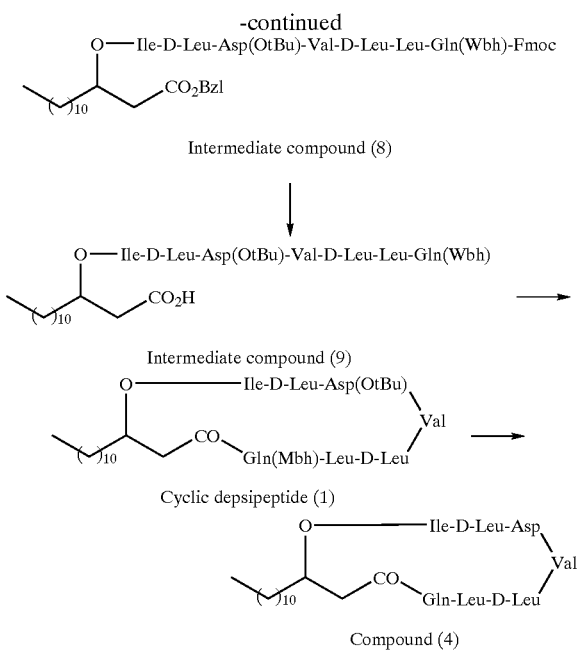

Intermediate compound (8)

Intermediate compound (9)

Cyclic depsipeptide (1)

Compound (4)

The cyclic depsipeptides of the invention may strongly promote the production of apolipoprotein E in Hep G2 cell that is the apolipoprotein-producing cell and therefore are useful as a therapeutic agent for neurologic damages and also as an antidementia agent. Moreover, they are useful for the treatment of disorders of peripheral nervous system such as diabetic neuropathy, disorders of peripheral nervous system caused by deficiency of Vitamin B group ($B_1$, $B_2$, $B_{12}$, etc.) and the like.

The cyclic depsipeptides or pharmacologically acceptable salts thereof according to the invention may greatly inhibit the production of apolipoprotein B and promote the production of apolipoprotein A1, while promoting the production of apolipoprotein E as described above, and they are then useful as an antihyperlipemic agent.

The cyclic depsipeptides or pharmacologically acceptable salts thereof according to the invention may be formulated to pharmaceutical preparations of various dosage forms. More specifically, such pharmaceutical preparations may be, for example, solid preparations such as tablets, hard capsules, soft capsules, granules, powders, etc. and liquid preparations such as solutions, emulsions, suspensions, etc. The preparations for parenteral administration may be injections, suppositories, etc.

In preparing such pharmaceutical preparations, conventional additives may be added, for example, excipients, stabilizers, antiseptics, solubilizers, wetting agents, emulsifying agents, lubricants, sweetening agents, coloring agents, flavors, isotonic agents, buffering agents, antioxidants and the like.

As the additives, there may be mentioned, for example, starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropyl-methylcellulose and the like.

Where the cyclic depsipeptides of the invention are to be applied in the form of solutions or injections, the cyclic depsipeptide or pharmacologically acceptable salt thereof as the active ingredient may be dissolved or suspended in any conventional diluent. The diluent may include, for example, a physiological saline, a Ringer's solution, an aqueous glucose solution, alcohols, fatty acid esters, glycols, glycerols, oils and fats derived from plant or animal sources, paraffins and the like. These preparations may be prepared according to any conventional method.

A usual clinical dose may be in the range of 0.5–5000 mg per day for adult when orally given. More preferably, it is in the range of 5–500 mg.

A usual dose may be in the range of 0.05–5000 mg per day for adult when parenterally administered.

Illustrative examples of the preparation of the present cyclic depsipeptides will be explained hereinafter by way of Synthesis Examples, test examples for the promoting action of the present cyclic depsipeptides on the production of apolipoprotein E will be given by way of Examples, and examples of the pharmaceutical preparations containing as an active ingredient the present cyclic depsipeptides will be illustrated by way of Preparation Examples.

In the following Synthesis Examples and Examples, if the amino acid constituting the depsipeptide or cyclic depsipeptide is in the form of a D-isomer, it will be specifically indicated, and unless otherwise specified, the corresponding amino acid shall be in the form of an L-isomer.

SYNTHESIS EXAMPLE 1

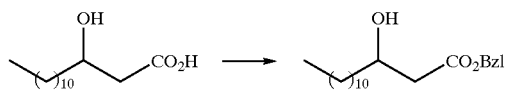

To a solution of 3-hydroxymyristic acid (5.00 g) and triethylamine (2.85 g) in DMF (50 ml) was added benzyl bromide (2.43 ml) and the mixture was stirred at room temperature overnight. After the solvent was removed in vacuo, to the residue were added ethyl acetate and water. The separated ethyl acetate layer was washed twice with water and then dried over anhydrous sodium sulfate. After the ethyl acetate was removed in vacuo, purification was carried out by a silica gel column chromatography (silica gel 30 g, chloroform:methanol=100:0–10) to afford 3.69 g of benzyl 3-hydroxymyristate.

(NMR data for benzyl 3-hydroxymyristate)

$^1$H-NMR (δ ppm, $CDCl_3$): 7.33–7.40 (5H, m), 5.16 (2H, s), 3.95–4.05 (1H, m), 2.85 (1H, d, J=4.4 Hz), 2.56 (1H, dd, J=2.9, 17 Hz), 2.46 (1H, dd, J=9.0, 17 Hz), 1.20–1.60 (20H, m), 0.88 (3H, t, J=6.8 Hz)

SYNTHESIS EXAMPLE 2

To a solution of benzyl 3-hydroxymyristate (3.00 g) obtained in Synthesis Example 1, Boc-isoleucine (2.22 g) and dimethylaminopyridine (77 mg) in dichloromethane (25 ml) was added dropwise under ice-cooling a solution of DDC (2.78 g) in dichloromethane (25 ml) and the mixture was stirred under ice-cooling for one hour and then at room temperature for 2 hours. After a precipitate was filtered off, the dichloromethane was removed in vacuo. The residue was dissolved in ethyl acetate and washed in turn with 0.5N hydrochloric acid, 5% aqueous sodium hydrogencarbonate and saturated aqueous sodium chloride, dried over anhydrous sodium sulfate. After the ethyl acetate was removed in vacuo, purification was carried out by a silica gel column chromatography (silica gel 100 g, hexane:ethyl acetate=200:0–15) to afford 4.62 g of the intermediate compound (1).

(NMR data for the intermediate compound (1)).

$^1$H-NMR (δ ppm, CDCl$_3$): 7.30–7.39 (5H, m), 5.24–5.33 (1H, m), 5.12 (1H, s), 5.10 (1H, d, J=2.5 Hz), 4.98–5.05 (1H, m), 4.15–4.25 (1H, m), 2.56–2.72 (2H, m), 1.75–1.90 (1H, m), 1.50–1.70 (2H, m), 1.20–1.45 (19H, m), 1.44 (9H, s), 1.10–1.20 (1H, m), 0.86–0.93 (9H, m)

SYNTHESIS EXAMPLE 3

A solution of the intermediate compound (1) (4.62 g) obtained in Synthesis Example 2 in trifluoroacetic acid (hereinafter referred to as "TFA") (9 ml) was stirred at room temperature for 15 minutes. After the TFA was removed in vacuo, the residue was dissolved in ethyl acetate and washed with 5% aqueous sodium hydrogencarbonate. It was dried over anhydrous sodium sulfate and then the ethyl acetate was removed in vacuo to afford 3.78 g of the intermediate compound (2).

(NMR data for the intermediate compound (2))

$^1$H-NMR (δ ppm, CDCl$_3$): 7.31–7.39 (5H, m), 5.24–5.32 (1H, m), 5.06–5.14 (2H, m), 3.02–3.29 (1H, m), 2.75–2.69 (2H, m), 1.50–1.75 (4H, m), 1.30–1.40 (1H, m), 1.10–1.30 (20H, m), 0.85–0.94 (9H, m)

SYNTHESIS EXAMPLE 4

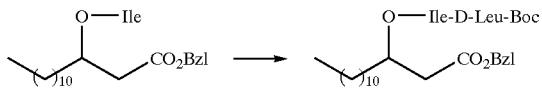

To a solution of the intermediate compound (2) (3.78 g) obtained in Synthesis Example 3, Boc-D-leucine· monohydrate (2.10 g) and HOBt·H$_2$O (1.25 g) in dichloromethane (50 ml) was added under ice-cooling WSCI (1.78 g). The solution was stirred under ice-cooling for one hour and then at room temperature overnight. After the dichloromethane was removed in vacuo, to the residue was added ethyl acetate and washed in turn with 1N hydrochloric acid, water, 5% aqueous sodium hydrogencarbonate and water and then dried over anhydrous sodium sulfate.

After the ethyl acetate was removed in vacuo, purification was carried out by a silica gel column chromatography (silica gel 80 g, hexane:ethyl acetate=200: 10–25) to afford 5.58 g of the intermediate compound (3).

(NMR Data for the Intermediate Compound (3))

$^1$H-NMR (δ ppm, CDCl$_3$): 7.30–7.39 (5H, m), 6.60–6.70 (1H, m), 5.25–5.30 (1H, m), 5.07–5.14 (2H, m), 4.75–4.95 (1H, m), 4.45–4.55 (1H, m), 4.10–4.20 (1H, m), 2.55–2.71 (2H, m), 1.80–1.95 (1H, m), 1.50–1.70 (3H, m), 1.35–1.50 (2H, m), 1.45 (9H, 2s), 1.20–1.35 (19H, m), 1.00–1.20 (1H, m), 0.85–0.95 (15H, m)

SYNTHESIS EXAMPLE 5

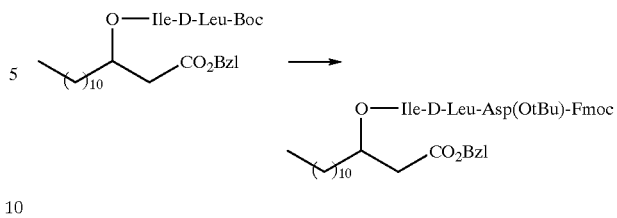

A solution of the intermediate compound (3) (8.77 g) obtained in Synthesis Example 4 in TFA (17 ml) was stirred at room temperature for 45 minutes. After the TFA was removed in vacuo, the residue was dissolved in ethyl acetate and washed with 5% aqueous sodium hydrogencarbonate. It was dried over anhydrous sodium sulfate and the ethyl acetate was removed in vacuo to afford the amine compound. To a solution of the amine compound thus obtained, Fmoc-L-aspartic acid β-t-butyl ester (5.46 g) and HOBt·H$_2$O (2.24 g) in dichloromethane (80 ml) was added under ice-cooling WSCI (2.80 g). This solution was stirred under ice-cooling for 2 hours and then at room temperature overnight. After the dichloromethane was removed in vacuo, to the residue were added ethyl acetate and 10% aqueous citric acid. The separated ethyl acetate layer was washed in turn with water, 5% aqueous sodium hydrogencarbonate and water, and then dried over anhydrous sodium sulfate. After the ethyl acetate was removed in vacuo, purification was carried out by a silica gel column chromatography (silica gel 60 g, hexane:ethyl acetate=200: 10–50) to afford 11.06 g of the intermediate compound (4).

(NMR Data for the Intermediate Compound (4))

$^1$H-NMR (δppm, CD$_3$OD): 7.78 (2H, d, J=7.8 Hz), 7.64 (2H, d, J=7.3 Hz), 7.38 (2H, t, J=7.6 Hz), 7.25–7.35 (7H, m), 5.20–5.25 (1H, m), 5.07 (1H, s), 5.06 (1H, s), 4.35–4.50 (3H, m), 4.25–4.35 (2H, m), 4.15–4.25 (1H, m), 2.70–2.80 (1H, m), 2.55–2.65 (3H, m), 1.75–1.90 (1H, m), 1.50–1.75 (4H, m), 1.44.(9H, s), 1.10–1.50 (21H, m), 0.75–0.95 (15H, m)

SYNTHESIS EXAMPLE 6

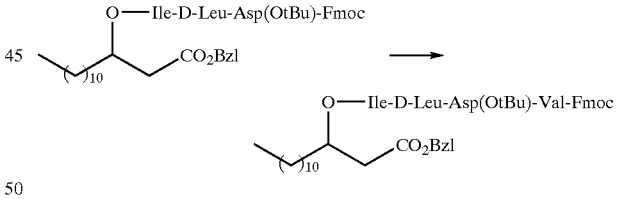

To a solution of the intermediate compound (4) (11.00 g) obtained in Synthesis Example 5 in DMF (125 ml) was added diethylamine (12.5 ml) and the mixture was stirred at room temperature for 2 hours. After the solvent was removed in vacuo, Fmoc-L-valine (3.91 g) and HOBt-monohydrate (1.94 g) were added and dissolved in dichloromethane (70 ml). To this solution was added under ice-cooling WSCI (2.43 g). The solution was stirred under ice-cooling for 2 hours and then at room temperature overnight. After the DMF was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by using a silica gel column chromatography (silica gel 100 g, chloroform:methanol 200:0–10) to afford 10.65 g of the intermediate compound (5).

(NMR Data for the Intermediate Compound (5))

$^1$H-NMR (δ ppm, CD$_3$OD): 7.66–7.82 (4H, m), 7.25–7.40 (9H, m), 5.15–5.25 (1H, m), 5.00–5.10 (2H, m), 4.60–4.65 (1H, m), 4.30–4.50 (3H, m), 4.20–4.30 (2H, m), 3.80 (1H, d, J=6.4 Hz), 2.90–3.00 (1H, m), 2.50–2.80 (3H, m), 2.00–2.10 (1H, m), 1.60–1.95 (3H, m), 1.35–1.60 (3H, m), 1.43 (9H, s), 1.10–1.35 (20H, m), 0.80–1.05 (21H, m)

SYNTHESIS EXAMPLE 7

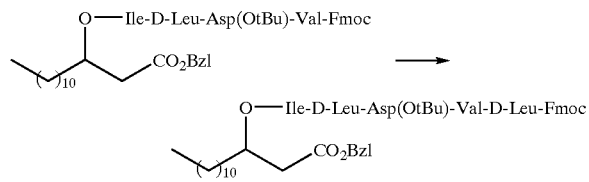

To a solution of the intermediate compound (5) (2.74 g) obtained in Synthesis Example 6 in DMF (30 ml) was added diethylamine (3 ml) and the mixture was stirred at room temperature for 4 hours. After the solvent was removed in vacuo, Fmoc-D-leucine (1.01 g) and HOBt-monohydrate (0.44 g) were added and dissolved in dichloromethane (15 ml). To this solution was added under ice-cooling WSCI (0.55 g). The solution was stirred under ice-cooling for 2 hours and then at room temperature overnight. After the DMF was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by using a silica gel column chromatography (silica gel 30 g, chloroform:methanol=200:0–2) to afford 2.54 g of the intermediate compound (6).

(NMR Data for the Intermediate Compound (6))

$^1$H-NMR (δ ppm, CD$_3$OD): 7.60–7.80 (4H, m), 7.25–7.40 (9H, m), 5.15–5.25 (1H, m), 5.19 (2H, s), 4.50–4.55 (1H, m), 4.25–4.40 (4H, m), 4.15–4.25 (2H, m), 4.13 (1H, d, J=5.9 Hz), 2.80–2.90 (1H, m), 2.50–2.80 (3H, m), 2.15–2.25 (1H, m), 1.80–1.90 (1H, m), 1.50–1.75 (7H, m), 1.36 (9H, s), 1.10–1.50 (21H, m), 0.80–1.00 (27H, m)

SYNTHESIS EXAMPLE 8

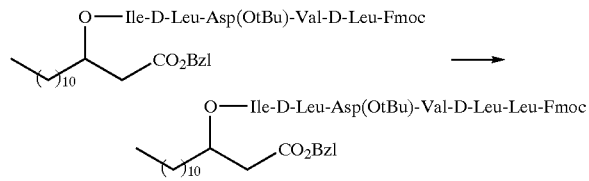

To a solution of the intermediate compound (6) (2.00 g) obtained in Synthesis Example 7 in DMF (20 ml) was added diethylamine (2 ml) and the mixture was stirred at room temperature for 4 hours. After the solvent was removed in vacuo, Fmoc-L-leucine (0.67 g) and HOBt-monohydrate (0.29 g) were added and dissolved in dichloromethane (20 ml). To this solution was added under ice-cooling WSCI (0.36 g). The solution was stirred under ice-cooling for 2 hours and then at room temperature overnight. After the dichloromethane was removed in vacuo, to the residue were added chloroform and 10% aqueous citric acid. The separated chloroform layer was washed in turn with water, 5% aqueous sodium hydrogencarbonate and water and then dried over anhydrous sodium sulfate. After the chloroform was removed in vacuo, purification was carried out by using a silica gel column chromatography (silica gel 25 g, chloroform methanol=200:0–6) to afford 2.19 g of the intermediate compound (7).

(NMR Data for the Intermediate Compound (7))

$^1$H-NMR (δ ppm, CD$_3$OD): 7.75–7.80 (2H, m), 7.55–7.65 (2H, m), 7.25–7.40 (9H, m), 5.20–5.30 (1H, m), 5.05–5.10 (2H, m), 4.15–4.65 (7H, m), 4.00–4.10 (1H, m), 3.85–3.95 (1H, m), 2.90–3.00 (1H, m), 2.55–2.75 (3H, m), 2.05–2.15 (1H, m), 1.85–1.95 (1H, m), 1.50–1.80 (10H, m), 1.37, 1.39 (9H, 2s), 1.10–1.50 (21H, m), 0.75–1.00 (33H, m)

SYNTHESIS EXAMPLE 9

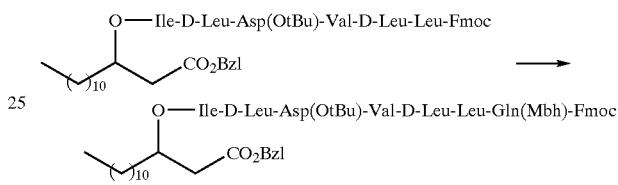

To a solution of the intermediate compound (7) (2.00 g) obtained in Synthesis Example 8 in DMF (20 ml) was added diethylamine (2 ml) and the mixture was stirred at room temperature for 2.5 hours. After the solvent was removed in vacuo, N-α-Fmoc-γ-Mbh-L-glutamine (1.02 g) and HOBt·monohydrate (0.26 g) were added and dissolved in a mixed solvent of DMF (20 ml) and dichloromethane (10 ml). To this solution was added under ice-cooling WSCI (0.33 g). The solution was stirred under ice-cooling for 2 hours and then at room temperature for 2 days. After the mixed solvent was removed in vacuo, to the residue were added chloroform and 10% aqueous citric acid. The separated chloroform layer was washed in turn with water, 5% aqueous sodium hydrogencarbonate and water and then dried over anhydrous sodium sulfate. After the chloroform was removed in vacuo, purification was carried out by using a silica gel column chromatography (silica gel 50 g, chloroform: methanol=200:0–4) to afford 1.92 g of the intermediate compound (8).

(NMR Data for the Intermediate Compound (8))

$^1$H-NMR (δ ppm, CD$_3$OD): 7.20–7.40 (10H, m), 7.13 (4H, d, J=8.3 Hz), 6.83 (4H, dd, J=2.0, 8.8 Hz), 6.08 (1H, s), 5.15–5.25 (1H, m), 5.00–5.10 (4H, m), 4.70–4.80 (1H, m), 4.50–4.60 (1H, m), 4.30–4.50 (2H, m), 4.20–4.30 (2H, m), 4.01 (1H, d, J=6.4 Hz), 3.76 (6H, s), 2.90–2.95 (1H, m), 2.75–2.85 (1H, m), 2.60–2.70 (2H, m), 2.35–2.45 (2H, m), 2.10–2.20 (1H, m), 1.80–2.05 (3H, m), 1.50–1.80 (10H, m), 1.41 (9H, s), 1.10–1.50 (21H, m), 0.80–1.00 (33H, m)

SYNTHESIS EXAMPLE 10

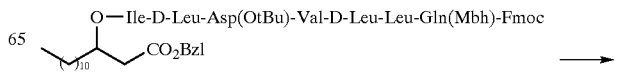

-continued

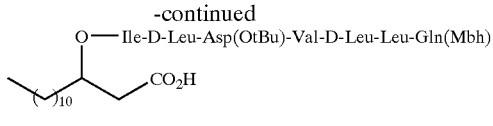

To a solution of the intermediate compound (8) (1.85 g) obtained in Synthesis Example 9 in DMF (20 ml) was added diethylamine (2 ml) and the mixture was stirred at room temperature for one hour. After the solvent was removed in vacuo, the residue was dissolved in methanol (60 ml), 5% palladium carbon (0.20 g) was added and the mixture was stirred under hydrogen atmosphere for 3 hours. The palladium carbon was filtered off. The methanol was removed in vacuo and then the crude product thus obtained was purified by a silica gel column chromatography (silica gel 30 g, chloroform:methanol=200:0–30) to afford 1.16 g of the intermediate compound (9).

(NMR Data for the Intermediate Compound (9))

$^1$H-NMR ($\delta$ ppm, $CD_3OD$): 7.14 (4H, d, J=8.3 Hz), 6.85 (4H, dd, J=2.2, 9.3 Hz), 6.08 (1H, s), 5.23 (1H, quint., J=6.0 Hz), 4.79 (1H, dd, J=5.0, 8.8 Hz), 4.46 (1H, dd, J=10, 21 Hz), 4.46 (1H, t, J=10 Hz), 4.28 (1H, d, J=6.8 Hz), 4.24 (1H, t, J=7.4 Hz), 4.02 (1H, d, J=6.4 Hz), 3.84 (1H, t, J=14 Hz), 3.77 (6H, 2s), 3.01 (1H, dd, J=5.2, 16 Hz), 2.75 (1H, dd, J=9.0, 16 Hz), 2.37–2.52 (3H, m), 2.34 (1H, dd, J=6.6, 15 Hz), 2.02–2.19 (2H, m), 1.83–2.02 (2H, m), 1.54–1.83 (10H, m), 1.44 (9H, s), 1.08–1.53 (21H, m), 0.81–1.08 (33H, m)

SYNTHESIS EXAMPLE 11

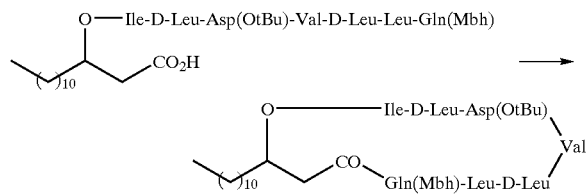

To a solution of the intermediate compound (9) (0.50 g) obtained in Synthesis Example 10 in DMF (200 ml) was added under ice-cooling DPPA (0.09 ml). Triethylamine (0.06 ml) was further added and the mixture was stirred under ice-cooling for 3 hours and then at room temperature overnight. After the solution was ice-cooled, DPPA (0.09 ml) and triethylamine (0.06 ml) were added. The solution was stirred under ice-cooling for 4 hours and then at room temperature for 3 days. After the solvent was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by using a silica gel column chromatography (silica gel 25 g, chloroform:methanol=200:0–4) to afford 0.35 g of the cyclic depsipeptide (1) of the present invention.

(NMR Data for the Cyclic Depsipeptide (1))

$^1$H-NMR ($\delta$ ppm, $CD_3OD$): 7.07–7.20 (4H, m), 6.80–6.92 (4H, m), 6.01–6.10 (1H, m), 5.14–5.29 (1H, m), 4.67–4.78 (1H, m), 4.21–4.45 (5H, m), 4.06–4.16 (1H, m), 3.77 (3H, s), 3.76 (3H, s), 2.62–2.85 (2H, m), 2.47–2.58 (1H, m), 2.21–2.44 (3H, m), 1.81–1.94 (4H, m), 1.53–1.81 (10H, m), 1.44 (9H, s), 1.08–1.53 (21H, m), 0.74–1.08 (33H, m)

SYNTHESIS EXAMPLE 12

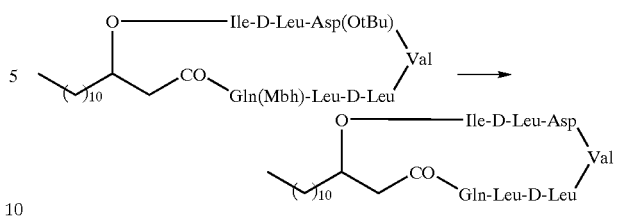

A solution of the cyclic depsipeptide (1) obtained (0.35 g) in Synthesis Example 11 in TFA (5 ml) was stirred at room temperature for 1.5 hours. After the TFA was removed in vacuo, the residue was neutralized with 5% aqueous sodium hydrogencarbonate and extracted with a 10% methanolic solution of chloroform. The chloroform layer was dried over anhydrous sodium sulfate, the solvent was removed in vacuo and then purification was carried out by a silica gel column chromatography (silica gel 20 g, chloroform:methanol=100:0–50) to afford 0.23 g of the cyclic depsipeptide (2) of the invention (hereinafter referred to as "Compound 4").

(NMR Data for Compound 4)

$^1$H-NMR ($\delta$ ppm, $CD_3OD$): 5.20–5.30 (1H, m), 4.80–4.90 (1H, m), 4.20–4.50 (5H, m), 4.10–4.20 (1H, m), 2.80–2.95 (2H, m), 2.40–2.55 (2H, m), 2.10–2.25 (2H, m), 1.80–2.00 (4H, m), 1.45–1.80 (10H, m), 1.10–1.45 (21H, m), 0.70–1.10 (33H, m)

SYNTHESIS EXAMPLE 13

BzlO-Ala+D-Leu-Fmoc→Fmoc-D-Leu-Ala-OBzl
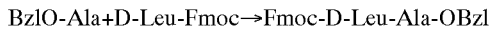

To L-alanine benzyl ester·p-toluenesulfonate (3.16 g) were added ethyl acetate (100 ml) and 5% aqueous sodium hydrogencarbonate (50 ml), the mixture was vigorously stirred and then allowed to stand. The separated ethyl acetate layer was dried over anhydrous sodium sulfate. After the solvent was removed in vacuo, Fmoc-D-leucine (3.18 g) and HOBt·monohydrate (1.35 g) were added and dissolved in dichloromethane (100 ml). To this solution was added under ice-cooling WSCI (2.59 g). The solution was stirred under ice-cooling for one hour, allowed to gradually rise up to room temperature and then stirred overnight. The reaction solution was washed in turn with 10% aqueous citric acid, water, 5% aqueous sodium hydrogencarbonate and water and then dried over anhydrous sodium sulfate. After the solvent was removed in vacuo, purification was carried out by using a silica gel column chromatography (silica gel 50 g, chloroform:methanol:aqueous ammonia=20:1:0.05) to afford 5.36 g of the dipeptide (1).

(NMR Data for the Dipeptide (1))

$^1$H-NMR ($\delta$ ppm, $CDCl_3$) 7.76 (2H, d, J=7.8 Hz), 7.58 (2H, d, J=7.3 Hz), 7.28–7.42 (9H, m), 6.57 (1H, d, J=6.3 Hz), 5.18 (1H, d, J=12.2 Hz), 5.12 (1H, d, J=12.2 Hz), 5.09 (1H, d, J=8.3 Hz), 4.57–4.64 (1H, m), 4.41–4.46 (2H, m), 4.20–4.23 (2H, m), 1.48–1.69 (3H, m), 1.41 (3H, d, J=6.8 Hz), 0.93 (3H, d, J=6.8 Hz)

SYNTHESIS EXAMPLE 14

Fmoc-D-Leu-Ala-OBzl→Fmoc-Leu-D-Leu-Ala-OBzl
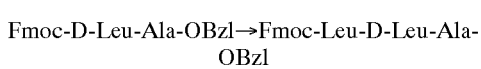

The dipeptide (1) (5.36 g) obtained in Synthesis Example 13 was dissolved in DMF (50 ml), diethylamine (5 ml) was added and then the mixture was stirred at room temperature for 2 hours. After the solvent was removed in vacuo, Fmoc-L-leucine (3.18 g) and HOBt·monohydrate (1.35 g) were added and dissolved in dichloromethane (100 ml). To this solution was added under ice-cooling WSCI (2.59 g). The solution was stirred under ice-cooling for one hour, allowed to gradually rise up to room temperature and then stirred overnight. The reaction solution was washed in turn with 10% aqueous citric acid, water, 5% aqueous sodium hydrogencarbonate and water and then dried over anhydrous sodium sulfate. After the solvent was removed in vacuo, purification was carried out by using a silica gel column chromatography (silica gel 50 g, chloroform:methanol:aqueous ammonia=50:1:0.05) to afford 7.18 g of the tripeptide (1).

(NMR Data for the Tripeptide (1))
$^{1}$H-NMR (δ ppm, CDCl$_{3}$) 7.75 (2H, d, J=7.3 Hz), 7.53–7.57 (2H, m), 7.28–7.41 (9H, m), 7.01 (1H, d, J=6.8 Hz), 6.43 (1H, d, J=8.3 Hz), 5.20 (1H, d, J=6.8 Hz), 5.12 (1H, d, J=12.2 Hz), 5.05 (1H, d, J12.2 Hz), 4.06–4.56 (6H, m), 1.47–1.78 (6H, m), 1.34 (3H, d, J=7.3 Hz), 0.90–0.95 (12H, 25 m)

SYNTHESIS EXAMPLE 15

Fmoc-Leu-D-Leu-Ala-OBzl→Leu-D-Leu-Ala-OBzl

The tripeptide (1) (7.08 g) obtained in Synthesis Example 14 was dissolved in DMF (70 ml), diethylamine (7 ml) was added and then the mixture was stirred at room temperature for 2 hours. After the solvent was removed in vacuo, purification was carried out by using a silica gel column chromatography (silica gel 100 g, chloroform methanol:aqueous ammonia=50:1:0.05 to 10:1 0.05) to afford 2.08 g of the tripeptide (2).

(NMR Data for the Tripeptide (2))
$^{1}$H-NMR (δ ppm, CDCl$_{3}$) 7.57 (1H, d, J=8.3 Hz), 7.31–7.38 (5H, m), 6.86 (1H, d, J=7.3 Hz), 5.19 (1H, d, J=12.2 Hz), 5.11 (1H, d, J=12.2 Hz), 4.52–4.59 (1H, m), 4.41–4.47 (1H, m), 3.38 (1H, dd, J=3.9, 9.8 Hz), 1.28–1.79 (6H, m), 1.40 (3H, d, J=6.8 Hz), 0.91–0.96 (12H, m)

SYNTHESIS EXAMPLE 16

Leu-D-Leu-Ala-OBzl→Fmoc-Gln(Mbh)-Leu-D-Leu-Ala-OBzl

The tripeptide (2) (2.08 g) obtained in Synthesis Example 15, N-α-Fmoc-N-γ-Mbh-L-glutamine (3.05 g) and HOBt·monohydrate (0.76 g) were dissolved in a mixed solvent of dichloromethane (30 ml) and DMF (3 ml). To this solution was added under ice-cooling WSCI (1.47 g). The solution was stirred under ice-cooling for one hour, allowed to gradually rise up to room temperature and then stirred overnight. The reaction solution was diluted with chloroform (100 ml) and washed in turn with 10% aqueous citric acid, water, 5% aqueous sodium hydrogencarbonate and water and then dried over anhydrous sodium sulfate. The solvent was removed in vacuo to afford 5.02 g of the tetrapeptide (1).

(NMR Data for the Tetrapeptide (1))
$^{1}$H-NMR (δ ppm, d-DMSO) 8.52 (1H, d, J=8.8 Hz), 7.27–8.13 (18H, m), 7.08–7.15 (4H, m), 6.83–6.85 (4H, m), 6.01 (1H, d, J=8.3 Hz), 5.06 (1H, d, J=12.7 Hz), 5.11 (1H, d, J=12.7 Hz), 4.01–4.27 (7H, m), 3.70 (6H, s), 2.23–2.29 (2H, m), 1.79–1.92 (2H, m), 1.46–1.58 (6H, m), 1.29 (3H, d, J=7.3 Hz), 0.78–0.87 (12H, m)

SYNTHESIS EXAMPLE 17

Fmoc-Gln(Mbh)-Leu-D-Leu-Ala-OBzl→Fmoc-Gln(Mbh)-Leu-D-Leu-Ala(Mbh)-Fmoc

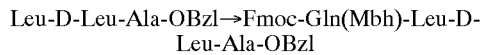

The tetrapeptide (1) (1.50 g) obtained in Synthesis Example 16 was dissolved in a mixed solvent of methanol (150 ml) and DMF (75 ml), 10% palladium carbon was added and the mixture was stirred under hydrogen atmosphere for 2 hours. After the palladium carbon was filtered off, the solvent was removed in vacuo to afford 1.43 g of the tetrapeptide (2).

(NMR Data for the Tetrapeptide (2))
$^{1}$H-NMR (δ ppm, d-DMSO) 8.56 (1H, d, J=8.8 Hz), 7.28–8.17 (12H, m), 7.13–7.16 (4H, m), 6.82–6.85 (4H, m), 6.01 (1H, d, J=8.3 Hz), 4.09–4.27 (7H, m), 3.71 (6H, s), 2.24–2.33 (2H, m), 1.75–1.92 (2H, m), 1.44–1.59 (6H, m), 1.24 (3H, d, J=7.3 Hz), 0.78–0.87 (12H, m)

SYNTHESIS EXAMPLE 18

Val-OBzl→D-Leu-Val-OBzl

To L-valine benzyl ester·p-toluenesulfonate (4.56 g) were added ethyl acetate (100 ml) and 5% aqueous sodium hydrogencarbonate (50 ml), the mixture was vigorously stirred and then allowed to stand. The separated ethyl acetate layer was dried over anhydrous sodium sulfate. After the solvent was removed in vacuo, Fmoc-D-leucine (4.24 g) and HOBt·monohydrate (1.78 g) were added and dissolved in dichloromethane (40 ml). To this solution was added under ice-cooling WSCI (3.46 g). The solution was stirred under ice-cooling for one hour, allowed to gradually rise up to room temperature and then stirred overnight. The reaction solution was diluted with chloroform (80 ml) and washed with saturated aqueous sodium chloride and then dried over anhydrous sodium sulfate. After the solvent was removed in vacuo, the resulting residue was dissolved in DMF (50 ml) and diethylamine (8 ml) was added thereto. The mixture was stirred at room temperature for 3 hours. After the solvent was removed in vacuo, purification was carried out by using a silica gel column chromatography (silica gel 75 g, chloroform:methanol=100:0–2) to afford 3.27 g of the dipeptide (2).

(NMR Data for the Dipeptide (2))
$^{1}$H-NMR (δ ppm, CD$_{3}$OD) 7.29–7.39 (5H, m), 5.20 (1H, d, J=12.2 Hz), 5.14 (1H, d, J=12.2 Hz), 4.35 (1H, d, J=5.9 Hz), 3.42 (1H, dd, J=6.4, 7.8 Hz), 2.13–2.22 (1H, m), 1.63–1.73 (1H, m), 1.49–1.55 (1H, m), 1.33–1.40 (1H, m), 0.91–0.95 (12H, m)

SYNTHESIS EXAMPLE 19

D-Leu-Val-OBzl→Ala-D-Leu-Val-OBzl

The dipeptide (2) (2.88 g) obtained in Synthesis Example 18, Fmoc-L-alanine (1.97 g) and HOBt·monohydrate (0.89 g) were dissolved in a mixed solvent of DMF (25 ml) and THF (25 ml), and WSCI (1.72 g) was added under ice-cooling. The solution was stirred under ice-cooling for one hour, allowed to gradually rise up to room temperature and then stirred overnight. After the solvent was removed lie in vacua, the residue was dissolved in DMF (20 ml) and diethylamine (3 ml) was added and the mixture was stirred at room temperature for one hour. After the solvent was removed in vacuo, purification was carried out by using a silica gel column chromatography (silica gel 50 g, chloroform:methanol=100:0–2) to afford 1.59 g of the tripeptide (3).

(NMR Data for the Tripeptide (3))
$^{1}$H-NMR (δ ppm, CDCl$_{3}$) 7.57 (1H, d, J=8.3 Hz), 7.30–7.38 (5H, m), 6.86 (1H, d, J=8.3 Hz), 5.18 (1H, d, J=12.2 Hz), 5.11 (1H, d, J12.2 Hz), 4.43–4.52 (2H, m), 3.49 (1H, q, J=6.8 Hz), 2.14–2.25 (1H, m), 1.74–1.80 (1H, m), 1.62–1.70 (1H, m), 1.53–1.60 (1H, m), 1.51 (2H, br), 1.32 (3H, d, J=6.8 Hz), 0.86–0.96 (12H, m)

SYNTHESIS EXAMPLE 20

Ala-D-Leu-Val-OBzl→Fmoc-Gln(Mbh)-Ala-D-Leu-Val-OBzl

To a solution of the tripeptide (3) (1.59 g) obtained in Synthesis Example 19, N-α-Fmoc-N-γ-Mbh-L-glutamine (2.41 g) and HOBt·monohydrate (0.60 g) in DMF (50 ml) was added under ice-cooling WSCI (1.17 g). The mixture was stirred under ice-cooling for one hour, allowed to gradually rise up to room temperature and then stirred overnight. To the reaction solution was added water (100 ml). The insolubles precipitated out were filtered off and dried to afford 3.78 g of the tetrapeptide (3).

(NMR Data for the Tetrapeptide (3))
$^1$H-NMR (δ ppm, d-DMSO) 8.51 (1H, d, J=8.3 Hz), 8.07 (1H, d, J=8.3 Hz), 7.91–7.99 (2H, m), 7.86 (2H, d, J=7.3 Hz), 7.67–7.72 (2H, m), 7.43 (2H, d, J=7.8 Hz), 7.28–7.41 (9H, m), 7.13–7.15 (4H, m), 6.82–6.85 (4H, m), 6.01 (1H, d, J=8.8 Hz), 5.13 (1H, d, J=12.7 Hz), 5.07 (1H, d, J=12.7 Hz), 3.71–4.44 (7H, m), 3.71 (6H, s), 2.26–2.53 (4H, m), 2.02–2.08 (1H, m), 1.45–1.93 (3H, m), 1.21 (3H, d, J=7.3 Hz), 0.80–0.86 (12H, m)

SYNTHESIS EXAMPLE 21

Fmoc-Gln(Mbh)-Ala-D-Leu-Val-OBzl→Fmoc-Gln(Mbh)-Ala-D-Leu-Val

The tetrapeptide (3) (1.45 g) obtained in Synthesis Example 20 was dissolved in a mixed solvent of methanol (70 ml) and DMF (70 ml), 10% palladium carbon (0.5 g) was added and the mixture was stirred under hydrogen atmosphere for one hour. After the palladium carbon was filtered off, the solvent was removed in vacuo to afford 1.76 g of the tetrapeptide (4).

(NMR Data for the Tetrapeptide (4))
$^1$H-NMR (δ ppm, d-DMSO) 8.53 (1H, d, J=8.3 Hz), 7.28–7.97 (12H, m), 7.13–7.16 (4H, m), 6.82–6.86 (4H, m), 6.01 (1H, d, J=8.8 Hz), 4.02–4.43 (7H, m), 3.71 (6H, s), 2.23–2.39 (1H, m), 1.79–2.06 (3H, m), 1.45–1.60 (3H, m), 1.21 (3H, d, J=6.8 Hz), 0.81–0.86 (12H, m)

SYNTHESIS EXAMPLE 22

Val-OBzl→D-Ala-Val-OBzl

To L-valine benzyl ester·p-toluenesulfonate (2.28 g) were added ethyl acetate (100 ml) and 5% aqueous sodium hydrogencarbonate (50 ml), the mixture was vigorously stirred and then allowed to stand. The separated ethyl acetate layer was dried over anhydrous sodium sulfate. After the solvent was removed in vacuo, Fmoc-D-leucine (1.87 g) and HOBt·monohydrate (0.89 g) were added and dissolved in dichloromethane (20 ml). To this solution was added under ice-cooling WSCI (1.73 g). The solution was stirred under ice-cooling for one hour, allowed to gradually rise up to room temperature and then stirred overnight. The reaction solution was diluted with chloroform (30 ml) and washed with saturated aqueous sodium chloride and dried over anhydrous sodium sulfate. After the solvent was removed in vacuo, the residue was dissolved in DMF (30 ml), diethylamine (3 ml) was added and the mixture was stirred at room temperature for one hour. After the solvent was removed in vacuo, purification was carried out by using a silica gel column chromatography (silica gel 50 g, chloroform:methanol=100:0–2) to afford 1.47 g of the dipeptide (3).

(NMR Data for the Dipeptide (3))
$^1$H-NMR (δ ppm, CDCl$_3$) 7.71 (1H, d, J=8.8 Hz), 7.31–7.39 (5H, m), 5.21 (1H, d, J=12.2 Hz), 5.12 (1H, d, J=12.2 Hz), 4.56 (1H, dd, J=4.4, 8.8 Hz), 3.53 (1H, q, J=6.8 Hz), 2.17–2.28 (1H, m), 1.50 (2H, br), 1.33 (1H, d, J=6.8 Hz), 0.93 (3H, d, J=6.8 Hz), 0.88 (3H, d, J=6.8 Hz)

SYNTHESIS EXAMPLE 23

D-Ala-Val-OBzl→Leu-D-Ala-Val-OBzl

To a solution of the dipeptide (3) (1.47 g) obtained in Synthesis Example 22, Fmoc-L-leucine (1.98 g) and HOBt·monohydrate (0.83 g) in DMF (20 ml) was added under ice-cooling WSCI (1.61 g). The mixture was stirred under ice-cooling for one hour, allowed to gradually rise up to room temperature and then stirred overnight. The reaction solution was diluted with ethyl acetate (50 ml) and washed in turn with 5% aqueous sodium hydrogencarbonate, water, 10% aqueous citric acid and water and then dried over anhydrous sodium sulfate. After the solvent was removed in vacuo, the residue was dissolved in DMF (30 ml), diethylamine (3 ml) was added and the mixture was stirred at room temperature for one hour. After the solvent was removed in vacuo, purification was carried out by using a silica gel column chromatography (silica gel 50 g, chloroform–chloroform:methanol:aqueous ammonia=50:1:0.05) to afford 2.11 g of the tripeptide (4).

(NMR Data for the Tripeptide (4))
$^1$H-NMR (δ ppm, CDCl$_3$) 7.66 (1H, d, J=7.3 Hz), 7.30–7.38 (5H, m), 6.90 (1H, d, J=8.3 Hz), 5.19 (1H, d, J=12.7 Hz), 5.10 (1H, d, J=12.7 Hz), 4.49–4.57 (2H, m), 3.37 (1H, dd, J=3.4, 9.8 Hz), 2.14–2.26 (1H, m), 1.40 (1H, d, J=6.8 Hz), 1.29–1.77 (5H, m), 0.85–0.96 (12H, m)

SYNTHESIS EXAMPLE 24

Leu-D-Ala-Val-OBzl→Fmoc-Gln(Mbh)-Leu-D-Ala-Val-OBzl

To a solution of the tripeptide (4) (2.11 g) obtained in Synthesis Example 23, N-α-Fmoc-N-γ-Mbh-L-glutamine (3.20 g) and HOBt·monohydrate (0.80 g) in DMF (25 ml) was added under ice-cooling WSCI (1.55 g). The mixture was stirred under ice-cooling for one hour, allowed to gradually rise up to room temperature and then stirred overnight. To the reaction solution was added water (100 ml). The insolubles thus precipitated out were filtered off and dried to afford 4.38 g of the tetrapeptide (5).

(NMR Data for the Tetrapeptide (5))
$^1$H-NMR (δ ppm, d-DMSO) 8.51 (1H, d, J=8.3 Hz), 7.87–7.99 (3H, m), 7.86 (2H, d, J=7.3 Hz), 7.67–7.69 (2H, m), 7.28–7.44 (10H, m), 7.12–7.15 (4H, m), 6.83–6.85 (4H, m), 6.01 (1H, d, J=8.3 Hz), 5.14 (1H, d, J12.2 Hz), 5.08 (1H, d, J=12.2 Hz), 4.02–4.40 (7H, m), 3.71 (6H, s), 1.46–2.26 (8H, m), 1.19 (3H, d, J=6.8 Hz), 0.80–0.86 (12H, m)

SYNTHESIS EXAMPLE 25

Fmoc-Gln(Mbh)-Leu-D-Ala-Val-OBzl→Fmoc-Gln(Mbh)-Leu-D-Ala-Val

The tetrapeptide (5) (1.45 g) obtained in Synthesis Example 24 was dissolved in a mixed solvent of methanol (100 ml) and DMF (50 ml), 10% palladium carbon (0.50 g)

was added and the mixture was stirred under hydrogen atmosphere for 1.5 hours. After the palladium carbon was filtered off, the solvent was removed in vacuo to afford 2.00 g of the tetrapeptide (6).

(NMR Data for the Tetrapeptide (6))

$^{1}$H-NMR (δ ppm, CD$_3$OD) 7.62–7.78 (4H, m), 7.28–7.39 (4H, m), 7.12–7.15 (4H, m), 6.83–6.86 (4H, m), 6.09 (1H, s), 3.87–4.45 (7H, m), 3.75 (6H, s), 1.33–2.39 (8H, m), 0.85–0.97 (15H, m)

SYNTHESIS EXAMPLE 26

Fmoc-Gln(Mbh)-Leu-D-Leu-Val-OBzl→Fmoc-Gln(Mbh)-Leu-D-1S, Leu-Val

The tetrapeptide (5) (1.01 g) obtained in Synthesis Example 24 was dissolved in a mixed solvent of methanol (80 ml) and DMF (80 ml), 10% palladium carbon (0.55 g) was added and the mixture was stirred under hydrogen atmosphere for 2 hours. After the palladium carbon was filtered off, the solvent was removed in vacuo to afford 1.98 g of the tetrapeptide (7).

(NMR Data for the Tetrapeptide (7))

$^{1}$H-NMR (δ ppm, d-DMSO) 8.55 (1H, d, J=8.8 Hz), 7.28–8.01 (12H, m), 7.13–7.16 (4H, m), 6.82–6.85 (4H, m), 6.01 (1H, d, J=8.8 Hz), 4.02–4.33 (7H, m), 3.71 (6H, s), 2.25–2.29 (2H, m), 1.77–2.05 (3H, m), 1.45–1.60 (6H, m), 0.80–0.88 (18H, m)

SYNTHESIS EXAMPLE 27

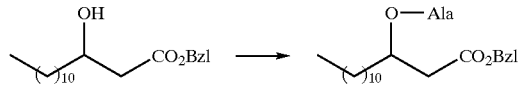

To a solution of benzyl 3-hydroxymyristate (1.67 g), Fmoc-L-alanine-monohydrate (1.65 g) and dimethylaminopyridine (60 mg) in dichloromethane (120 ml) was added under ice-cooling DCC (1.54 g) and the mixture was stirred under ice-cooling for one hour, allowed to gradually rise up to room temperature and then stirred overnight. After the precipitate was filtered off, the dichloromethane was removed in vacuo. To the residue was added ethyl acetate (30 ml), the insolubles were filtered off and then the ethyl acetate was removed in vacuo. The residue was dissolved in DMF (20 ml), diethylamine (2 ml) was added and then the mixture was stirred at room temperature for one hour. After the solvent was removed in vacuo, purification was carried out by using a silica gel column chromatography (silica gel 50 g, chloroform:methanol=200:0–10) to afford 1.70 g of the intermediate compound (10).

(NMR Data for the Intermediate Compound (10))

$^{1}$H-NMR (δ ppm, CDCl$_3$) 7.32–7.36 (5H, m), 5.22–5.29 (1H, m), 5.10–5.11 (2H, m), 3.34–3.44 (1H, m), 2.60–2.63 (2H, m), 1.20–1.59 (25H, m), 0.88 (3H, t, J=7 Hz)

SYNTHESIS EXAMPLE 28

To a solution of the intermediate compound (10) (1.70 g) obtained in Synthesis Example 27, Fmoc-D-leucine (1.48 g)

and HOBt·monohydrate (0.62 g) in dichloromethane (50 ml) was added under ice-cooling WSCI (1.20 g). The mixture was stirred under ice-cooling for one hour, allowed to gradually rise up to room temperature and then stirred overnight. The reaction solution was washed with saturated aqueous sodium chloride and dried over anhydrous sodium sulfate. After the solvent was removed in vacuo, the residue was dissolved in DMF (20 ml), diethylamine (3 ml) was added and the mixture was stirred at room temperature for one hour. After the solvent was removed in vacuo, purification was carried out by using a silica gel column chromatography (silica gel 75 g, chloroform:methanol=200:0–10) to afford 1.93 g of the intermediate compound (11).

(NMR Data for the Intermediate Compound (11))

$^{1}$H-NMR (δ ppm, CDCl$_3$) 7.65 (1H, d, J=7.3 Hz), 7.32–7.38 (5H, m), 5.25–5.31 (1H, m), 5.07–5.14 (2H, m), 4.48–4.53 (1H, m), 3.35–3.38 (1H, m), 2.61–2.71 (2H, m), 1.24–1.74 (28H, m), 0.94 (3H, d, J=11.2 Hz), 0.93 (3H, d, J=11.2 Hz), 0.88 (3H, t, J=6.8 Hz)

SYNTHESIS EXAMPLE 29

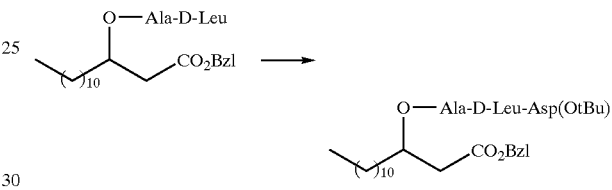

To a solution of the intermediate compound (11) (1.93 g) obtained in Synthesis Example 28, Fmoc-L-aspartic acid β-t-butyl ester (1.53 g) and HOBt·monohydrate (0.55 g) in dichloromethane (100 ml) was added under ice-cooling WSCI (1.07 g). The mixture was stirred under ice-cooling for one hour, allowed to gradually rise up to room temperature and then stirred overnight. The reaction solution was washed with saturated aqueous sodium chloride and dried over anhydrous sodium sulfate. After the solvent was removed in vacuo, the residue was dissolved in DMF (30 ml), diethylamine (3 ml) was added and the mixture was stirred at room temperature for one hour. After the solvent was removed in vacuo, purification was carried out by using a silica gel column chromatography (silica gel 75 g, chloroform:methanol=200:0–10) to afford 2.76 g of the intermediate compound (12).

(NMR Data for the Intermediate Compound (12))

$^{1}$H-NMR (δ ppm, CDCl$_3$) 7.78 (1H, d, J=8.8 Hz), 7.09 (1H, d, J=7.3 Hz), 7.32–7.35 (5H, m), 5.23–5.26 (1H, m), 5.09–5.14 (2H, m), 4.45–4.53 (2H, m), 3.58–3.61 (1H, m), 2.60–2.75 (4H, m), 1.24–1.90 (34H, m), 1.43 (9H, s), 0.88 (3H, t, J=6.8 Hz)

SYNTHESIS EXAMPLE 30

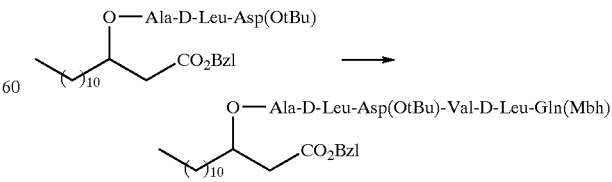

To a solution of the intermediate compound (12) (0.79 g) obtained in Synthesis Example 29, the tetrapeptide (9) (1.08 g) obtained as described in the following Synthesis Example 71 and HOBt·monohydrate (0.17 g) in DMF (25 ml) was added under ice-cooling WSCI (0.33 g). The mixture was stirred under ice-cooling for one hour, allowed to gradually rise up to room temperature and then stirred overnight. The reaction solution was diluted with dichloromethane (100 ml) and washed with saturated aqueous sodium chloride and then dried over anhydrous sodium sulfate. After the solvent was removed in vacuo, the residue was dissolved in DMF (30 ml), diethylamine (3 ml) was added and the mixture was stirred at room temperature for one hour. After the solvent was removed in vacuo, purification was carried out by using a silica gel column chromatography (silica gel 75 g, chloroform:methanol aqueous ammonia=50:1:0.05 to 20:1:0.05) to afford 1.46 g of the intermediate compound (13).

(NMR Data for the Intermediate Compound (13))

$^1$H-NMR (δ ppm, CD$_3$OD) 7.29–7.35 (5H, m), 7.11–7.14 (4H, m), 6.83–6.86 (4H, m), 6.07 (1H, s), 5.21–5.25 (1H, m), 5.11 (2H, s), 4.00–4.64 (7H, m), 3.76 (6H, s), 2.64–2.98 (4H, m), 1.55–2.34 (14H, m), 1.44 (9H, s), 1.25–1.31 (23H, m), 0.87–0.98 (27H, m)

SYNTHESIS EXAMPLE 31

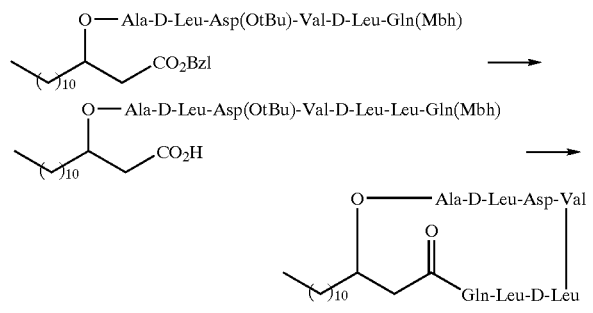

To a solution of the intermediate compound (13) (1.46 g) obtained in Synthesis Example 30 in methanol (150 ml) was added 10% palladium carbon (0.44 g) and the mixture was stirred under hydrogen atmosphere for 30 minutes. The palladium carbon was filtered off and the methanol was removed in vacuo. Then, the residue (0.70 g) was dissolved in a mixed solvent of THF (390 ml) and DMF (130 ml) and then cesium chloride (0.94 g), potassium chloride (0.37 g), N-methylmorpholine (0.11 g), HOBt·monohydrate (0.30 g) and WSCI (0.96 g) were in turn added. The mixture was stirred at room temperature for 5 days. The reaction solution was diluted with ethyl acetate (400 ml) and washed in turn with water, 5% aqueous sodium hydrogencarbonate, water, 10% aqueous citric acid and water and then dried over anhydrous sodium sulfate. After the solvent was removed in vacuo, the residue was applied to a silica gel column (silica gel, 75 g) and the fractions eluted with chloroform:methanol=40:1 (500 ml) were concentrated. The residue (0.91 g) was dissolved in TFA (5 ml) and the solution was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and then purified by a silica gel column chromatography (silica gel 30 g, chloroform methanol=10:1 to 4:1) to afford 0.31 g of the cyclic depsipeptide (3) of the invention (hereinafter referred to as "Compound 5").

(NMR Data for Compound 5)

$^1$H-NMR (δ ppm, d-DMSO) 6.65–9.24 (9H, m), 4.98–5.10 (1H, m), 4.04–4.44 (7H, m), 2.50–2.66 (2H, m), 1.98–2.42 (4H, m), 1.74–1.90 (2H, m), 1.23–1.63 (30H, m), 0.74–0.90 (30H, m)

FAB-MS 979 (MH$^+$), 1017 (MK$^+$)

SYNTHESIS EXAMPLE 32

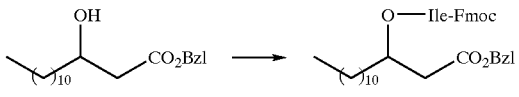

To a solution of benzyl 3-hydroxymyristate (3.18 g), Fmoc-L-isoleucine (3.70 g) and dimethylaminopyridine (0.10 g) in dichloromethane (250 ml) was added under ice-cooling DCC (3.14 g) and the mixture was stirred under ice-cooling for one hour and then allowed to gradually rise up to room temperature and stirred overnight. After a precipitate was filtered off, the dichloromethane was removed in vacuo. To the residue was added ethyl acetate (30 ml), insolubles were filtered off and the ethyl acetate was removed in vacuo. The residue was purified by a silica gel column chromatography (silica gel 200 g, chloroform) to afford 7.14 g of the intermediate compound (14).

(NMR Data for the Intermediate Compound (14))

$^1$H-NMR (δ ppm, CDCl$_3$) 7.29–7.77 (13H, m), 5.27–5.33 (2H, m), 5.11 (2H, s), 4.29–4.34 (3H, m), 4.23 (1H, t, J=6.8 Hz), 2.57–2.72 (2H, m), 1.07–1.90 (23H, m), 0.86–0.95 (9H, m)

SYNTHESIS EXAMPLE 33

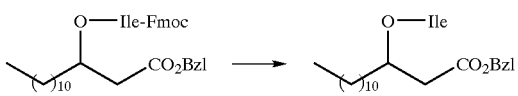

To a solution of the intermediate compound (14) (7.14 g) obtained in Synthesis Example 32 in DMF (70 ml) was added diethylamine (7 ml) and the mixture was stirred at room temperature for 5 hours. After the solvent was removed in vacuo, purification was carried out by a silica gel column chromatography (silica gel 200 g, chloroform methanol=200:0–10) to afford 4.33 g of the intermediate compound (15).

(NMR Data for the Intermediate Compound (15))

$^1$H-NMR (δ ppm, CDCl$_3$) 7.33–7.36 (5H, m), 5.24–5.31 (1H, m), 5.11 (2H, s), 3.19 (1H, d, J=4.9 Hz), 2.57–2.66 (2H, m), 1.05–1.75 (25H, m), 0.86–0.94 (9H, m)

SYNTHESIS EXAMPLE 34

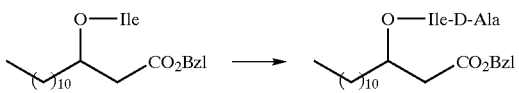

To a solution of the intermediate compound (15) (1.83 g) obtained in Synthesis Example 33, Fmoc-D-alanine (0.91 g) and HOBt·monohydrate (0.40 g) in dichloromethane (70 ml) was added under ice-cooling WSCI (0.77 g) and the mixture was stirred under ice-cooling for 3.5 hours. The reaction solution was washed with a saturated aqueous solution of sodium chloride and dried over anhydrous sodium sulfate. After the solvent was removed in vacuo, the residue was dissolved in DMF (50 ml), diethylamine (4 ml) was added and the mixture was stirred at room temperature for 4 hours.

After the solvent was removed in vacuo, the residue was dissolved in ethyl acetate (100 ml), washed with a saturated aqueous solution of sodium chloride and dried over anhydrous sodium sulfate. After the solvent was removed in vacuo, the residue was purified by a silica gel column chromatography (silica gel 100 g, chloroform methanol:aqueous ammonia=40:1:0.05) to afford 1.77 g of the intermediate compound (16).

(NMR Data for the Intermediate Compound (16))
$^1$H-NMR (δ ppm, CDCl$_3$) 7.66 (1H, d, J=8.B Hz), 7.29–7.38 (5H, m), 5.26–5.31 (1H, m), 5.13 (1H, d, J=12.2 Hz), 5.08 (1H, d, J=12.2 Hz), 4.49–4.54 (1H, m), 3.48–3.53 (1H, m), 2.56–2.72 (2H, m), 1.04–1.95 (25H, m), 0.86–0.93 (12H, m)

SYNTHESIS EXAMPLE 35

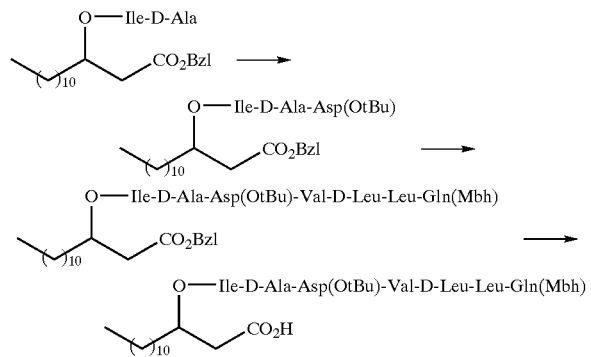

To a solution of the intermediate compound (16) (1.77 g) obtained in Synthesis Example 34, Fmoc-L-aspartic acid β-t-butyl ester (1.21 g) and HOBt·monohydrate (0.40 g) in dichloromethane (100 ml) was added under ice-cooling WSCI (0.77 g) and the mixture was stirred under ice-cooling for 5.5 hours. The reaction solution was washed with a saturated aqueous solution of sodium chloride and dried over anhydrous sodium sulfate. After the solvent was removed in vacuo, the residue was dissolved in DMF (30 ml), diethylamine (3 ml) was added and the mixture was stirred at room temperature for 2 hours. After the solvent was removed in vacuo, the residue was purified by a silica gel chromatography (silica gel 100 g, chloroform:methanol:aqueous ammonia=40:1:0.05) to afford 2.33 g of the intermediate compound (17). To a solution of this intermediate compound (17) (0.77 g), the tetrapeptide (9) (1.46 g) obtained in the following Synthesis Example 71 and HOBt·monohydrate (0.15 g) in DMF (50 ml) was added under ice-cooling WSCI (0.29 g) and the mixture was stirred under ice-cooling for one hour, allowed to gradually rise up to a room temperature and stirred overnight. The reaction solution was diluted with ethyl acetate (200 ml), washed in turn with water, 10% aqueous citric acid, water and 5% aqueous sodium hydrogencarbonate and then dried over anhydrous sodium sulfate. After the solvent was removed in vacuo, the residue was dissolved in DMF (40 ml), diethylamine (1 ml) was added and the mixture was stirred at room temperature for one hour. After the solvent was removed in vacuo, the residue was purified by a silica gel column chromatography (silica gel 100 g, chloroform:methanol:aqueous ammonia=50:1:0.1 to 20:1:0.1) to afford 0.73 g of the intermediate compound (18). The intermediate compound (18) (0.73 g) was dissolved in methanol (100 ml), 10% palladium carbon (0.27 g) was added and the mixture was stirred under hydrogen atmosphere for one hour. The palladium carbon was filtered off and the methanol was removed in vacuo to afford 0.65 g of the intermediate compound (19).

(NMR Data for the Intermediate Compound (19))
$^1$H-NMR (δ ppm, CDCl$_3$) 6.65–8.20 (1SH, m), 6.11 (1H, d, J=6.3 Hz), 5.26–5.30 (1H, m), 3.93–4.53 (6H, m), 3.76 (6H, s), 1.10–3.03 (40H, m), 0.86–0.94 (30H, m)

SYNTHESIS EXAMPLE 36

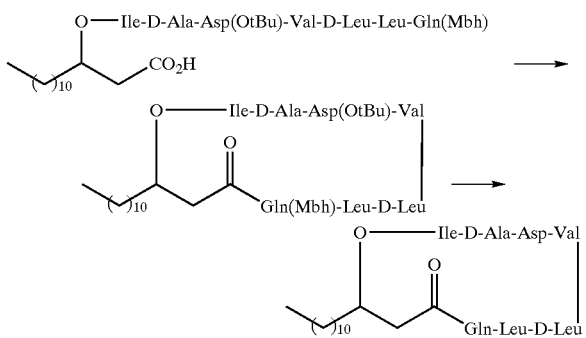

The intermediate compound (19) (0.65 g) obtained in Synthesis Example 35 was dissolved in a mixed solvent of THF (390 ml) and DMF (130 ml) and then cesium chloride (0.94 g), potassium chloride (0.37 g), N-methyl-morpholine (0.11 g), HOBt·monohydrate (0.30 g) and WSCI (0.96 g) were in turn added. The mixture was stirred at room temperature for 5 days. The reaction solution was diluted with ethyl acetate (400 ml) and washed in turn with water, 5% aqueous sodium hydrogencarbonate, water, 10% aqueous citric acid and water and then dried over anhydrous sodium sulfate. After the solvent was removed in vacuo, the residue was applied to a silica gel column (silica gel, 100 g) and the fractions eluted with chloroform:methanol=20:1 (500 ml) were concentrated. The residue (1.05 g) was dissolved in TFA (5 ml) and the solution was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and then purified by a silica gel column chromatography (silica gel 30 g, chloroform:methanol=10:1 to 4:1) to afford 0.24 g of the cyclic depsipeptide (4) of the invention.

(NMR Data for the Cyclic Depsipeptide (4))
$^1$H-NMR (δ ppm, d-DMSO) 6.63–9.86 (9H, m), 4.94–5.14 (1H, 25 m), 3.72–4.55 (7H, m), 1.04–2.66 (38H, m), 0.74–0.91 (30H, m)
FAB-MS 979 (MH$^+$)$^,$ 1017 (MK$^+$)

SYNTHESIS EXAMPLE 37

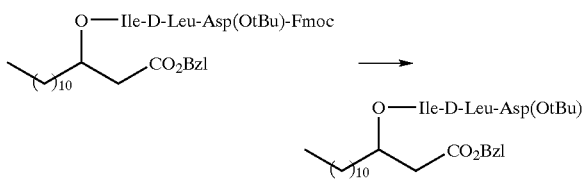

To a solution of the intermediate compound (4) (8.37 g) obtained in Synthesis Example 5 in DMF (80 ml) was added diethylamine (8 ml) and the mixture was stirred at room temperature for 1.5 hours. After the solvent was removed in vacuo, the residue was dissolved in ethyl acetate (150 ml), washed with a saturated aqueous solution of sodium sulfate and dried over anhydrous sodium sulfate. After the solvent was removed in vacuo, purification was carried out by a silica gel column chromatography (silica gel 200 g, chloroform:methanol=30:0–1) to afford 5.81 g of the intermediate compound (20).

(NMR Data for the Intermediate Compound (20))

$^1$H-NMR (δ ppm, CDCl$_3$) 7.28–7.37 (6H, m), 6.88 (1H, d, J=6.9 Hz), 5.23–5.28 (1H, m), 5.06–5.13 (2H, m), 4.45–4.83 (2H, m), 3.62–3.66 (1H, m), 2.55–2.85 (4H, m), 1.24–1.94 (37H, m), 0.85–1.07 (15H, m)

SYNTHESIS EXAMPLE 38

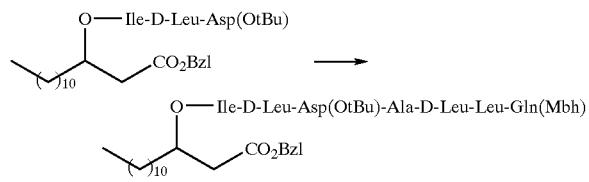

To a solution of the intermediate compound (20) (1.12 g) obtained in Synthesis Example 37, the tetrapeptide (2) obtained in Synthesis Example 17 (1.43 g) and HOBt·monohydrate (0.44 g) in DMF (50 ml) was added under ice-cooling WSCI (0.44 g) and the mixture was stirred under ice-cooling for one hour, allowed to gradually rise up to room temperature and stirred overnight. The reaction solution was diluted with chloroform (200 ml), washed in turn with 10% aqueous citric acid, water, 5% aqueous sodium hydrogencarbonate and water and then dried over anhydrous sodium sulfate. After the solvent was removed in vacuo, the residue was dissolved in DMF (15 ml), diethylamine (0.7 ml) was added and the mixture was stirred at room temperature for one hour. After the solvent was removed in vacuo, the residue was purified by a silica gel column chromatography (silica gel 75 g, chloroform:methanol=100: 1–5) to afford 0.94 g of the intermediate compound (21).

(NMR Data for the Intermediate Compound (21))

$^1$H-NMR (δ ppm, CDCl$_3$) 6.35–7.80 (20H, m), 6.28 (1H, d, J=8.3 Hz), 5.20–5.24 (1H, m), 5.06–5.11 (2H, m), 3.90–4.65 (6H, m), 3.78 (3H, s), 3.77 (3H, s), 3.18–3.22 (1H, m), 2.22–2.65 (8H, m), 1.21–1.95 (43H, m), 0.79–0.97 (30H, m)

SYNTHESIS EXAMPLE 39

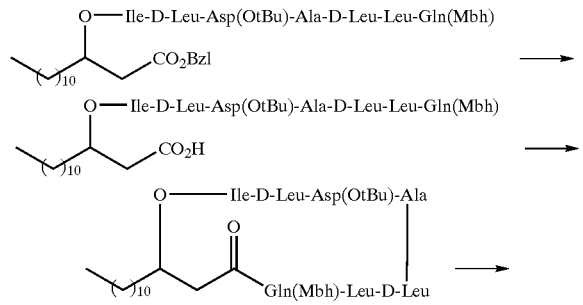

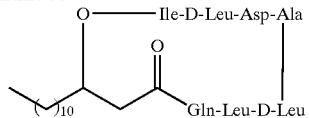

To a solution of the intermediate compound (21) (0.93 g) obtained in Synthesis Example 38 in methanol (150 ml) was added 10% palladium carbon (0.31 g) and the mixture was stirred under hydrogen atmosphere for one hour. The palladium carbon was filtered off and the methanol was removed in vacuo to afford 0.77 g of the intermediate compound (22). Then, the intermediate compound (22) (0.50 g) was dissolved in THF (95 ml) and N-methylmorpholine (0.08 g) and HOBt·monohydrate (0.25 g) were added to form Solution A. In a mixed solvent of THF (190 ml) and DMF (95 ml) were added in turn cesium chloride (0.70 g), potassium chloride (0.28 g) and WSCI (0.71 g) to form Solution B. Solution A was added dropwise to Solution B over 20 minutes while stirring at room temperature and the mixture was stirred at room temperature for 5 days. The reaction solution was diluted with ethyl acetate (200 ml) and washed in turn with water, 5% aqueous sodium hydrogencarbonate, water, 10% aqueous citric acid and water and then dried over anhydrous sodium sulfate. After the solvent was removed in vacuo, the residue was applied to a silica gel column (silica gel, 100 g) and the fractions eluted with chloroform:methanol=50:1 (500 ml) were concentrated. The residue (0.79 g) was dissolved in TFA (3 ml) and the solution was stirred at room temperature for 1.5 hours. After the solvent was removed in vacuo, the residue was neutralized with 5% aqueous sodium hydrogencarbonate and extracted with a 10% methanolic solution of chloroform. The organic layer was dried over anhydrous sodium sulfate and then purified by a silica gel column chromatography (silica gel 30 g, chloroform:methanol=10:1 to 4:1) to afford 0.21 g of the cyclic depsipeptide (5) of the invention.

(NMR Data for the Cyclic Depsipeptide (5))

$^1$H-NMR (δ ppm, d-DMSO) 6.63–9.74 (9H, m), 4.92–5.11 (1H, m), 3.81–4.56 (7H, m), 1.75–2.69 (8H, m), 1.21–1.57 (32H, m), 0.77–0.87 (30H, m)

FAB-MS 993 (MH$^+$), 1031 (MK$^+$)

SYNTHESIS EXAMPLE 40

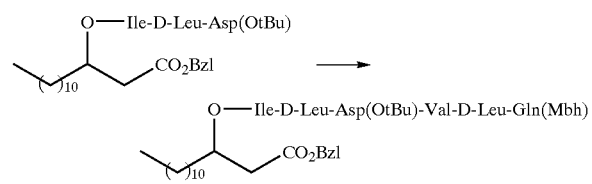

To a solution of the intermediate compound (20) (1.55 g) obtained in Synthesis Example 37, the tetrapeptide (6) obtained in Synthesis Example 25 (2.00 g) and HOBt·monohydrate (0.22 g) in DMF (40 ml) was added under ice-cooling WSCI (0.43 g) and the mixture was stirred under ice-cooling for one hour, allowed to gradually rise up to room temperature and stirred overnight. The reaction solution was diluted with chloroform (200 ml), washed with a saturated aqueous solution of sodium chloride and then dried over anhydrous sodium sulfate. After the solvent was removed in vacuo, the residue was dissolved in DMF (50 ml), diethylamine (3 ml) was added and the mixture was stirred at room temperature for one hour. After the solvent was removed in vacuo, the residue was purified by a silica gel column chromatography (silica gel 75 g, chloroform–chloroform:methanol:aqueous ammonia=50:1:0.1 to 20:1:0.1) to afford 1.21 g of the intermediate compound (23).

(NMR Data for the Intermediate Compound (23))

$^1$H-NMR (δ ppm, CDCl$_3$) 6.60–7.68 (20H, m), 6.12 (1H, d, J=8.4 Hz), 5.20–5.24 (1H, m), 5.06–5.11 (2H, m), 3.85–4.48 (6H, m), 3.79 (6H, s), 3.32–3.36 (1H, m), 2.25–2.52 (8H, m), 1.25–2.06 (41H, m), 0.86–0.99 (30H, m)

SYNTHESIS EXAMPLE 41

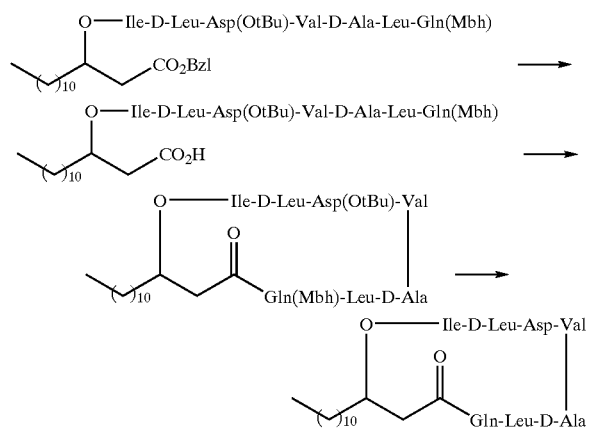

To a solution of the intermediate compound (23) (1.21 g) obtained in Synthesis Example 40 in methanol (100 ml) was added 10% palladium carbon (0.33 g) and the mixture was stirred under hydrogen atmosphere for one hour. The palladium carbon was filtered off and the methanol was removed in vacuo to afford 0.88 g of the intermediate compound (24). Then, the intermediate compound (24) (0.65 g) was dissolved in a mixed solvent of THF (390 ml) and DMF (130 ml), and to the solution were added in turn cesium chloride (0.94 g), potassium chloride (0.37 g), N-methylmorpholine (0.11 g), HOBt·monohydrate (0.30 g) and WSCI (0.96 g) and the mixture was stirred at room temperature for 5 days. The reaction solution was diluted with ethyl acetate (400 ml) and washed in turn with water, 5% aqueous sodium hydrogencarbonate, water, 10% aqueous citric acid and water and then dried over anhydrous sodium sulfate. After the solvent was removed in vacuo, the residue was applied to a silica gel column (silica gel, 75 g) and the fractions eluted with chloroform:methanol=40:1 (500 ml) were concentrated. The residue (1.01 g) was dissolved in TFA (5 ml) and the solution was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and then purified by a silica gel column chromatography (silica gel 30 g, chloroform:methanol=10:0–3) to afford 0.40 g of the cyclic depsipeptide (6) of the invention.

(NMR Data for the Cyclic Depsipeptide (6))

$^1$H-NMR (δ ppm, d-DMSO) 6.63–10.01 (9H, m), 4.93–5.11 (1H, m), 3.99–4.60 (7H, m), 2.61–2.78 (2H, m), 2.00–2.34 (4H, m), 1.80–1.98 (2H, m), 1.16–1.76 (30H, m), 0.76–0.91 (30H, m)

FAB-MS 979 (MH$^+$), 1017 (MK$^+$)

SYNTHESIS EXAMPLE 42

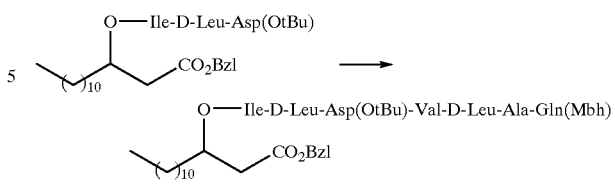

To a solution of the intermediate compound (20) (1.10 g) obtained in Synthesis Example 37, the tetrapeptide (4) obtained in Synthesis Example 21 (1.76 g) and HOBt·monohydrate (0.22 g) in DMF (25 ml) was added under ice-cooling WSCI (0.43 g) and the mixture was stirred under ice-cooling for one hour, allowed to gradually rise up to room temperature and stirred overnight. The reaction solution was diluted with chloroform (200 ml), washed with a saturated aqueous solution of sodium chloride and then dried over anhydrous sodium sulfate. After the solvent was removed in vacuo, the residue was dissolved in DMF (50 ml), diethylamine (3 ml) was added and the mixture was stirred at room temperature for one hour. After the solvent was removed in vacuo, the residue was purified by a silica gel column chromatography (silica gel 75 g, chloroform–chloroform:methanol:aqueous ammonia=50:1:0.1) to afford 1.22 g of the intermediate compound (25).

(NMR Data for the Intermediate Compound (25))

$^1$H-NMR (δ ppm, CDCl$_3$) 8.28–8.31 (1H, m), 6.74–7.50 (19H, m), 6.18 (1H, d, J=8.3 Hz), 5.19–5.24 (1H, m), 5.09 (2H, s), 4.37–4.49 (4H, m), 3.93–4.06 (2H, m), 3.28–3.31 (1H, m), 3.02–3.10 (1H, m), 2.55–2.71 (4H, m), 2.18–2.46 (3H, m), 1.10–2.10 (41H, m), 0.83–0.97 (30H, m)

SYNTHESIS EXAMPLE 43

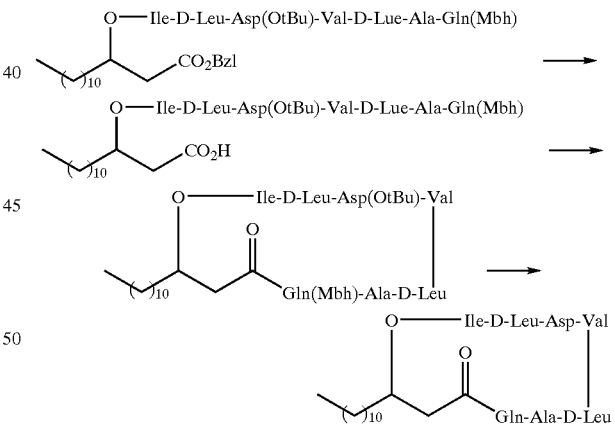

To a solution of the intermediate compound (25) (1.22 g) obtained in Synthesis Example 42 in methanol (150 ml) was added 10% palladium carbon (0.18 g) and the mixture was stirred under hydrogen atmosphere for one hour. The palladium carbon was filtered off and the methanol was removed in vacuo to afford 1.00 g of the intermediate compound (26). Then, the intermediate compound (26) (0.70 g) was dissolved in a mixed solvent of THF (390 ml) and DMF (130 ml), and to the solution were added in turn cesium chloride (0.94 g), potassium chloride (0.37 g), N-methylmorpholine (0.11 g), HOBt·monohydrate (0.30 g) and WSCI (0.96 g) and the mixture was stirred at room temperature for 5 days.

The reaction solution was diluted with ethyl acetate (400 ml) and washed in turn with water, aqueous sodium hydrogencarbonate, water, 10% aqueous citric acid and water and then dried over anhydrous sodium sulfate. After the solvent was removed in vacuo, the residue was applied to a silica gel column (silica gel, 75 g) and the fractions eluted with chloroform:methanol=40:1 (500 ml) were concentrated. The residue (1.10 g) was dissolved in TFA (5 ml) and the solution was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and then purified by a silica gel column chromatography (silica gel 30 g, chloroform methanol=10:0–3) to afford 0.38 g of the cyclic depsipeptide (7).

(NMR Data for the Cyclic Depsipeptide (7))

$^1$H-NMR (δ ppm, d-DMSO) 6.65–9.20 (9H, m), 4.95–5.09 (1H, m), 3.85–4.53 (7H, m), 2.61–2.66 (1H, m), 2.34–2.37 (1H, m), 25 1.75–2.12 (6H, m), 1.18–1.56 (30H, m), 0.78–0.88 (30H, m)

FAB-MS 979 (MH$^+$), 1017 (MK$^+$)

SYNTHESIS EXAMPLE 44

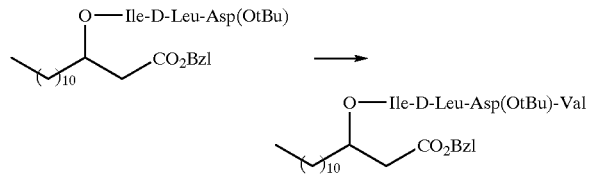

To a solution of the intermediate compound (20) (4.15 g) obtained in Synthesis Example 37, Fmoc-L-valine (1.85 g) and HOBt·monohydrate (0.81 g) in dichloromethane (50 ml) was added under ice-cooling WSCI (1.56 g) and the mixture was stirred under ice-cooling for one hour and then allowed to gradually rise up to room temperature and stirred overnight. The reaction solution was washed with a saturated aqueous solution of sodium chloride and dried over anhydrous sodium sulfate. After the solvent was removed in vacuo, the residue was dissolved in DMF (30 ml), diethylamine (3 ml) was added and the mixture was stirred at room temperature for 2 hours. The solvent was removed in vacuo and the residue was purified by a silica gel column chromatography (silica gel 100 g, chloroform–chloroform methanol=40:1) to afford 2.74 g of the intermediate compound (27).

(NMR Data for the Intermediate Compound (27))

$^1$H-NMR (δ ppm, CDCl$_3$) 8.30 (1H, t, J=8.8 Hz), 7.30–7.37 (5H, m), 7.08 (1H, t, J=7.3 Hz), 6.75 (1H, d, J=8.3 Hz), 5.21–5.24 (1H, m), 5.11 (2H; s), 4.76–4.79 (1H, m), 4.44–4.50 (2H, m), 3.32–3.35 (1H, m), 2.55–2.71 (4H, m), 2.23–2.26 (1H, m), 1.04–1.81 (28H, m), 0.82–0.99 (21H, m)

SYNTHESIS EXAMPLE 45

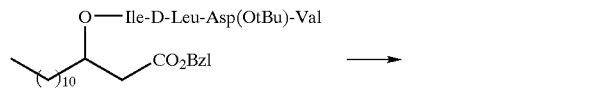

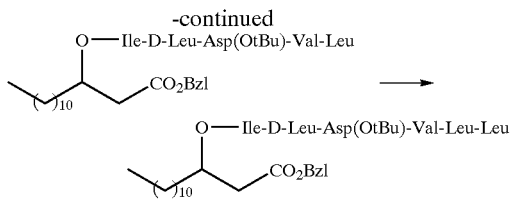

To a solution of the intermediate compound (27) (2.74 g) obtained in Synthesis Example 44, Fmoc-L-leucine (1.16 g) and HOBt·monohydrate (0.49 g) in dichloromethane (50 ml) was added under ice-cooling WSCI (0.95 g) and the mixture was stirred under ice-cooling for one hour, allowed to gradually rise up to room temperature and stirred overnight. The reaction solution was washed with a saturated aqueous solution of sodium chloride and then dried over anhydrous sodium sulfate. After the solvent was removed in vacuo, the residue was dissolved in DMF (30 ml), diethylamine (3 ml) was added and the mixture was stirred at room temperature for 4 hours. The solvent was removed in vacuo, Fmoc-L-leucine (1.16 g) and HOBt·monohydrate (0.49 g) were added to the resulting residue, the mixture was dissolved in dichloromethane (50 ml) and WSCI (0.95 g) was added under ice-cooling. The mixture was stirred under ice-cooling for one hour, allowed to gradually rise up to room temperature and stirred overnight. The reaction solution was washed with a saturated aqueous solution of sodium chloride and then dried over anhydrous sodium sulfate. The residue was dissolved in DMF (30 ml), diethylamine (3 ml) was added and the mixture was stirred at room temperature for one hour. After the solvent was removed in vacuo, the residue was purified by a silica gel column chromatography (silica gel 75 g, chloroform–chloroform:methanol=40:1) to afford 2.15 g of the intermediate compound (28).

(NMR Data for the Intermediate Compound (28))

$^1$H-NMR (δ ppm, CDCl$_3$) 6.85–7.90 (10H, m), 5.20–5.25 (1H, m), 5.07–5.13 (2H, m), 4.05–4.78 (5H, m), 3.28–3.40 (1H, m), 2.59–2.87 (4H, m), 1.23–2.21 (44H, m), 0.84–0.96 (33H, m)

SYNTHESIS EXAMPLE 46

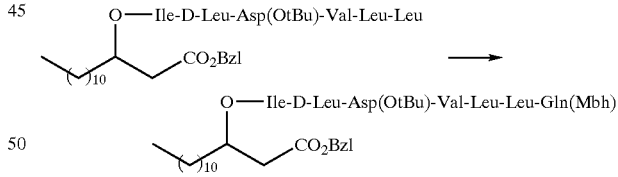

To a solution of the intermediate compound (28) (2.15 g) obtained in Synthesis Example 45, N-α-Fmoc-N-γ-Mbh-L-glutamine (1.21 g) and HOBt·monohydrate (0.30 g) in a mixed solvent of dichloromethane (25 ml) and DMF (25 ml) was added under ice-cooling WSCI (0.58 g) and the mixture was stirred under ice-cooling for one hour and then allowed to gradually rise up to room temperature and stirred overnight. The reaction solution was concentrated, the residue was dissolved in DMF (30 ml), diethylamine (5 ml) was added and the mixture was stirred at room temperature for one hour. After the solvent was removed in vacuo, the residue was purified by a silica gel column chromatography (silica gel 150 g, chloroform:methanol=30:0–1) to afford 2.92 g of the intermediate compound (29).

(NMR Data for the Intermediate Compound (29))

$^1$H-NMR (δ ppm, CDCl$_3$) 6.82–7.75 (20H, m), 5.15–5.20 (1H, m), 5.07 (2H, s), 4.05–4.50 (6H, m), 3.78 (3H, s), 3.77 (3H, s), 3.31–3.35 (1H, m)., 2.33–2.80 (8H, m), 1.22–2.08 (44H, m), 0.81–0.94 (33H, m)

SYNTHESIS EXAMPLE 47

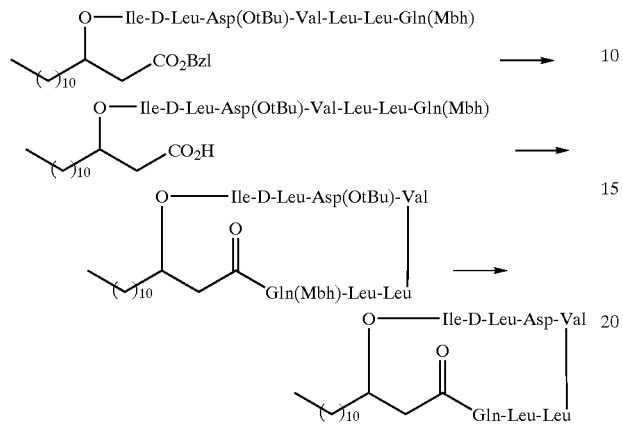

To a solution of the intermediate compound (29) (2.92 g) obtained in Synthesis Example 46 in a mixed solvent of methanol (75 ml) and DMF (50 ml) was added 10% palladium carbon (0.43 g) and the mixture was stirred under hydrogen atmosphere for 1.5 hours. The palladium carbon was filtered off and the solvent was removed in vacuo to afford 2.77 g of the intermediate compound (30). Then, the intermediate compound (30) (2.14 g) was dissolved in a mixed solvent of DMF (390 ml) and THF (1170 ml), and to the solution were added in turn cesium chloride (2.82 g), potassium chloride (1.11 g), N-methylmorpholine (0.33 g), HOBt·monohydrate (0.90 g) and WSCI (2.88 g) and the mixture was stirred at room temperature for 5 days. The reaction solution was concentrated, the residue was dissolved in ethyl acetate (400 ml), washed with water (200 ml) and dried over anhydrous sodium sulfate. After the solvent was removed in vacuo, the residue was purified by a silica gel column (silica gel 75 g, chloroform:ethyl acetate=1:1) to afford 1.04 g of the cyclic depsipeptide (8'). The cyclic depsipeptide (8') (0.54 g) was dissolved in TFA (5 ml) and the solution was stirred at room temperature for 2 hours.

After the solvent was removed in vacuo, the residue was neutralized with 5% aqueous sodium hydrogencarbonate and extracted with a 10% methanolic solution of chloroform. The organic layer was dried over anhydrous sodium sulfate and then purified by a silica gel column chromatography (silica gel 30 g, chloroform:methanol=10:0–2) to afford 0.26 g of the cyclic depsipeptide (8) of the invention (hereinafter referred to as "Compound 6").

(NMR Data for Compound 6)

$^1$H-NMR (d ppm, d-DMSO) 6.64–9.45 (9H, m), 5.04–5.14 (1H, m), 3.74–4.45 (7H, m), 2.32–2.44 (2H, m), 2.05–2.20 (4H, m), 1.70–1.99 (2H, m), 1.23–1.60 (33H, m), 0.82–0.94 (33H, m)

FAB-MS 1021 (MH$^+$), 1059 (MK$^+$)

SYNTHESIS EXAMPLE 48

Fmoc-Asp(OtBu)+Leu-OBzl→Fmoc-Asp(OtBu)-Leu

The dipeptide (6.63 g) was obtained from L-leucine benzyl ester·p-toluenesulfonate (6.00 g) and L-aspartic acid β-t-butyl ester (5.23 g) in the same manner as in Synthesis Example 13. The dipeptide thus obtained was debenzylated in the same manner as in Synthesis Example 17 to afford the desired dipeptide (5.21 g).

$^1$H-NMR (CDCl$_3$) δ ppm: 7.75 (2H, d, J=7.8 Hz), 7.56 (2H, d, J=7.3 Hz), 7.39 (2H, t, J=7.6 Hz), 7.30 (2H, dt, J=1.0, 7.3 Hz), 7.00 (1H, d, J=7.8 Hz), 6.03 (1H, d, J=8.3 Hz), 5.60 (1H, br s), 4.52–4.64 (2H, m), 4.41 (2H, d, J=6.8 Hz), 4.21 (1H, t, J=6.8 Hz), 2.87 (1H, dd, J=4.4, 17 Hz), 2.62 (1H, dd, J=6.8, 17 Hz), 1.66–1.76 (2H, m), 1.55–1.65 (1H, m), 1.44 (9H, s), 0.92 (6H, t, J=5.6 Hz)

SYNTHESIS EXAMPLE 49

Fmoc-Gln(Mbh)-Leu-D-Leu+Val-Asp(OtBu)-D-Leu-OBzl→Fmoc-Gln(Mbh)-Leu-D-Leu-Val-Asp(OtBu)-D-Leu-OBzl To a solution of the tripeptide (9) (0.92 g) obtained in the following Synthesis Example 77, the tripeptide (6) (0.50 g) obtained in the following Synthesis Example 73 and HOBt·monohydrate (0.17 g) in DMF (10 ml) was added under ice-cooling WSCI (0.21 g). The solution was stirred under ice-cooling for 2 hours and then stirred at room temperature overnight. After the DMF was removed in vacuo, to the residue were added a 10% methanolic solution of chloroform and a 10% aqueous solution of citric acid. The separated organic layer was washed in turn with water, 5% aqueous sodium hydrogencarbonate and water and then dried over anhydrous sodium sulfate. After the solvent was removed in vacuo, the residue was purified by a silica gel column chromatography (silica gel 30 g, chloroform:ethyl acetate=100:0 to 85:15) and then solidified with diethyl ether to afford 0.82 g of the desired hexapeptide (1).

$^1$H-NMR (DMSO-d$_6$) δ ppm: 8.53 (1H, d, J=8.3 Hz), 8.09 (1H, d, J=8.3 Hz), 8.05 (1H, d, J=7.3 Hz), 8.01 (1H, d, J=7.8 Hz), 7.86 (2H, d, J=7.3 Hz), 7.80–7.89 (1H, m), 7.64–7.76 (3H, m), 7.46 (1H, d, J=7.8 Hz), 7.39 (2H, t, J=7.3 Hz), 7.24–7.36 (7H, m), 7.13 (4H, d, J=8.8 Hz), 6.83 (4H, dd, J=2.0, 8.8 Hz), 6.00 (1H, d, J=8.8 Hz), 5.09 (2H, s), 4.65 (1H, dd, J=8.3, 14 Hz), 4.11–4.40 (7H, m), 3.98–4.07 (1H, m), 3.71 (3H, s), 3.70 (3H, s), 2.63 (1H, dd, J=5.6, 16 Hz), 2.45–2.51 (1H, m), 2.19–2.34 (2H, m), 1.86–2.00 (2H, m), 1.73–1.85 (1H, m), 1.38–1.64 (9H, m), 1.33 (9H, m), 0.69–0.88 (24H, m)

SYNTHESIS EXAMPLE 50

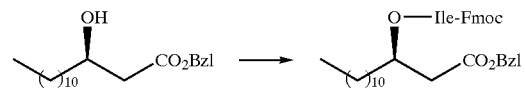

The desired intermediate compound (5.55 g) was obtained using (R)-3-hydroxymyristic acid in the same manner as in Synthesis Example 32 and the alcohol (2.77 g) obtained in the same manner as in Synthesis Example 1.

$^1$H-NMR (CDCl$_3$) δ ppm: 7.76 (2H, d, J=7.3 Hz), 7.59 (2H, d, J=5.4 Hz), 7.39 (2H, t, J=7.3 Hz), 7.26–7.36 (7H, m), 5.24–5.34 (2H, m), 5.10 (2H,), 4.35–4.43 (2H, m), 4.30 (1H, dd, J=4.6, 3.8 Hz), 4.22 (1H, t, J=7.1 Hz), 2.69 (1H, dd, J=7.3, 16 Hz), 2.59 (1H, dd, J5.4, 16 Hz), 1.84–1.94 (1H, m), 1.54–1.69 (2H, m), 1.07–1.45 (20H, m), 0.81–0.97 (9H, m)

SYNTHESIS EXAMPLE 51

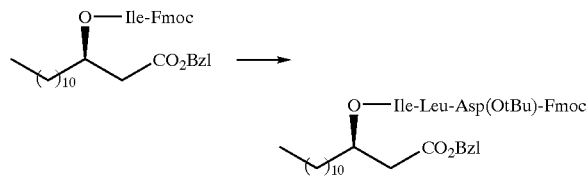

To a solution of the intermediate compound (5.45 g) obtained in Synthesis Example 50 in DMF (80 ml) was added diethylamine (8 ml) and the mixture was stirred at room temperature for 1.5 hours. After the solvent was removed in vacuo, the residue was purified by a silica gel column chromatography (silica gel 50 g, chloroform:methanol=200:0–10) to afford 3.62 g of an amine derivative. To a solution of the amine derivative thus obtained, the dipeptide obtained in Synthesis Example 48 (5.06 g) and HOBt·monohydrate (1.48 g) in dichloromethane (60 ml) was added under ice-cooling WSCI (1.85 g). The solution was stirred under ice-cooling for 2 hours and then at room temperature overnight. After the dichloromethane was removed in vacuo, ethyl acetate and a 10% aqueous solution of citric acid were added to the residue. The separated ethyl acetate layer was washed in turn with water, 5% aqueous sodium hydrogencarbonate and water and then dried over anhydrous sodium sulfate. After the ethyl acetate was removed in vacuo, the residue was purified by a silica gel column chromatography (silica gel 100 g, hexane:ethyl acetate=200: 50–90) and then solidified with a solvent system of diethyl ether-hexane to afford 7.11 g of the desired intermediate compound.

$^1$H-NMR (CDCl$_3$) δ ppm: 7.76 (2H, d, J=7.3 Hz), 7.58 (2H, d, J=7.3 Hz), 7.40 (2H, t, J=7.6 Hz), 7.28–7.37 (7H, m), 6.85 (1H, d, J=8.3 Hz), 6.49 (1H, d, J=8.3 Hz), 5.97 (1H, d, J=8.3 Hz), 5.27 (1H, qui., J=6.2 Hz), 5.12 (1H, d, J=13 Hz), 5.09 (1H, d, J=13 Hz), 4.51 (1H, dd, J=4.4, 8.8 Hz), 4.47–4.56 (1H, m), 4.37–4.46 (3H, m), 4.22 (1H, t, J=6.8 Hz), 2.92 (1H, dd, J=4.4, 17 Hz), 2.68 (1H, dd, J=6.8, 16 Hz), 2.58 (1H, dd, J=5.9, 16 Hz), 2.55–2.67 (1H, m), 1.75–1.88 (1H, m), 1.52–1.73 (5H, m), 1.45 (9H, s), 1.07–1.46 (20H, m), 0.82–0.97 (15H, m)

SYNTHESIS EXAMPLE 52 (1)

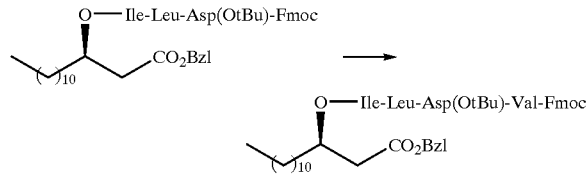

To a solution of the intermediate compound (2.90 g) obtained in Synthesis Example 51 in DMF (30 ml) was added diethylamine (3 ml) and the mixture was stirred at room temperature for 1.5 hours. After the solvent was removed in vacuo, the residue was purified by a silica gel column chromatography (silica gel 30 g, chloroform:methanol=100:0–7) to afford 2.22 g of an amine derivative. To a solution of the amine derivative thus obtained, Fmoc-L-valine (1.24 g) and HOBt·monohydrate (0.56 g) in dichloromethane (25 ml) was added under ice-cooling WSCI (0.70 g). The solution was stirred under ice-cooling for 2 hours and then at room temperature for 2 days. After the dichloromethane was removed in vacuo, chloroform and a 10% aqueous solution of citric acid were added to the residue. The separated chloroform layer was washed in turn with water, 5% aqueous sodium hydrogencarbonate and water and then dried over anhydrous sodium sulfate. After the chloroform was removed in vacuo, the residue was purified by a silica gel column chromatography (silica gel 30 g, chloroform:methanol=100:0–2) to afford 2.29 g of the desired intermediate compound.

$^1$H-NMR (CDCl$_3$) δ ppm: 7.77 (2H, d, J=7.3 Hz), 7.59 (2H, dd, J=.9, 7.3 Hz), 7.40 (2H, t, J=7.3 Hz), 7.28–7.37 (8H, m), 7.05 (1H, d, J=7.8 Hz), 6.59 (1H, d, J=7.8 Hz), 5.30 (1H, d, J=7.3 Hz), 5.26 (1H, qui., J=6.3 Hz), 5.12 (1H, d, J=14 Hz), 5.09 (1H, d, J=12 Hz), 4.68–4.75 (1H, m), 4.45–4.52 (2H, m), 4.35–4.44 (2H, m), 4.23 (1H, t, J=6.8 Hz), 4.00 (1H, t, J=5.6 Hz), 2.92 (1H, dd, J=3.7, 17 Hz), 2.70 (1H, dd, J=6.8, 16 Hz), 2.59 (1H, dd, J=6.6, 17 Hz), 2.58 (1H, dd, J=6.6, 17 Hz), 2.13–2.23 (1H, m), 1.85–1.94 (1H, m), 1.48–1.76 (5H, m), 1.41 (9H, s), 1.09–1.45 (20H, m), 0.99 (3H, d, J=6.8 Hz), 0.95 (3H, d, J=6.4 Hz), 25 0.80–0.92 (15H, m)

SYNTHESIS EXAMPLE 52 (2)

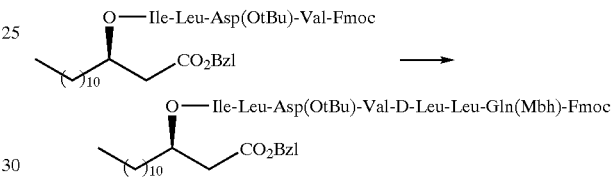

To a solution of the intermediate compound (1.58 g) obtained in Synthesis Example 52 (1) in DMF (15 ml) was added diethylamine (1.5 ml) and the mixture was stirred at room temperature for 1.5 hours. After the solvent was removed in vacuo, the residue was purified by a silica gel column chromatography (silica gel 25 g, chloroform methanol=100:0–8) to afford 1.09 g of an amine derivative. To a solution of the amine derivative thus obtained, the tripeptide (9) (1.29 g) obtained in the following Synthesis Example 77 and HOBt·monohydrate (0.24 g) in DMF (20 ml) was added under ice-cooling WSCI (0.30 g). The solution was stirred under ice-cooling for 2 hours and then at room temperature overnight. After the solvent was removed in vacuo, chloroform and a 10% aqueous solution of citric acid were added to the residue. The separated chloroform layer was washed in turn with water, 5% aqueous sodium hydrogencarbonate and water and then dried over anhydrous sodium sulfate. After the chloroform was removed in vacuo, the residue was purified by a silica gel column chromatography (silica gel 50 g, chloroform:methanol=200:0–6) to afford 1.91 g of the desired intermediate compound.

$^1$H-NMR (CDCl$_3$) δ ppm: 7.73 (2H, d, J=7.3 Hz), 7.63 (1H, d, J=8.3 Hz), 7.59 (1H, d, J=8.8 Hz), 7.55 (2H, d, J=7.3 Hz), 7.38 (2H, t, J=7.6 Hz), 7.20–7.35 (8H, m), 7.18 (2H, d, J=8.3 Hz), 7.14 (2H, d, J=8.8 Hz), 6.84 (4H, dd, J=4.2, 8.3 Hz), 6.60–7.10 (4H, m), 6.40 (1H, d, J=B.3 Hz), 6.24 (1H, d, J=8.3 Hz), 5.18 (1H, qui., J=6.3 Hz), 5.07 (2H, s), 4.78–4.85 (1H, m), 4.45–4.55 (2H, m), 4.25–4.44 (4H, m), 4.10–4.20 (3H, m), 3.77 (3H, s), 3.74 (3H, s), 2.89 (1H, dd, J=7.3, 16 Hz), 2.71 (1H, dd, J=5.1, 17 Hz), 2.61 (1H, dd, J=6.8, 16 Hz), 2.51 (1H, dd, J=6.4, 16 Hz), 2.14–2.32 (3H, m), 1.90–2.11 (2H, m), 1.76–1.87 (3H, m), 1.43 (9H, s), 1.05–1.65 (29H, m), 0.95 (3H, d, J=6.3 Hz), 0.79–0.93 (24H, m), 0.76 (3H, d, J=5.4 Hz), 0.74 (3H, d, J=5.9 Hz)

SYNTHESIS EXAMPLE 52 (3)

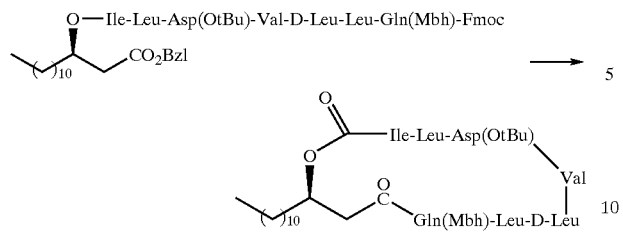

To a solution of the intermediate compound (1.90 g) obtained in Synthesis Example 52 (2) in DMF (15 ml) was added diethylamine (1.5 ml) and the mixture was stirred at room temperature for 1.5 hours. After the solvent was removed in vacuo, purification was carried out by a silica gel column chromatography (silica gel 30 g, chloroform methanol=200:0–7) to afford 1.36 g of an amine derivative.

The amine derivative thus obtained was dissolved in methanol (40 ml), 5% palladium carbon (0.28 g) was added and the mixture was stirred under hydrogen atmosphere for 10 hours. The palladium carbon was filtered off, the methanol was removed in vacuo and then the residue was purified by a silica gel column chromatography (silica gel 30 g, chloroform:methanol=200:0–20) and solidified with a solvent system of chloroform—diethyl ether to afford 0.87 g of a deprotected derivative.

The deprotected derivative thus obtained (0.60 g) was dissolved in THF (100 ml) and N-methylmorpholine (0.10 ml) and HOBt·monohydrate (0.28 g) were added to form Solution A. To a mixed solvent of THF (200 ml) and DMF (100 ml) were added in turn cesium chloride (0.76 g), potassium chloride (0.30 g) and WSCI (0.78 g) to form Solution B. Solution A was added dropwise to Solution B over 20 minutes while stirring at room temperature and then the mixture was further stirred at room temperature for 10 days. The reaction solution was diluted with ethyl acetate (150 ml), washed in turn with water, 5% aqueous sodium hydrogen-carbonate, water, 10% aqueous citric acid and water, and then dried over anhydrous sodium sulfate. After the solvent was removed in vacuo, the residue was purified by a silica gel column chromatography (silica gel 20 g, chloroform methanol=200:0–6) and further purified again by a silica gel column chromatography (silica gel 20 g, chloroform ethyl acetate=100: 10–70) and then solidified using diethyl ether and hexane to afford 0.40 g of the cyclic depsipeptide (9) of the invention.

(Data for the Cyclic Depsipeptide (9))

$^1$H-NMR (CDCl$_3$) δ ppm: 7.50 (1H, d, J=7.8 Hz), 7.40 (1H, br s), 7.32 (1H, br s), 7.11–7.28 (4H, m), 7.16 (2H, d, J=8.3 Hz), 7.14 (2H, d, J=7.8 Hz), 6.95 (1H, br s), 6.83 (4H, d, J=7.8 Hz), 6.15 (1H, d, J=7.8 Hz), 5.06–5.13 (1H, m), 4.65–4.73 (1H, m), 4.26–4.37 (3H, m), 4.11–4.26 (2H, m), 4.06 (1H, t, J=6.6 Hz), 3.78 (6H, s), 2.78–2.92 (2H, m), 2.19–2.48 (5H, m), 2.03–2.12 (2H, m), 1.77–1.91 (1H, m), 1.35–1.76 (1H, m), 1.43 (9H, s), 1.07–1.34 (20H, m), 0.81–0.98 (33H, m)

SYNTHESIS EXAMPLE 52 (4)

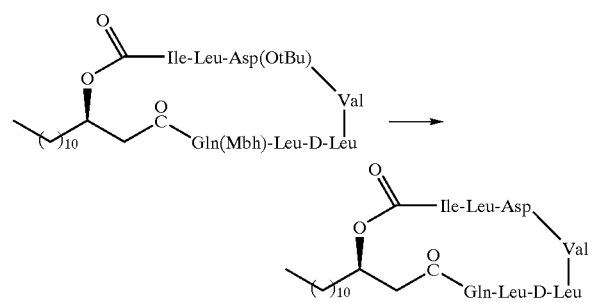

In the same manner as described in Synthesis Example 12, 0.16 g of the cyclic depsipeptide (10) of the invention was obtained from the intermediate compound (0.30 g) obtained in Synthesis Example 52 (3).

(Data for the Cyclic Depsipeptide (10))

$^1$H-NMR (DMSO-d$_6$) δ ppm: 12.28 (1H, s), 8.72 (1H, d, J=5.4 Hz), 8.27 (1H, d, J=9.8 Hz), 8.16 (1H, d, J=7.8 Hz), 8.07 (1H, d, J=8.3 Hz), 7.92 (1H, d, J=5.9 Hz), 7.74 (1H, d, J=6.8 Hz), 7.32 (1H, d, J=9.3 Hz), 7.19 (1H, s), 6.64 (1H, s), 5.19 (1H, qui., J=6.3 Hz), 4.61–4.69 (1H, m), 4.20–4.38 (3H, m), 4.06–4.16 (3H, m), 2.90–2.98 (1H, m), 2.60–2.70 (1H, m), 1.90–2.40 (5H, m), 1.60–1.80 (3H, m), 1.00–1.60 (31H, m), 0.70–0.95 (33H, m)

SYNTHESIS EXAMPLE 53

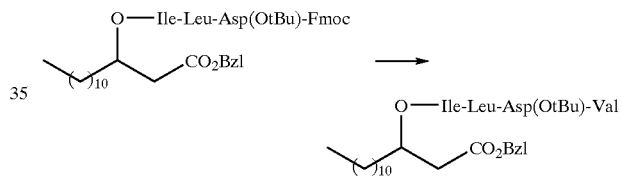

To a solution of the intermediate compound (32) (2.50 g), which had been prepared by deprotecting in the same manner as described in Synthesis Example 57 the intermediate compound obtained, starting from the benzyl 3-hydroxymyristate of Synthesis Example 1, in the same manner as described in Synthesis Examples 50 and 51, Fmoc-L-valine (1.16 g) and HOBt.monohydrate (0.50 g) in dichloromethane (100 ml) was added under ice-cooling WSCI (0.98 g), the mixture was stirred under ice-cooling for one hour and then allowed to gradually rise up to room temperature and stirred for 3 hours. The reaction solution was washed with a saturated aqueous solution of sodium chloride and dried over anhydrous sodium sulfate. After the solvent was removed in vacuo, the residue was dissolved in DMF (50 ml), diethylamine (3 ml) was added and the mixture was stirred at room temperature for one hour. After the solvent was removed in vacuo, purification was carried out by a silica gel column chromatography (silica gel 75 g, chloroform—chloroform : methanol=50:1) to afford 2.86 g of the intermediate compound (35) (SEQ ID NO 1).

(NMR Data for the Intermediate Compound (35))

$^1$H-NMR (δ ppm, CDCl$_3$) 8.26 (1H, d, J=8.3 Hz), 6.97 (1H, d, J=7.8 Hz), 6.97 (1H, d, J=7.3 Hz), 7.32–7.38 (5H, m), 5.24–5.29 (1H, m), 5.11 (2H, s), 4.72–4.77 (1H, m), 4.46–4.51 (1H, m), 4.36–4.41 (1H, m), 3.27 (1H, d, J=3.9 Hz), 2.55–2.71 (4H, m), 2.24–2.32 (1H, m), 1.44 (9H, s), 1.03–1.91 (28H, m), 0.81–1.00 (21H, m)

SYNTHESIS EXAMPLE 54

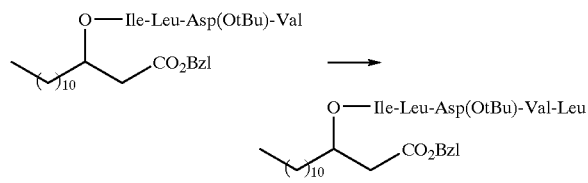

To a solution of the intermediate compound (35) (2.86 g) obtained in Synthesis Example 53, Fmoc-L-leucine (1.20 g) and HOBt.monohydrate (0.50 g) in dichloromethane (100 ml) was added under ice-cooling WSCI (0.98 g), the mixture was stirred under ice-cooling for one hour and then allowed to gradually rise up to room temperature and stirred overnight. The reaction solution was washed with a saturated aqueous solution of sodium chloride and dried over anhydrous sodium sulfate. After the solvent was removed in vacuo, the residue was dissolved in DMF (50 ml), diethylamine (3 ml) was added and the mixture was stirred at room temperature for 1.5 hours. After the solvent was removed in vacuo, purification was carried out by a silica gel column chromatography (silica gel 100 g, chloroform—chloroform: methanol=40:1 to 20:1) to afford 2.99 g of the intermediate compound (36) (SEQ ID NO 2).

(NMR Data for the Intermediate Compound (36))
$^1$H-NMR (6 ppm, CDCl$_3$) 7.98-8.02 (1H, m), 7.53-7.56 (1H, m), 7.22-7.25 (1H, m), 6.74-6.77 (1H, m), 7.31-7.36 (5H, m), 5.23-5.26 (1H, m), 5.10 (2H, s), 4.61-4.67 (1H, m), 5 4.41-4.49 (2H, m), 4.07-4.11 (1H, m), 3.48-3.51 (1H, m), 1.59-2.78 (16H, m), 1.42 (9H, s), 1.24 (bs, 20H), 1.03-1.91 (23H, m), 0.85-1.01 (27H, m)

SYNTHESIS EXAMPLE 55

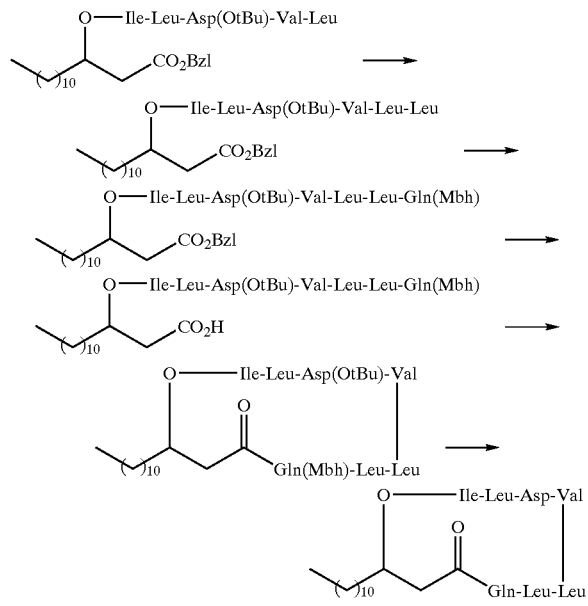

To a solution of the intermediate compound (36) (2.99 g) obtained in Synthesis Example 54, Fmoc-L-leucine (1.12 g) and HOBt.monohydrate (0.47 g) in dichloromethane (50 ml) was added under ice-cooling WSCI (0.91 g), the mixture was stirred under ice-cooling for one hour and then allowed to rise up to room temperature and stirred overnight. The reaction solution was washed with a saturated aqueous solution of sodium chloride and dried over anhydrous sodium sulfate. After the solvent was removed in vacuo, the residue was dissolved in DMF (30 ml), diethylamine (3 ml) was added and the mixture was stirred at room temperature for 2 hours. After the solvent was removed in vacuo, purification was carried out by a silica gel column chromatography (silica gel 75 g, chloroform methanol=20:0–1) to afford 3.46 g of the intermediate compound (37) (SEQ ID NO 3). To a solution of this compound, N-α-Fmoc-N-γ-Mbh-L-glutamine (1.88 g) and HOBt.monohydrate (0.47 g) in DMF (25 ml) was added under ice-cooling WSCI (0.91 g), the mixture was stirred under ice-cooling for one hour and then allowed to rise up to room temperature and stirred overnight. The reaction solution was concentrated and the residue was dissolved in DMF (100 ml), diethylamine (5 ml) was added and the mixture was stirred at room temperature for 2 hours. After the solvent was removed in vacuo, purification was carried out by a silica gel column chromatography (silica gel 150 g, chloroform: methanol=30:0–1) to afford 2.55 g of the intermediate compound (38) (SEQ ID NO 4). This compound was dissolved in a mixed solvent of methanol (50 ml) and DMF (25 ml), 10% palladium carbon (0.33 g) was added and the mixture was stirred under hydrogen atmosphere for one hour. The palladium carbon was filtered off and the solvent was removed in vacuo to afford 2.52 g of the intermediate compound (39). This intermediate compound (39) (SEQ ID NO 5) (2.08 g) was dissolved in a mixed solvent of DMF (390 ml) and THF (1170 ml), and cesium chloride (2.82 g), potassium chloride (1.11 g), N-methylmorpholine (0.33 g), HOBt.monohydrate (0.90 g) and WSCI (2.88 g) were added in turn and the mixture was stirred at room temperature for 5 days. The reaction solution was concentrated, the residue was dissolved in ethyl acetate (400 ml), washed with water (200 ml), and then dried over anhydrous sodium sulfate. After the solvent was removed in vacuo, the residue was purified by a silica gel column chromatography (silica gel 75 g, chloroform: methanol=100:0–1) to afford 1.24 g of the cyclic depsipeptide (11) of the invention (SEQ ID NO 6). A solution of the product in TFA (5 ml) was stirred at room temperature for 2 hours. After the solvent was removed in vacuo, the residue was neutralized with 5% aqueous sodium hydrogencarbonate and extracted with a 10% methanolic solution of chloroform. After the organic layer was dried over anhydrous sodium sulfate, the residue was purified by a silica gel column chromatography (silica gel 50 g, chloroform: methanol=10:0–2) to afford 0.40 g of the cyclic depsipeptide (12) of the invention (hereinafter referred to as "Compound 7") (SEQ ID NO 7).

(NMR Data for Compound 7)
$^1$H-NMR (δ ppm, d-DMSO) 6.64–9.45 (9H, m), 4.93–5.12 (1H, m), 3.96–4.44 (7H, m), 1.90–2.56 (8H, m), 1.10–1.77 (33H, m), 0.75–0.92 (33H, m) FAB-MS 1021 (MH$^+$), 1059 (MK$^+$)

SYNTHESIS EXAMPLE 56

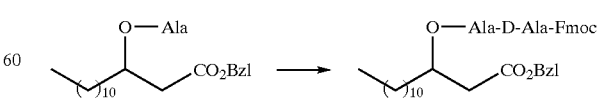

To a solution of the intermediate compound (10) (2.46 g) obtained in Synthesis Example 27, Fmoc-D-alanine (1.89 g) and HOBt.monohydrate (0.90 g) in dichloromethane (50 ml) was added under ice-cooling WSCI (1.74 g), the mixture was stirred under ice-cooling for one hour and then allowed to gradually rise up to room temperature and stirred overnight. After the solvent was removed in vacuo, purification was carried out by a silica gel column chromatography (silica gel 150 g, chloroform) to afford 3.48 g of the intermediate compound (40).

(NMR Data for the Intermediate Compound (40))

$^1$H-NMR (δ ppm, CDCl$_3$) 7.76 (2H, d, J=7.8 Hz), 7.59 (2H, d, J=7.3 Hz), 7.24–7.51 (9H, m), 6.52 (1H, bs), 5.26–5.30. (1H, m), 5.42 (1H, bs), 5.11 (1H, d, J=12.2 Hz), 5.07 (1H, d, J=12.2 Hz), 4.21–4.50 (5H, m), 2.56–2.64 (2H, m), 1.23–1.60 (26H, m), 0.88 (3H, t, J=6.8 Hz)

SYNTHESIS EXAMPLE 57

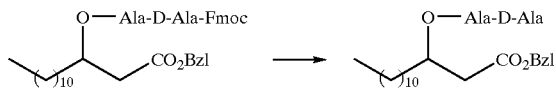

To a solution of the intermediate compound (40) (3.48 g) obtained in Synthesis Example 56 in DMF (30 ml) was added diethylamine (3 ml) and the mixture was stirred at room temperature for one hour. After the solvent was removed in vacuo, purification was carried out by a silica gel column chromatography (silica gel 75 g, chloroform methanol=200:0–10) to afford 1.99 g of the intermediate compound (41).

(NMR Data for the Intermediate Compound (41))

$^1$H-NMR (δ ppm, CDCl$_3$) 7.65 (1H, bs), 7.31–7.38 (5H, m), 5.25–5.32 (1H, m), 5.13 (1H, d, J=12.2 Hz), 5.08 (1H, d, J=12.2 Hz), 4.47–4.54 (1H, m), 3.48 (1H, q, J=6.8 Hz), 2.57–2.70 (2H, m), 1.24–1.60 (28H, m), 0.88 (3H, t, J=6.8 Hz)

SYNTHESIS EXAMPLE 58

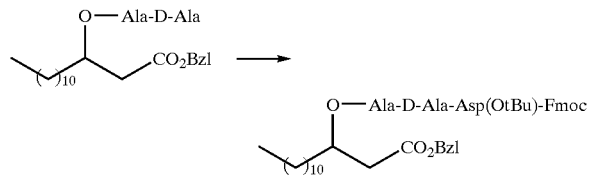

To a solution of the intermediate compound (41) (1.99 g) obtained in Synthesis Example 57, Fmoc-L-aspartic acid β-t-butyl ester (1.72 g) and HOBt.monohydrate (0.62 g) in dichloromethane (200 ml) was added under ice-cooling WSCI (1.20 g), the mixture was stirred under ice-cooling for one hour and then allowed to rise up to room temperature and stirred overnight. After the solvent was removed in vacuo, purification was carried out by a silica gel column chromatography (silica gel 100 g, chloroform: methanol= 50:0–1) to afford 3.42 g of the intermediate compound (42).

(NMR Data for the Intermediate Compound (42))

$^1$H-NMR (δ ppm, CDCl$_3$) 7.76 (2H, d, J=7.3 Hz), 7.58 (2H, d, J=7.3 Hz), 7.28–7.42 (9H, m), 6.97–7.01 (1H, m), 6.82–6.90 (1H, m), 5.93–5.97 (1H, m), 5.22–5.26 (1H, m), 5.10 (1H, d, J=12.2 Hz), 5.04 (1H, d, J=12.2 Hz), 4.21–4.59 (6H, m), 2.55–2.68 (3H, m), 3.04 (1H, dd, J=4.4 Hz, 17.1 Hz), 1.22–1.64 (35H, m), 0.88 (3H, t, J=6.3 Hz)

SYNTHESIS EXAMPLE 59

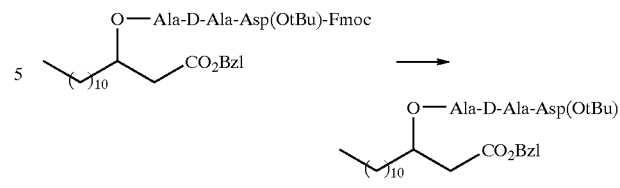

To a solution of the intermediate compound (42) (3.42 g) obtained in Synthesis Example 58 in DMF (30 ml) was added diethylamine (3 ml) and the mixture was stirred at room temperature for one hour. After the solvent was removed in vacuo, purification was carried out by a silica gel column chromatography (silica gel 100 g, chloroform methanol=50:0–1) to afford 2.52 g of the intermediate compound (43).

(NMR Data for the Intermediate Compound (43))

$^1$H-NMR (δ ppm, CDCl$_3$) 7.85 (1H, d, J=8.3 Hz), 7.00–7.06 (1H, m), 7.31–7.35 (5H, m), 5.23–5.27 (1H, m), 5.12 (1H, d, J=12.2 Hz), 5.07 (1H, d, J=12.2 Hz), 4.45–4.55 (2H, m), 3.57–3.60 (1H, m), 2.56–2.96 (4H, m), 1.24–1.66 (37H, m), 0.88 (3H, t, J=6.3 Hz)

SYNTHESIS EXAMPLE 60

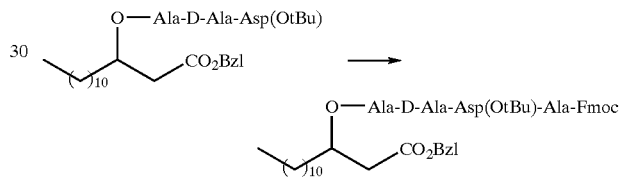

To a solution of the intermediate compound (43) (1.99 g) obtained in Synthesis Example 59, Fmoc-L-alanine.monohydrate (1.27 g) and HOBt.monohydrate (0.57 g) in dichloromethane (50 ml) was added under ice-cooling WSCI (1.11 g), the mixture was stirred under ice-cooling for one hour and then allowed to gradually rise up to room temperature and stirred overnight. After the solvent was removed in vacuo, purification was carried out by a silica gel chromatography (silica gel 100 g, chloroform: methanol= 50:0–1) to afford 3.45 g of the intermediate compound (44).

(NMR Data for the Intermediate Compound (44))

$^1$H-NMR (δ ppm, CDCl$_3$) 7.75 (2H, d, J=6.8 Hz), 7.13–7.63 (14H, m), 6.88–6.91 (1H, m), 5.40–5.43 (1H, m), 5.18–5.21 (1H, m), 5.00–5.11 (2H, m), 4.72–4.78 (1H, m), 4.42–4.53 (3H, m), 4.16–4.22 (2H, m), 2.47–2.96 (4H, m), 1.17–1.71 (38H, m), 0.88 (3H, t, J=6.8 Hz)

SYNTHESIS EXAMPLE 61

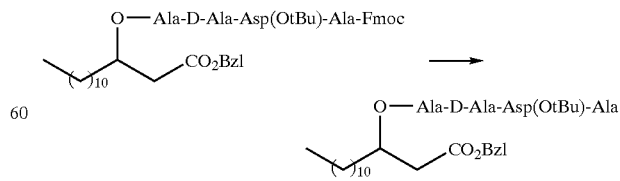

To a solution of the intermediate compound (44) (3.45 g) obtained in Synthesis Example 60 in DMF (30 ml) was added diethylamine (3 ml), the mixture was stirred at room temperature for 2 hours. After the solvent was removed in vacuo, purification was carried out by a silica gel column chromatography (silica gel 100 g, chloroform: methanol=100:0–5) to afford 2.88 g of the intermediate compound (45).

(NMR Data for the Intermediate Compound (45))

$^1$H-NMR (δ ppm, CDCl$_3$) 8.21–8.26 (1H, m), 7.13 (1H, d, J=7.8 Hz), 6.88–6.95 (1H, m), 7.32–7.37 (5H, m), 5.22–5.26 (1H, m), 5.06–5.14 (2H, m), 4.68–4.74 (1H, m), 4.39–4.56 (2H, m), 3.53–3.60 (1H, m), 2.56–2.95 (4H, m), 1.83 (2H, br), 1.24–1.64 (38H, m), 0.88 (3H, t, J=6.8 Hz)

SYNTHESIS EXAMPLE 62

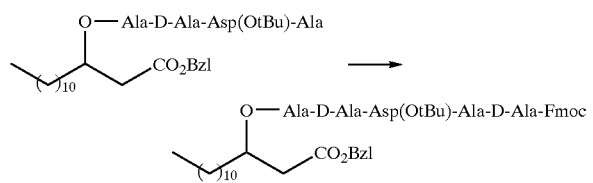

To a solution of the intermediate compound (45) (1.50 g) obtained in Synthesis Example 61, Fmoc-D-alanine (0.68 g) and HOBt.monohydrate (0.33 g) in dichloromethane (50 ml) was added under ice-cooling WSCI (0.58 g), the mixture was stirred under ice-cooling for 3 hours. After the solvent was removed in vacuo, purification was carried out by a silica gel column chromatography (silica gel 100 g, chloroform: methanol=50:0–1) to afford 1.76 g of the intermediate compound (46).

(NMR Data for the Intermediate Compound (46))

$^1$H-NMR (δ ppm, CDCl$_3$) 7.76 (2H, d, J=7.3 Hz), 7.56–7.60 (2H, m), 7.14–7.41 (12H, m), 6.95–7.01 (1H, m), 6.16–6.18 (1H, m), 5.24–5.27 (1H, m), 5.02–5.13 (2H, m), 4.19–4.54 (8H, m), 2.53–2.99 (4H, m), 1.14–1.66 (41H, m), 0.88 (3H, t, J=6.8 Hz)

SYNTHESIS EXAMPLE 63

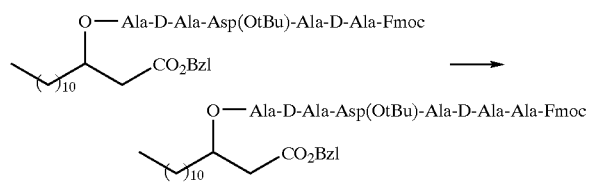

To a solution of the intermediate compound (46) (1.76 g) obtained in Synthesis Example 62 in DMF (30 ml) was added diethylamine (2 ml) and the mixture was stirred at room temperature for 4 hours. After the solvent was removed in vacuo, Fmoc-L-alanine-monohydrate (0.57 g) and HOBt.monohydrate (0.26 g) were added and dissolved in dichloromethane (30 ml). To this solution was added under ice-cooling WSCI (0.50 g) and the mixture was stirred under ice-cooling for 3 hours. After the solvent was removed in vacuo, purification was carried out by a silica gel column chromatography (silica gel 100 g, chloroform: methanol=50:0–1) to afford 1.55 g of the intermediate compound (47).

(NMR Data for the Intermediate Compound (47))

$^1$H-NMR (δ ppm, CDCl$_3$) 7.26–7.93 (18H, m), 5.40–5.48 (1H, m), 5.22–5.26 (1H, m), 5.08–5.10 (2H, m), 4.08–4.77 (9H, m), 3.05–3.13 (1H, m), 2.55–2.72 (3H, m), 1.21–1.67 (44H, m), 25 0.88 (3H, t, J=6.3 Hz)

SYNTHESIS EXAMPLE 64

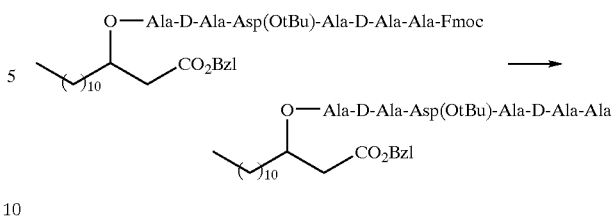

To a solution of the intermediate compound (47) (1.55 g) obtained in Synthesis Example 63 in DMF (30 ml) was added diethylamine (2 ml) and the mixture was stirred at room temperature for 1.5 hours. After the solvent was removed in vacuo, purification was carried out by a silica gel column chromatography (silica gel 100 g, chloroform: methanol=50:0–5) to afford 1.10 g of the intermediate compound (48).

(NMR Data for the Intermediate Compound (48))

$^1$H-NMR (δ ppm, CDCl$_3$) 6.96–7.92 (10H, m), 5.24–5.28 (1H, m), 5.07 (1H, d, J=12.2 Hz), 5.12 (1H, d, J=12.2 Hz), 4.25–4.61 (5H, m), 3.47–3.53 (1H, m), 2.83–2.95 (2H, m), 2.56–2.74 (2H, m), 1.24–2.91 (46H, m), 0.88 (3H, t, J=6.8 Hz)

SYNTHESIS EXAMPLE 65

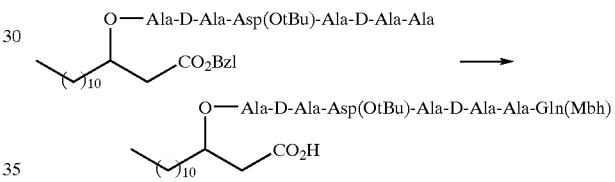

The intermediate compound (48) (1.10 g) obtained in Synthesis Example 64, N-α-Fmoc-N-γ-Mbh-L-glutamine (0.77 g) and HOBt.monohydrate (0.19 g) were dissolved in a mixed solvent of dichloromethane (30 ml) and DMF (25 ml), WSCI (0.36 g) was added under ice-cooling, the mixture was stirred under ice-cooling for one hour and then allowed to rise up to room temperature and stirred overnight. The reaction solution was concentrated and the residue was dissolved in DMF (100 ml), diethylamine (2 ml) was added and the mixture was stirred at room temperature for one hour. After the solvent was removed in vacuo, purification was carried out by a silica gel column chromatography (silica gel 100 g, chloroform: methanol=50:0–1). The purified product was dissolved in a mixed solvent of methanol (100 ml) and DMF (20 ml), 10% palladium carbon (0.21 g) was added and the mixture was stirred under hydrogen atmosphere for one hour. The palladium carbon was filtered off and the solvent was removed in vacuo to afford 1.29 g of the intermediate compound (49).

(NMR Data for the Intermediate Compound (49))

$^1$H-NMR (δ ppm, CDCl$_3$) 8.51–8.58 (2H, m), 8.23 (1H, d, J=7.8 Hz), 8.10 (1H, d, J=7.8 Hz), 7.90 (1H, bs), 7.62 (1H, bs), 7.24 (1H, d, J=7.3 Hz), 7.13–7.16 (4H, m), 6.80–6.83 (4H, m), 6.09 (1H, d, J=7.8 Hz), 5.17–5.20 (1H, m), 4.81–4.85 (1H, m), 4.43–4.48 (2H, m), 4.28–4.32 (1H, m), 4.02–4.11 (2H, m), 3.77 (s, 6H), 3.65–3.69 (1H, m), 3.01–3.06 (1H, m), 2.64–2.71 (1H, m), 2.48–2.51 (2H, m), 2.32–2.35 (2H, m), 1.95–2.06 (2H, m), 1.10–1.57 (46H, m), 0.88 (3H, t, J=6.3 Hz)

SYNTHESIS EXAMPLE 66

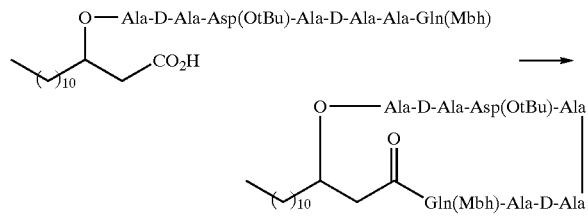

The intermediate compound (49) (0.12 g) obtained in Synthesis Example 65 was dissolved in a mixed solvent of THF (75 ml) and DMF (25 ml), and cesium chloride (0.18 g), potassium chloride (70 mg), N-methylmorpholine (20 mg), HOBt.monohydrate (60 mg) and WSCI (0.18 g) were added in turn and the mixture was stirred at room temperature for 5 days. After the solvent was removed in vacuo, the residue was purified by a silica gel column chromatography (silica gel 30 g, chloroform: methanol=50:0–1) to afford 0.11 g of the cyclic depsipeptide (13) of the invention.

(NMR Data for the Cyclic Depsipeptide (13))

$^1$H-NMR (δ ppm, CDCl$_3$) 8.04–8.18 (2H, m), 7.77 (1H, d, J=7.8 Hz), 7.55–7.60 (3H, m), 7.39–7.41 (1H, m), 7.13–7.16 (5H, m), 6.81–6.85 (4H, m), 6.11 (1H, d, J=8.3 Hz), 5.08–5.11 (1H, m), 4.77–4.81 (1H, m), 4.13–4.41 (6H, m), 3.78 (s, 6H), 3.01–3.04 (1H, m), 2.63–2.67 (1H, m), 2.30–2.47 (4H, m), 2.05–2.08 (2H, m), 1.25–1.67 (44H, m), 0.88 (3H, t, J=6.3 Hz)

SYNTHESIS EXAMPLE 67

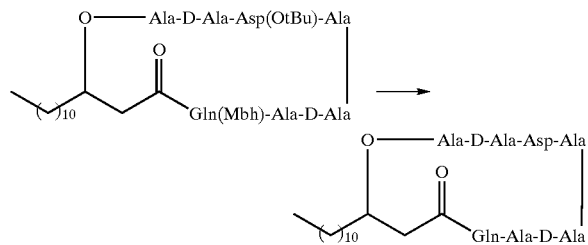

The cyclic depsipeptide (13) (0.11 g) obtained in Synthesis Example 66 was dissolved in TFA (3 ml) and the mixture was stirred at room temperature for 1.5 hours. After the solvent was removed in vacuo, to the residue were added chloroform and water, and the aqueous layer was neutralized with 5% aqueous sodium hydrogencarbonate. The insolubles thus precipitated out were recovered by filtration, washed with ether and dried under reduced pressure to afford 41 mg of the cyclic depsipeptide (14) of the invention.

(NMR Data for the Cyclic Depsipeptide (14))

$^1$H-NMR (δ ppm, d-DMSO) 8.27 (1H, bs), 7.69–8.11 (6H, m), 7.19 (1H, bs), 6.67 (1H, bs), 5.07–5.11 (1H, m), 4.17–4.34 (7H, m), 2.39–2.62 (2H, m), 1.58–1.89 (4H, m), 2.09–2.12 (2H, m), 1.08–1.25 (25H, m), 0.86 (3H, t, J=6.3 Hz) FAB-MS 825 (MH$^+$)

SYNTHESIS EXAMPLE 68

Fmoc-D-Leu+Val-OBzl→Fmoc-D-Leu-Val-OBzl

L-Valine benzyl ester-p-toluenesulfonate (8.35 g), Fmoc-D-leucine (7.07 g) and HOBt.monohydrate (3.37 g) were dissolved in dichloromethane (80 ml). To this solution was added under ice-cooling WSCI (4.22 g). This solution was stirred under ice-cooling for 2 hours and then allowed to rise up to room temperature and stirred for 2 days. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, the residue was purified by a silica gel column chromatography (silica gel 80 g, chloroform: methanol=200:0–4) to afford 6.27 g of the dipeptide (4).

(NMR Data for the Dipeptide (4))

$^1$H-NMR (CDCl$_3$) δ ppm: 7.76 (2H, d, J=8.0 Hz), 7.58 (2H, d, J=7.6 Hz), 7.24–7.35 (7H, m), 6.45–6.65 (1H, m), 5.17 (1H, d, J=12 Hz), 5.08 (1H, d, J=12 Hz), 5.02–5.26 (1H, m), 4.58 (1H, dd, J=4.4, 8.0 Hz), 4.40 (2H, d, J=6.8 Hz), 4.22 (1H, t, J=6.8 Hz), 4.15–4.31 (1H, m), 2.08–2.26 (1H, m), 1.53–1.79 (2H, m), 1.41–1.53 (1H, m), 0.70–0.96 (12H, m)

SYNTHESIS EXAMPLE 69

Fmoc-D-Leu-Val-OBzl→Fmoc-Leu-D-Leu-Val-OBzl

To a solution of the dipeptide (4) (5.00 g) obtained in Synthesis Example 68 in DMF (60 ml) was added diethylamine (6 ml) and the mixture was stirred at room temperature for 2 hours. After the solvent was removed in vacuo, Fmoc-L-leucine (3.58 g) and HOBt.monohydrate (1.55 g) were added and dissolved in dichloromethane (30 ml). To this solution was added under ice-cooling WSCI (1.94 g).

This solution was stirred under ice-cooling for 2 hours and then allowed to rise up to room temperature and stirred overnight. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, the residue was purified by a silica gel column chromatography (silica gel 50 g, chloroform: methanol=200:0–6) and further solidified using diethyl ether and hexane to afford 5.43 g of the tripeptide (5).

(NMR Data for the Tripeptide (5))

$^1$H-NMR (CDCl$_3$) δ ppm: 7.76 (2H, d, J=7.3 Hz), 7.57 (2H, d, J=7.3 Hz), 7.40 (2H, t, J=7.6 Hz), 7.20–7.36 (7H, m), 6.78 (1H, d, J=8.3 Hz), 6.36 (1H, d, J=7.8 Hz), 5.13 (1H, d, J=13 Hz), 5.03 (1H, d, J=13 Hz), 4.98–5.20 (1H, m), 4.41–4.53 (3H, m), 4.37 (1H, t, J=8.6 Hz), 4.08–4.26 (2H, m), 2.08–2.24 (1H, m), 1.38–1.83 (6H, m), 0.74–1.03 (13H, m)

SYNTHESIS EXAMPLE 70

Fmoc-Leu-D-Leu-Val-OBzl→Fmoc-Gln(Mbh)-Leu-D-Leu-Val-OBzl

To a solution of the tripeptide (5) (1.00 g) obtained in Synthesis Example 69 in DMF (12 ml) was added diethylamine (1.2 ml) and the mixture was stirred at room temperature for 2 hours. After the solvent was removed in vacuo, N-α-9-Fmoc-N-γ-Mbh-L-glutamine (1.00 g) and HOBt.monohydrate (0.26 g) were added and dissolved in dichloromethane (30 ml). To this solution was added under ice-cooling WSCI (0.32 g). This solution was stirred under. ice-cooling for 2 hours and then allowed to gradually rise up to room temperature and stirred overnight. After the dichloromethane was removed in vacuo, to the residue were added chloroform, ethyl acetate and 10% aqueous citric acid. The separated organic layer was washed in turn with water, 5% aqueous sodium hydrogencarbonate and water and then dried over anhydrous sodium sulfate. After the solvent was removed in vacuo, the residue was solidified using chloroform, methanol and diethyl ether to afford 1.48 g of the tetrapeptide (8).

(NMR Data for the Tetrapeptide (8)).
$^1$H-NMR (CDCl$_3$) δ ppm: 7.75 (2H, d, J=7.3 Hz), 7.62 (2H, d, J=7.6 Hz), 7.39 (2H, t, J=7.6 Hz), 7.24–7.35 (7H, m), 7.10–7.20 (4H, m), 6.78–6.88 (4H, m), 6.13 (1H, d, J=8.3 Hz), 5.14 (1H, d, J=12 Hz), 5.02 (1H, d, J=14 Hz), 4.28–4.50 (5H, m), 4.16–4.24 (1H, m), 4.00–4.10 (1H, m), 3.77 (3H, s), 3.75 (3H, s), 2.21–2.40 (2H, m), 2.08–2.21 (1H, m), 1.92–2.08 (2H, m), 1.42–1.75 (6H, m), 0.78–0.98 (18H, m)

SYNTHESIS EXAMPLE 71

Fmoc-Gln(Mbh)-Leu-D-Leu-Val-OBzl→Fmoc-Gln(Mbh)-Leu-D-Leu-Val

The tetrapeptide (8) (1.40 g) obtained in Synthesis Example 70 was dissolved in a mixed solvent of methanol (50 ml) and DMF (40 ml), 5% palladium carbon (0.14 g) was added and the mixture was stirred under hydrogen atmosphere for 2 hours. The palladium carbon was filtered off and the solvent was removed in vacuo to afford 1.10 g of the tetrapeptide (9).

(NMR Data for the Tetrapeptide (9))
$^1$H-NMR (CDCl$_3$) δ ppm: 7.77 (2H, d, J=7.3 Hz), 7.64 (2H, d, J=8.8 Hz), 7.37 (2H, t, J=7.3 Hz), 7.29 (2H, tt, J=1.1, 7.6 Hz), 7.14 (4H, dd, J=1.7, 9.3 Hz), 6.84 (4H, dd, J=2.4, 6.8 Hz), 6.09 (1H, s), 4.41–4.47 (1H, m), 4.31–4.39 (3H, m), 4.25 (1H, d, J=5.9 Hz), 4.12–4.22 (1H, m), 3.78–4.05 (1H, m), 3.75 (6H, s), 2.20–2.33 (2H, m), 2.09–2.20 (1H, m), 1.91–2.09 (2H, m), 1.53–1.71 (6H, m), 0.82–0.99 (18H, m)

SYNTHESIS EXAMPLE 72

Fmoc-Asp(OtBu)+D-Leu-OBzl→Fmoc-Asp(OtBu)-D-Leu-OBzl

Fmoc-L-Aspartic acid β-t-butyl ester (9.05 g), D-leucine benzyl ester (4.42 g) and HOBt.monohydrate (3.37 g) were dissolved in dichloromethane (80 ml). To this solution was added under ice-cooling WSCI (4.22 g). This solution was stirred under ice-cooling for 2 hours and then allowed to rise up to room temperature and stirred overnight. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 80 g, chloroform: methanol 200:0–4) to afford 8.36 g of the dipeptide (5).

(NMR Data for the Dipeptide (5))
$^1$H-NMR (CDCl$_3$) δ ppm: 7.77 (2H, d, J=7.3 Hz), 7.59 (2H, d, J=7.8 Hz), 7.40 (2H, t, J=7.3 Hz), 7.28–7.37 (7H, m), 6.94 (1H, d, J=7.8 Hz), 5.96 (1H, d, J=7.8 Hz), 5.17 (1H, d, J=12 Hz), 5.13 (1H, d, J=12 Hz), 4.53–4.67 (2H, m), 4.39 (2H, d, J=6.8 Hz), 4.23 (1H, t, J=7.1 Hz), 2.89 (1H, dd, J=3.2, 17 Hz), 2.62 (1H, dd, J=6.8, 17 Hz), 1.51–1.70 (3H, m), 1.44 (9H, s), 0.90 (3H, d, J=2.4 Hz), 0.88 (3H, d, J=2.4 Hz)

SYNTHESIS EXAMPLE 73

Fmoc-Asp(OtBu)-D-Leu-OBzl→Fmoc-Val-Asp(OtBu)-D-Leu-OBzl

To a solution of the dipeptide (5) (6.15 g) obtained in Synthesis Example 72 in DMF (100 ml) was added diethylamine (10 ml) and the mixture was stirred at room temperature for 2 hours. After the solvent was removed in vacuo, Fmoc-L-valine (3.39 g) and HOBt.monohydrate (1.53 g) were added and dissolved in DMF (70 ml). To this solution was added under ice-cooling WSCI (1.92 g). This solution was stirred under ice-cooling for 2 hours and then allowed to gradually rise up to room temperature and stirred overnight. After the DMF was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, the residue was purified by a silica gel column chromatography (silica gel 50 g, chloroform: methanol=200:0–6) and further solidified using diethyl ether and hexane to afford 6.19 g of the tripeptide (6).

(NMR Data for the Tripeptide (6))
$^1$H-NMR (CDCl$_3$) δ ppm: 7.77 (2H, d, J=7.3 Hz), 7.60 (2H, d, J=8.3 Hz), 7.40 (2H, dt, J=3.4, 7.3 Hz), 7.27–7.37 (7H, m), 7.22 (1H, d, J=7.8 Hz), 7.08 (1H, d, J=7.3 Hz), 5.29 (1H, d, J=6.8 Hz), 5.09 (2H, s), 4.79–4.86 (1H, m), 4.56–4.63 (1H, m), 4.41 (2H, d, J=7.3 Hz), 4.23 (1H, t, J=6.8 Hz), 4.01 (1H, t, J=6.3 Hz), 2.90 (1H, dd, J=4.4, 17 Hz), 2.58 (1H, dd, J=6.5, 17 Hz), 2.10–2.20 (1H, m), 1.56–1.68 (3H, m), 1.42 (9H, s), 0.98 (3H, d, J=6.8 Hz), 0.93 (3H, d, J=6.8 Hz), 0.85–0.91 (6H, m)

SYNTHESIS EXAMPLE 74

Fmoc-Val-Asp(OtBu)-D-Leu-OBzl→Fmoc-Val-Asp(OtBu)-D-Leu

The tripeptide (6) (2.44 g) obtained In Synthesis Example 73 was dissolved in methanol (100 ml), 5% palladium carbon (0.25 g) was added and the mixture was stirred under hydrogen atmosphere for 2 hours. The palladium carbon was filtered off and the solvent was removed in vacuo to afford 2.13 g of the tripeptide (7).

SYNTHESIS EXAMPLE 75

Fmoc-Leu+D-Leu-OBzl→Fmoc-Leu-D-Leu-OBzl

To Fmoc-L-leucine (8.16 g) and D-leucine benzyl ester (4.64g) was added HOBt.monohydrate (3.54 g) and the mixture was dissolved in dichloromethane (140 ml). To this solution was added under ice-cooling WSCI (4.43 g). This solution was stirred under ice-cooling for 2 hours and then allowed to gradually rise up to room temperature and stirred for 4 days. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 100 g, hexane: ethyl acetate=200:20–60) to afford 11.7 g of the dipeptide (6).

(NMR Data for the Dipeptide (6))
$^1$H-NMR (CDCl$_3$) δ ppm: 7.76 (2H, d, J=7.3 Hz), 7.57 (2H, d, J=7.3 Hz), 7.39 (2H, t, J=7.6 Hz), 7.27–7.36 (7H, m), 6.52 (1H, d, J=7.8 Hz), 5.19 (1H, d, J=7.8 Hz), 5.14 (1H, d, J=12 Hz), 5.09 (1H, d, J=12 Hz), 4.60–4.68 (1H, m), 4.34–4.46 (2H, m), 4.21 (1H, t, J=7.1 Hz), 4.17–4.29 (1H, m), 1.43–1.76 (6H, m), 0.93 (6H, d, J=5.4 Hz), 0.89 (6H, d, J=5.9 Hz)

SYNTHESIS EXAMPLE 76

Fmoc-Leu-D-Leu-OBzl→Fmoc-Gln(Mbh)-Leu-D-Leu-OBzl

To a solution of the dipeptide (6) (4.81 g) obtained in Synthesis Example 75 in DMF (90 ml) was added diethylamine (9 ml) and the mixture was stirred at room temperature for 2 hours. After the solvent was removed in vacuo, N-α-9-Fmoc-N-γ-Mbh-L-glutamine (5.14 g) and HOBt-.monohydrate (1.32 g) were added and dissolved in dichloromethane (60 ml). To this solution was added under ice-cooling WSCI (1.66 g). This solution was stirred under ice-cooling for 2 hours and then allowed to gradually rise up to room temperature and stirred overnight After the dichloromethane was removed in vacuo, to the residue were added a 10% methanolic solution of chloroform and 10% aqueous citric acid. The separated 10% chloroform-methanol layer was washed in turn with water, 5% aqueous sodium hydrogencarbonate and water and then dried over anhydrous sodium sulfate. After the 10% methanol-chloroform was removed in vacuo, the residue was solidified using chloroform and diethyl ether to afford 5.59 g of the tripeptide (8).

(NMR Data for the Tripeptide (8))

$^1$H-NMR (DMSO-d6) δ ppm: 8.51 (1H, d, J=8.3 Hz), 8.23 (1H, d, J=7.8 Hz), 7.86 (2H, d, J=7.8 Hz), 7.78 (1H, d, J=7.8 Hz), 7.70 (2H, t, J=5.9 Hz), 7.47 (1H, d, J=7.8 Hz), 7.39 (2H, t, J=7.3 Hz), 7.26–7.36 (7H, m), 7.14 (4H, dd, J=1.5, 8.8 Hz), 6.83 (4H, dd, J=2.4, 8.8 Hz), 6.02 (1H, d, J=8.3 Hz), 5.06 (2H, s), 4.35–4.46 (1H, m), 4.17–4.34 (4H, m), 4.00–4.08 (1H, m), 3.71 (3H, m), 3.70 (3H, s), 2.21–2.34 (2H, m), 1.90–2.01 (1H, m), 1.74–1.87 (1H, m), 1.47–1.64 (4H, m), 1.44 (2H, t, J=7.1 Hz), 0.75–0.91 (12H, m)

SYNTHESIS EXAMPLE 77

Fmoc-Gln(Mbh)-Leu-D-Leu-OBzl→Fmoc-Gln(Mbh)-Leu-D-Leu

The tripeptide (8) (2.73 g) obtained in Synthesis Example 76 was dissolved in a mixed solvent of methanol (50 ml) and DMF (50 ml), 5% palladium carbon (0.27 g) was added and the mixture was stirred under hydrogen atmosphere for 2 hours. The palladium carbon was filtered off and the solvent was removed in vacuo and'solidified with diethyl ether to afford 2.46 g of the tripeptide (9).

SYNTHESIS EXAMPLE 78

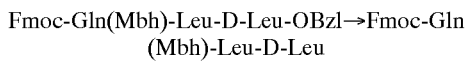

In a mixed solvent of benzene (100 ml) and diethyl ether (20 ml) were dissolved 4-methylpentylaldehyde (4.80 g) and ethyl bromoacetate (10.0 g). A portion (10 ml) of this solution was added to zinc powders (3.8 g) and the reaction was initiated by heating. After initiation of the reaction, the remaining solution was added dropwise while maintaining a gentle refluxing. After completion of the dropwise addition, the mixture was heated with stirring for 30 minutes. After cooling the reaction solution, a 10% aqueous sulfuric acid solution (100 ml) was slowly added while cooling. The mixture was allowed to stand and then the organic layer was separated. The separated organic layer was washed in turn with water, 5% aqueous sodium hydrogencarbonate and a saturated aqueous solution of sodium chloride and then dried over anhydrous sodium sulfate. After the solvent was removed in vacuo under reduced pressure, the residue was purified by a silica gel column chromatography (silica gel 100 g, hexane: ethyl acetate=100:20) to afford 5.0 g of β-hydroxyethyl ester.

(NMR Data for the p-hydroxyethyl Ester)

$^1$H-NMR (CDCl$_3$) δ ppm: 4.17 (2H, q, J=7 Hz), 3.97 (1H, m), 2.97 (1H, t, J=4 Hz), 2.53 (1H, dd, J=3, 17 Hz), 2.40 (1H, dd, J=9, 16 Hz), 1.53 (2H, m), 1.28 (3H, t, J=7 Hz), 1.30 (2H, m), 0.89 (6H, dd, J=1.7, 6.6 Hz)

SYNTHESIS EXAMPLE 79

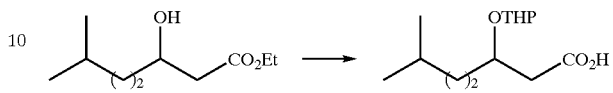

To a solution of the β-hydroxyethyl ester (5.0 g) obtained in Synthesis Example 78 in diethyl ether (100 ml) were added dihydropyrane (8.0 g) and p-toluenesulfonic acid (0.2 g) and the mixture was stirred at room temperature for 2 hours. The reaction solution was washed twice with a saturated aqueous sodium hydrogencarbonate solution and once with a saturated aqueous sodium chloride, and then dried over anhydrous sodium sulfate. The solvent was concentrated under reduced pressure to afford an oily product (7.33 g).

To a solution of the oily product (7.33 g) in methanol (50 ml) was added under ice-cooling an aqueous solution (20 ml) of potassium hydroxide (1.75 g). After 30 minutes, additional potassium hydroxide (2.0 g) was added. After 30 minutes, the methanol was removed in vacuo, and to the residue was added water (100 ml). After washing with isopropyl ether, the aqueous layer was neutralized with dilute hydrochloric acid and then extracted thrice with isopropyl ether. The combined isopropyl ether layers were washed with water and a saturated aqueous solution of sodium chloride and then dried over anhydrous magnesium sulfate. The solvent was concentrated under reduced pressure to afford 5.2 g of carboxylic acid.

(IR Data for the Carboxylic Acid)

IR (film, n): 3000 (br), 2953 (s), 2870 (m), 2700 (br), 1736 (sh), 1711 (s), 1026 (s) cm$^{-1}$

SYNTHESIS EXAMPLE 80

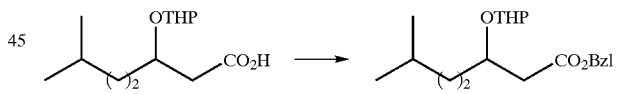

A solution of the carboxylic acid (5.2 g) obtained in Synthesis Example 79, benzyl bromide (7.28 g) and triethyl amine (4.3 g) in DMF (80 ml) was stirred at room temperature for 3 hours. After addition of isopropyl ether (100 ml) and water (100 ml), the organic layer was separated and the aqueous layer was extracted with isopropyl ether. The extract was combined with the organic layer and washed with water and a saturated aqueous solution of sodium chloride and then dried over anhydrous magnesium sulfate. After the solvent was removed in vacuo under reduced pressure, the residue was purified by a silica gel column chromatography (hexane: ethyl acetate=100:10) to afford 3.11 g of benzyl ester.

(NMR Data for the Benzyl Ester)

$^1$H-NMR (CDCl$_3$) δ ppm: 7.36 (5H, m), 5.12 (2H, 2s), 4.66 (1H, m), 4.05 (1H, m), 3.85 (1H, m), 3.42 (1H, m), 2.52 and 2.72 (2H, m), 1.70 (2H, m), 1.50 (6H, m), 1.25 (2H, m), 0.86 (6H, m)

SYNTHESIS EXAMPLE 81

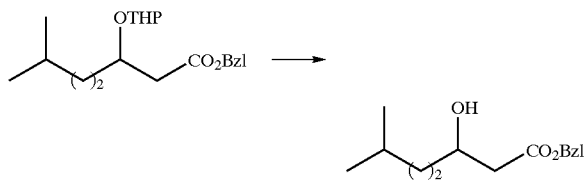

To a solution of the benzyl ester (3.11 g) obtained in Synthesis Example 80 in methanol (70 ml) was added p-toluenesulfonic acid (0.35 g) and the mixture was heated under reflux for one hour. After cooling to room temperature, isopropyl ether and water were added thereto. The organic layer was separated and the aqueous layer was extracted with isopropyl ether. The extract was combined with the organic layer and washed with water, a saturated aqueous sodium hydrogencarbonate solution and a saturated aqueous solution of sodium chloride and then dried over anhydrous magnesium sulfate. After the solvent was removed in vacuo under reduced pressure, the residue was purified by a silica gel column chromatography (silica gel 70 g, hexane: ethyl acetate=100:15) to afford 1.38 g of benzyl 6-methyl-3-hydroxyheptanoate.

(NMR Data for the Benzyl 6-methyl-3-hydroxyheptanoate)

$^1$H-NMR (CDCl$_3$) δ ppm: 7.36 (5H, m), 5.16 (2H, s), 4.00 (1H, br septet., J=3 Hz), 2.57 (1H, dd, J=3, 17 Hz), 2.46 (1H, dd, J=9, 17 Hz), 1.50 (3H, m), 1.32 (1H, m), 1.21 (1H, m), 0.88 (6H, d, J=7 Hz)

SYNTHESIS EXAMPLE 82

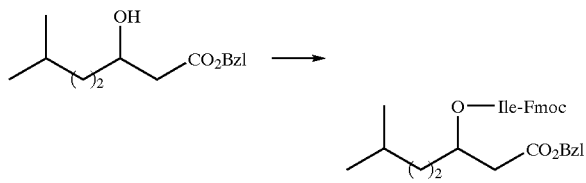

To a solution of the benzyl 6-methyl-3-hydroxyheptanoate (0.75 g), Fmoc-L-isoleucine (1.17 g) and dimethylaminopyridine (26 mg) in dichloromethane (20 ml) was added under ice-cooling DCC (0.93 g) and the mixture was stirred under ice-cooling for 2 hours and then allowed to gradually rise up to room temperature and stirred for 2 days. After a precipitate was removed by filtration, the dichloromethane was removed in vacuo. To the residue were added ethyl acetate and 10% aqueous citric acid. The separated organic layer was washed in turn with water, 5% aqueous sodium hydrogencarbonate and water and then dried over anhydrous sodium sulfate. After concentration, purification was carried out by a silica gel column chromatography (silica gel 30 g, hexane: ethyl acetate=200:0–20) to afford 1.76 g of the intermediate compound (50).

(NMR Data for the Intermediate Compound (50))

$^1$H-NMR (CDCl$_3$) δ ppm: 7.76 (2H, d, J=7.3 Hz), 7.60 (2H, d, J=7.3 Hz), 7.40 (2H, t, J=7.3 Hz), 7.27–7.37 (7H, m), 5.23–5.35 (2H, m), 5.11 (2H, s), 4.28–4.44 (3H, m), 4.23 (1H, t, J=6.8 Hz), 2.54–2.74 (2H, m), 1.80–1.97 (1H, m), 1.32–1.67 (4H, m), 1.06–1.28 (3H, m), 0.76–0.98 (12H, m)

SYNTHESIS EXAMPLE 83

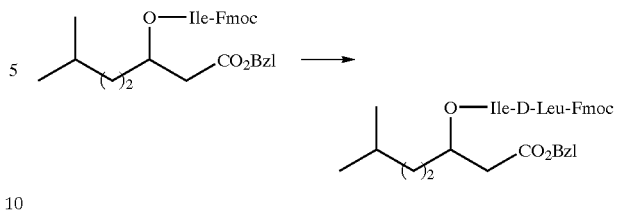

To a solution of the intermediate compound (50) (1.76 g) obtained in Synthesis Example 82 in DMF (30 ml) was added diethylamine (3 ml) and the mixture was stirred at room temperature for 2 hours. After the solvent was removed in vacuo, to a solution of the amine derivative thus obtained, Fmoc-D-leucine (1.17 g) and HOBt.monohydrate (0.51 g) in dichloromethane (20 ml) was added under ice-cooling WSCI (0.63 g). This solution was stirred under ice-cooling for 2 hours and then allowed to gradually rise up to room temperature and stirred overnight. After the dichloromethane was removed in vacuo, to the residue were added ethyl acetate and 10* aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 25 g, hexane: ethyl acetate=200:6–30) to afford 2.10 g of the intermediate compound (51).

(NMR Data for the Intermediate Compound (51))

$^1$H-NMR (CDCl$_3$) δ ppm: 7.76 (2H, d, J=7.8 Hz), 7.59 (2H, d, J=6.1 Hz), 7.40 (2H, t, J=7.6 Hz), 7.27–7.36 (7H, m), 6.45–6.59 (1H, m), 5.21–5.33 (1H, m), 50.9 (2H, s), 5.05–5.19 (1H, m), 4.33–4.56 (3H, m), 4.18–4.30 (2H, m), 2.54–2.71 (2H, m), 1.79–1.96 (1H, m), 1.31–1.75 (7H, m), 1.05–1.20 (3H, m), 0.78–1.00 (18H, m)

SYNTHESIS EXAMPLE 84

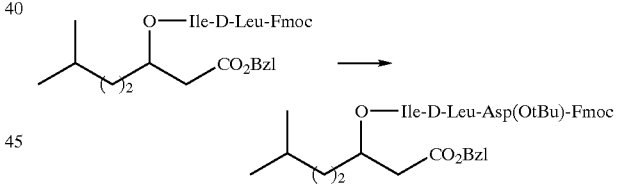

To a solution of the intermediate compound (51) (2.10 g) obtained in Synthesis Example 83 in DMF (30 ml) was added diethylamine (3 ml) and the mixture was stirred at room temperature for 2 hours. After the solvent was removed in vacuo, to a solution of the amine derivative thus obtained, Fmoc-L-aspartic acid β-t-butyl ester (1.36 g) and HOBt.monohydrate (0.51 g) in dichloromethane (20 ml) was added under ice-cooling WSCI (0.63 g). This solution was stirred under ice-cooling for 2 hours and then allowed to gradually rise up to room temperature and stirred overnight. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 25 g, hexane: ethyl acetate=200:10–50) to afford 2.61 g of the intermediate compound (52).

(NMR Data for the Intermediate Compound (52))

¹H-NMR (CDCl₃) δ ppm: 7.76 (2H, d, J=7.3 Hz), 7.53–7.62 (2H, m), 7.40 (2H, t, J=7.6 Hz), 7.27–7.36 (7H, m), 6.93, 6.85 (1H, 2d, J=8.3 Hz), 6.72 (1H, d, J=8.3 Hz), 5.98 (1H, d, J=8.3 Hz), 5.20–5.29 (1H, m), 5.01–5.12 (2H, m), 4.34–4.61 (5H, m), 4.22 (1H, t, J=6.8 Hz), 2.90–3.00 (1H, m), 2.51–2.74 (3H, m), 1.74–1.96 (2H, m), 1.34–1.68 (6H, m), 1.44 (9H, 2s), 1.07–1.21 (3H, m), 0.78–0.96 (18H, m)

SYNTHESIS EXAMPLE 85

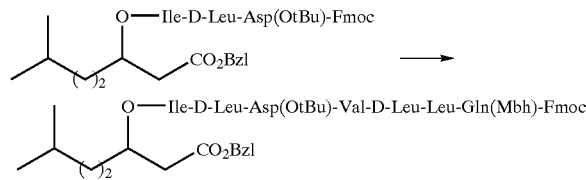

To a solution of the intermediate compound (52) (0.99 g) obtained in Synthesis Example 84 in DMF (20 ml) was added diethylamine (2 ml) and the mixture was stirred at room temperature for 2 hours. After the solvent was removed in vacuo, to a solution of the amine derivative thus obtained, the tetrapeptide (9) obtained in Synthesis Example 71 (1.10 g) and HOBt.monohydrate (0.18 g) in a mixed solvent of DMF (20 ml) and dichloromethane (10 ml) was added under ice-cooling WSCI (0.23 g). This solution was stirred under ice-cooling for 2 hours and then stirred at room temperature overnight. After the solvent was removed in vacuo, to the residue were added chloroform and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 50 g, chloroform: methanol 200:0–4) to afford 1.76 g of the intermediate compound (53).

(NMR Data for the Intermediate Compound (53))

¹H-NMR (CD₃OD) δ ppm: 7.75 (2H, d, J=7.3 Hz), 7.54–7.62 (2H, m), 7.37 (2H, t, J=7.6 Hz), 7.24–7.34 (7H, m), 7.15 (4H, d, J=8.3 Hz), 6.84 (4H, d, J=8.3 Hz), 6.12 (1H, s), 5.16–5.27 (1H, m), 5.02–5.14 (2H, m), 4.84 (1H, br s), 4.40–4.50 (2H, m), 4.12–4.50 (7H, m), 4.03 (1H, d, J=6.3 Hz), 3.76 (6H, s), 2.91–2.98 (1H, m), 2.54–2.78 (3H, m), 2.39 (2H, t, J=7.6 Hz), 1.95–2.17 (3H, m), 1.33–1.81 (13H, m), 1.42 (9H, s), 1.08–1.25 (3H, m), 0.76–1.03 (36H, m)

SYNTHESIS EXAMPLE 86

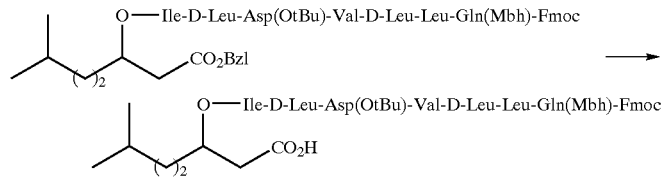

To a solution of the intermediate compound (53) (1.75 g) obtained in Synthesis Example 85 in DMF (30 ml) was added diethylamine (3 ml) and the mixture was stirred at room temperature for 2 hours. After the solvent was removed in vacuo, the amine derivative thus obtained was dissolved in methanol (50 ml), 5% palladium carbon (0.15 g) was added and the mixture was stirred under hydrogen atmosphere for 3 hours. After the palladium carbon was filtered off and the solvent was removed in vacuo, purification was carried out by a silica gel column chromatography (silica gel 30 g, chloroform: methanol=200:0–25) to afford 1.18 g of the intermediate compound (54).

(NMR Data for the Intermediate Compound (54))

¹H-NMR (CD₃OD) δ ppm: 7.13 (4H, d, J=8.8 Hz), 6.81–6.88 (4H, m), 6.07 (1H, s), 5.16–5.29 (1H, m), 4.70–4.84 (2H, m), 4.22–4.51 (3H, m), 4.00–4.12 (1H, m), 3.82–3.88 (1H, m), 3.76 (6H, s), 2.89–3.04 (1H, m), 2.70–2.80 (1H, m), 2.28–2.49 (4H, m), 2.05–2.19 (2H, m), 1.37–1.96 (15H, m), 1.44 (9H, s), 1.15–1.30 (3H, m), 0.79–1.02 (36H, m)

SYNTHESIS EXAMPLE 87

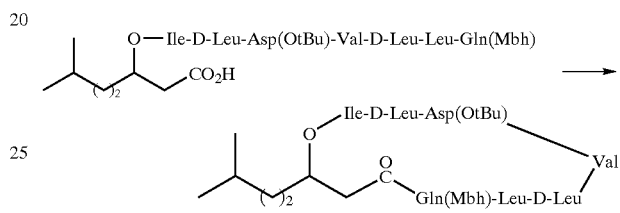

To a solution of the intermediate compound (54) (0.58 g) obtained in Synthesis Example 86 in THF (110 ml) were added N-methylmorpholine (0.10 ml) and HOBt.monohydrate (0.29 g) to form Solution A. To a mixed solvent of THF (220 ml) and DMF (110 ml) were added in turn cesium chloride (0.79 g), potassium chloride (0.31 g) and WSCI (0.81 g) to form Solution B. Solution A was added dropwise to Solution. B at room temperature over 20 minutes while stirring and further the mixture was stirred at room temperature for 7 days. The reaction solution was diluted with ethyl acetate (100 ml) and the mixture was washed in turn with water, 5% aqueous sodium hydrogencarbonate, water, 10% aqueous citric acid and water and then dried over anhydrous sodium sulfate. After the solvent was removed in vacuo, the residue was purified by a silica gel column chromatography (silica gel 30 g, chloroform: methanol= 200:0–6) and furthermore solidified with diethyl ether-hexane system to afford 0.36 g of the cyclic depsipeptide (15) of the invention.

(NMR Data for the Cyclic Depsipeptide (15))

¹H-NMR (CD3OD) δ ppm: 7.10–7.17 (4H, m), 6.82–6.88 (4H, m), 6.03–6.09 (1H, m), 5.15–5.23 (1H, m), 4.69–4.83 (1H, m), 4.22–4.51 (5H, m), 4.04–4.11 (1H, m), 3.77, 3.76 (6H, 2s), 2.64–2.91 (2H, m), 2.51–2.59 (1H, m), 2.15–2.45 (3H, m), 1.82–2.02 (3H, m), 1.36–1.78 (13H, m), 1.44 (9H, s), 1.13–1.33 (4H, m), 0.76–1.02 (36H, m)

SYNTHESIS EXAMPLE 88

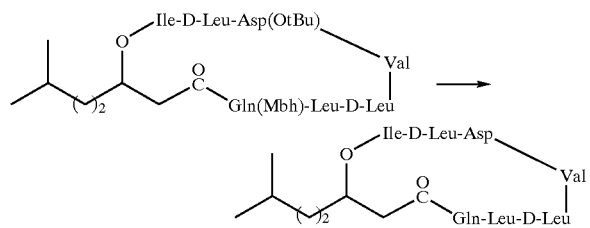

A solution of the cyclic depsipeptide (15) (0.35 g) obtained in Synthesis Example 87 in TFA (4 ml) was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and concentrated, and then purification was carried out by a silica gel column chromatography (silica gel 20 g, chloroform: methanol=100:0–50) to afford 0.21 g of the cyclic depsipeptide (16) of the invention.

(NMR Data for the Cyclic Depsipeptide (16))
$^1$H-NMR (CD$_3$OD) δ ppm: 5.07–5.32 (1H, m), 4.28–4.81 (6H, m), 4.05–4.21 (1H, m), 2.42–2.94 (4H, m), 2.11–2.32 (3H, m), 1.39–2.08 (1SH, m), 1.13–1.36 (4H, m), 0.80–1.11 (36H, m)

SYNTHESIS EXAMPLE 89

To a solution of 3-hydroxyoctanoic acid (1.90 g) and triethylamine (1.65 ml) in DMF (20 ml) was added benzyl bromide (1.41 ml) and the mixture was stirred at room temperature for 3 days. After the solvent was removed in vacuo, ethyl acetate and water were added to the residue. The separated ethyl acetate layer was washed twice with water and then dried over anhydrous sodium sulfate. After concentration, the residue was purified by a silica gel column chromatography (silica gel 15 g, chloroform: methanol=100:0–8) to afford 1.71 g of benzyl 3-hydroxyoctanoate.

(NMR Data for the Benzyl 3-hydroxyoctanoate)
$^1$H-NMR (CDCl$_3$) δ ppm: 7.31–7.41 (5H, m), 5.16 (2H, s), 3.98–4.06 (1H, m), 2.85 (1H, d, J=3.4 Hz), 2.57 (1H, dd, J=3.2, 17 Hz), 2.46 (1H, dd, J=8.8, 17 Hz), 1.22–1.60 (8H, m), 0.88 (3H, t, J=6.8 Hz)

SYNTHESIS EXAMPLE 90

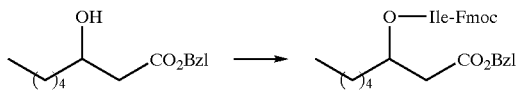

To a solution of the benzyl 3-hydroxyoctanoate (0.75 g), Fmoc-L-isoleucine (1.17 g) and dimethylamino-pyridine (26 mg) in dichloromethane (20 ml) was added under ice-cooling DCC (0.93 g) and the mixture was stirred under ice-cooling for 2 hours and then allowed to gradually rise up to room temperature and stirred for 3 days. After a precipitate was removed by filtration, the dichloromethane was removed in vacuo. To the residue were added ethyl acetate and 10% aqueous citric acid. The separated organic layer was washed in turn with water, 5% aqueous sodium hydrogencarbonate and water and then dried over anhydrous sodium sulfate. After concentration, the residue was purified by a silica gel column chromatography (silica gel 30 g, hexane: ethyl acetate=200:5–30) to afford 1.75 g of the intermediate compound (55).

(NMR Data for the Intermediate Compound (55))
$^1$H-NMR (CDCl$_3$) δ ppm: 7.76 (2H, d, J=7.3 Hz), 7.60 (2H, d, J=7.3 Hz), 7.40 (2H, t, J=7.3 Hz), 7.27–7.37 (7H, m), 5.22–5.36 (2H, m), 5.11 (2H, s), 4.34–4.44 (2H, m), 4.34–4.44 (2H, m), 4.31 (1H, dd, J=4.6, 8.3 Hz), 4.23 (1H, t, J=7.1 Hz), 2.54–2.74 (2H, m), 1.79–1.96 (1H, m), 1.51–1.71 (2H, m), 1.05–1.46 (8H, m), 0.76–0.97 (9H, m)

SYNTHESIS EXAMPLE 91

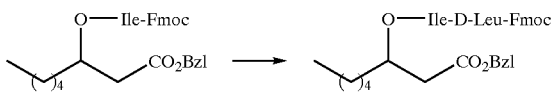

To a solution of the intermediate compound (55) (1.75 g) obtained in Synthesis Example 90 in DMF (30 ml) was added diethylamine (3 ml) and the mixture was stirred at room temperature for 2 hours. After the solvent was removed in vacuo, to a solution of the amine derivative thus obtained, Fmoc-D-leucine (1.17 g) and HOBt.monohydrate (0.51 g) in dichloromethane (20 ml) was added under ice-cooling WSCI (0.63 g). This solution was stirred under ice-cooling for 2 hours and then allowed to gradually rise up to room temperature and stirred for 2 days. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 25 g, hexane: ethyl acetate=200:5–35) to afford 2.10 g of the intermediate compound (56).

(NMR Data for the Intermediate Compound (56))
$^1$H-NMR (CDCl$_3$) δ ppm: 7.76 (2H, d, J=7.3 Hz), 7.57–7.60 (2H, m), 7.40 (2H, t, J=7.3 Hz), 7.27–7.36 (7H, m), 6.45–6.59 (1H, m), 5.22–5.33 (1H, m), 5.09 (2H, s), 5.04–5.18 (1H, m), 4.33–4.56 (3H, m), 4.18–4.30 (2H, m), 5 2.53–2.70 (2H, m), 1.79–1.95 (1H, m), 1.45–1.75 (5H, m), 1.04–1.44 (8H, m), 0.75–0.99 (15H, m)

SYNTHESIS EXAMPLE 92

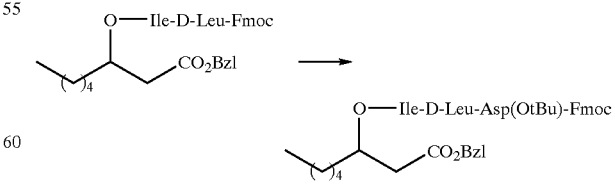

To a solution of the intermediate compound (56) (2.10 g) obtained in Synthesis Example 91 in DMF (30 ml) was added diethylamine (3 ml) and the mixture was stirred at room temperature for 2 hours. After the solvent was removed in vacuo, to a solution of the amine derivative thus obtained, Fmoc-L-aspartic acid β-t-butyl ester (1.36 g) and HOBt.monohydrate (0.51 g) in dichloromethane (20 ml) was added under ice-cooling WSCI (0.63 g). This solution was stirred under ice-cooling for 2 hours and then allowed to gradually rise up to room temperature and stirred for 3 days. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 25 g, hexane: ethyl acetate 200:10–60) to afford 1.94 g of the intermediate compound (57).

(NMR Data for the Intermediate Compound (57))

$^1$H-NMR (CDCl$_3$) δ ppm: 7.76 (2H, d, J=7.3 Hz), 7.58 (2H, d, J=7.8 Hz), 7.40 (2H, t, J=7.3 Hz), 7.27–7.37 (7H, m), 6.85–7.00 (1H, m), 6.75 (1H, d, J=8.3 Hz), 5.95–6.06 (1H, m), 5.21–5.31 (1H, m), 5.01–5.13 (2H, m), 4.34–4.62 (5H, m), 4.22 (1H, t, J=6.8 Hz), 2.87–3.01 (1H, m), 2.50–2.75 (3H, m), 1.74–1.97 (2H, m), 1.34–1.70 (4H, m), 1.44 (9H, 2s), 1.09–1.33 (8H, m), 0.77–0.96 (15H, m)

SYNTHESIS EXAMPLE 93

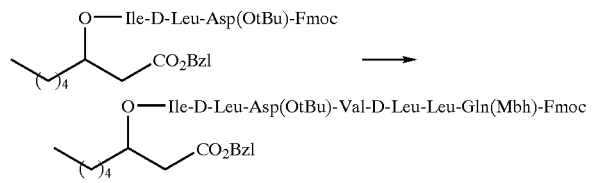

To a solution of the intermediate compound (57) (1.30 g) obtained in Synthesis Example 92 in DMF (14 ml) was added diethylamine (1.4 ml) and the mixture was stirred at room temperature for 3 hours. After the solvent was removed in vacuo, to a solution of the amine derivative thus obtained, the tetrapeptide (9) (1.37 g) obtained in Synthesis Example 71 and HOBt.monohydrate (0.23 g) in a mixed solvent of DMF (27 ml) and dichloromethane (16 ml) was added under ice-cooling WSCI (0.29 g). This solution was stirred under ice-cooling for 2 hours and then allowed to gradually rise up to room temperature and stirred for 2 days. After the solvent was removed in vacuo, to the residue were added chloroform and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 50 g, chloroform: methanol=200:0–6) to afford 1.61 g of the intermediate compound (58).

(NMR Data for the Intermediate Compound (58))

$^1$H-NMR (CD$_3$OD) δ ppm: 7.68–7.80 (2H, m), 7.53–7.63 (2H, m), 7.18–7.43 (9H, m), 7.13 (4H, d, J=8.3 Hz), 6.82 (4H, d, J=8.3 Hz), 6.09 (1H, s), 5.13–5.29 (1H, m), 4.98–5.13 (2H, m), 4.10–4.60 (9H, m), 3.98–4.06 (1H, m), 3.74 (6H, s), 2.52–3.00 (4H, m), 2.31–2.50 (2H, m), 1.96–2.20 (4H, m), 1.47–1.75 (1OH, m), 1.41 (9H, s), 1.08–1.45 (9H, m), 0.70–1.00 (33H, m)

SYNTHESIS EXAMPLE 94

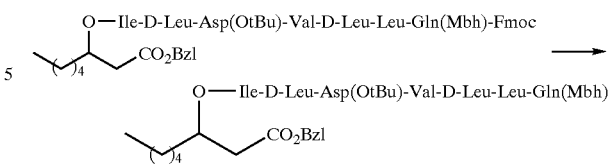

To a solution of the intermediate compound (58) (1.61 g) obtained in Synthesis Example 93 in DMF (20 ml) was added diethylamine (2 ml) and the mixture was stirred at room temperature for 3 hours. After the solvent was removed in vacuo, purification was carried out by a silica gel column chromatography (silica gel 20 g, chloroform: methanol=100:0–3) to afford 1.00 g of the intermediate compound (59).

(NMR Data for the Intermediate Compound (59))

$^1$H-NMR (CD$_3$OD) δ ppm: 7.27–7.38 (5H, m), 7.13 (4H, d, J=7.8 Hz), 6.84 (4H, d, J=8.8 Hz), 6.07 (1H, s), 5.21–5.29 (1H, m), 5.07–5.12 (2H, m), 4.71–4.78 (1H, m), 4.41–4.48 (2H, m), 4.29–4.38 (1H, m), 4.21–4.27 (1H, m), 3.97–4.01 (1H, m), 3.76 (6H, s), 3.37 (1H, t, J=7.1 Hz), 2.88–2.98 (1H, m), 2.62–2.79 (3H, m), 2.35 (2H, t, J=7.8 Hz), 2.08–2.17 (1H, m), 1.81–1.95 (2H, m), 1.50–1.80 (11H, m), 1.43 (9H, s), 1.12–1.48 (9H, m), 0.81–1.02 (33H, m)

SYNTHESIS EXAMPLE 95

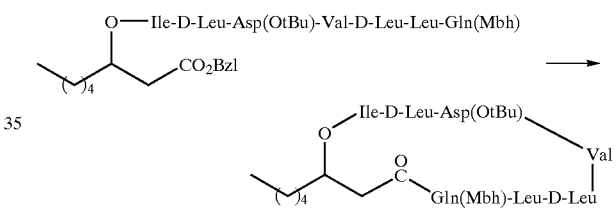

To a solution of the intermediate compound (59) (1.00 g) obtained in Synthesis Example 94 in methanol (35 ml) was added 5% palladium carbon (0.1 g) and the mixture was stirred under hydrogen atmosphere for 4 hours. The palladium carbon was filtered off and the methanol was removed in vacuo to afford an intermediate compound. The intermediate compound was dissolved in THF (170 ml) and N-3-methylmorpholine (0.17 ml) and HOBt.monohydrate (0.46 g) were added to form Solution A. To a mixed solvent of THF (340 ml) and DMF (170 ml) were added in turn cesium chloride (1.27 g), potassium chloride (0.51 g) and WSCI (1.30 g) to form Solution B. Solution A was added dropwise to Solution B at room temperature over 20 minutes while stirring and the mixture was further stirred at room temperature for 7 days. The reaction solution was diluted with ethyl acetate (200 ml) and the mixture was washed in turn with water, 5% aqueous sodium hydrogen-carbonate, water, 10% aqueous citric acid and water and then dried over anhydrous sodium sulfate. After the solvent was removed in vacuo, the residue was purified by a silica gel column chromatography (silica gel 30 g, chloroform: methanol= 200:0–6) and furthermore solidified with diethyl ether and hexane to afford 0.64 g of the cyclic depsipeptide (17) of the invention.

(NMR Data for the Cyclic Depsipeptide (17))

$^1$H-NMR (CD$_3$OD) δ ppm: 7.10–7.16 (4H, m), 6.82–6.88 (4H, m), 6.04–6.09 (1H, m), 5.09–5.25 (1H, m), 4.70–4.77

(1H, m), 4.23–4.51 (5H, m), 4.03–4.13 (1H, m), 3.77 (3H, s), 3.76 (3H, s), 2.64–2.91 (2H, m), 2.51–2.58 (1H, m), 2.15–2.43 (3H, m), 1.82–2.03 (3H, m), 1.51–1.78 (11H, m), 1.44 (9H, s), 1.13–1.49 (9H, m), 0.77–1.04 (33H, m)

SYNTHESIS EXAMPLE 96

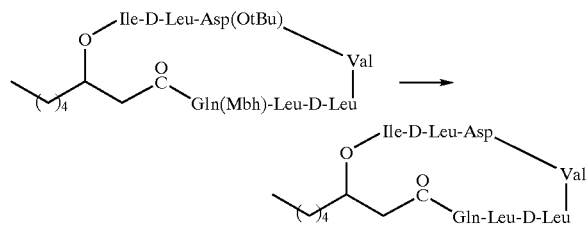

A solution of the cyclic depsipeptide (17) (0.64 g) obtained in Synthesis Example 95 in TFA (8 ml) was stirred at room temperature for 3 hours. After the solvent was removed in vacuo, the residue was neutralized with 5% aqueous sodium hydrogencarbonate and extracted with a 10% methanolic solution of chloroform. The organic layer was dried over anhydrous sodium sulfate and concentrated, and then purified by a silica gel column chromatography (silica gel 20 g, chloroform: methanol=100:0–50) and furthermore solidified using diethyl ether and hexane to afford 0.36 g of the cyclic depsipeptide (18) of the invention.

(NMR Data for the Cyclic Depsipeptide (18))
$^1$H-NMR (CD$_3$OD) δ ppm: 5.13–5.33 (1H, m), 4.22–4.82 (6H, m), 4.06–4.22 (1H, m), 2.39–2.93 (4H, m), 1.50–2.34 (16H, m), 1.14–1.50 (9H, m), 0.79–1.09 (33H, m)

SYNTHESIS EXAMPLE 97

To a solution of 3-hydroxyhexadecanoic acid (1.90 g) and triethylamine (0.97 ml) in DMF (20 ml) was added benzyl bromide (0.83 ml) and the mixture was stirred at room temperature for 3 days. After the solvent was removed in vacuo, ethyl acetate and water were added to the residue. The separated ethyl acetate layer was washed twice with water and then dried over anhydrous sodium sulfate. After concentration, the residue was purified by a silica gel column chromatography (silica gel 15 g, chloroform: methanol=100:0–8) to afford 1.22 g of benzyl 3-hydroxyhexadecanoate.

(NMR Data for the Benzyl 3-hydroxyhexadecanoate)
$^1$H-NMR (CDCl$_3$) δ ppm: 7.31–7.40 (5H, m), 5.16 (2H, s), 4.02 (1H, br s), 2.84 (1H, br s), 2.56 (1H, dd, J=3.4, 17 Hz), 2.46 (1H, dd, J=8.8, 17 Hz), 1.47–1.61 (2H, m), 1.37–1.47 (2H, m), 1.20–1.37 (20H, m), 0.88 (3H, t, J=6.8 Hz)

SYNTHESIS EXAMPLE 98

To a solution of the benzyl 3-hydroxyhexadecanoate (1.04 g), Fmoc-L-isoleucine (1.17 g) and dimethylamino-pyridine (26 mg) in dichloromethane (20 ml) was added under ice-cooling DCC (0.93 g) and the mixture was stirred under ice-cooling for 2 hours and then allowed to gradually rise up to room temperature and stirred for 2 days. After a precipitate was removed by filtration, the dichloromethane was removed in vacuo. To the residue were added ethyl acetate and 10% aqueous citric acid. The separated organic layer was washed in turn with water, 5% aqueous sodium hydrogencarbonate and water and then dried over anhydrous sodium sulfate. After concentration, purification was carried out by a silica gel column chromatography (silica gel 30 g, hexane: ethyl acetate=200:0–25) to afford 2.00 g of the intermediate compound (60).

(NMR Data for the Intermediate Compound (60))
$^1$H-NMR (CDCl$_3$) δ ppm: 7.76 (2H, d, J=7.3 Hz), 7.60 (2H, d, J=7.3 Hz), 7.40 (2H, t, J=7.3 Hz), 7.27–7.37 (7H, m), 5.23–5.36 (2H, m), 5.11 (2H, s), 4.35–4.43 (2H, m), 4.31 (1H, dd, J=4.6, 9.3 Hz), 4.23 (1H, t, J=7.1 Hz), 2.55–2.73 (2H, m), 1.80–1.94 (1H, m), 1.51–1.71 (2H, m), 1.04–1.46 (24H, m), 0.78–0.98 (9H, m)

SYNTHESIS EXAMPLE 99

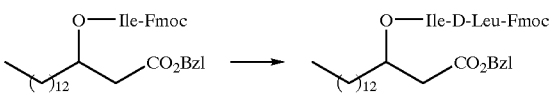

To a solution of the intermediate compound (60) (2.00 g) obtained in Synthesis Example 98 in DMF (30 ml) was added diethylamine (3 ml) and the mixture was stirred at room temperature for 2 hours. After the solvent was removed in vacuo, to a solution of the amine derivative thus obtained, Fmoc-D-leucine (1.12 g) and HOBt.monohydrate (0.48 g) in dichloromethane (20 ml) was added under ice-cooling WSCI (0.60 g). This solution was stirred under ice-cooling for 2 hours and then allowed to gradually rise up to room temperature and stirred for 2 days. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 25 g, hexane: ethyl acetate=200:5–30) to afford 2.35 g of the intermediate compound (61).

(NMR Data for the Intermediate Compound (61))
$^1$H-NMR (CDCl$_3$) δ ppm: 7.76 (2H, d, J=7.8 Hz), 7.57–7.60 (2H, m), 7.39 (2H, t, J=7.6 Hz), 7.27–7.36 (7H, m), 6.44–6.60 (1H, m), 5.22–5.34 (1H, m), 5.09 (2H, s), 5.04–5.18 (1H, m), 4.32–4.55 (3H, m), 4.18–4.30 (2H, m), 2.53–2.70 (2H, m), 1.79–1.96 (1H, m), 1.44–1.76 (5H, m), 1.02–1.44 (24H, m), 0.78–1.00 (15H, m)

SYNTHESIS EXAMPLE 100

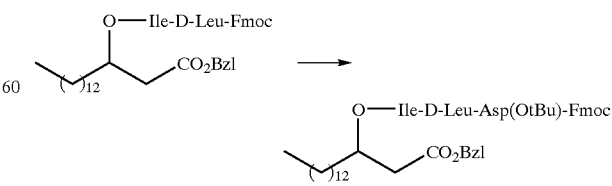

To a solution of the intermediate compound (61) (2.35 g) obtained in Synthesis Example 99 in DMF (30 ml) was added diethylamine (3 ml) and the mixture was stirred at room temperature for 3 hours. After the solvent was removed in vacuo, to a solution of the amine derivative thus obtained, Fmoc-L-aspartic acid β-t-butyl ester (1.31 g) and HOBt.monohydrate (0.49 g) in dichloromethane (20 ml) was added under ice-cooling WSCI (0.61 g). This solution was stirred under ice-cooling for 2 hours and then allowed to gradually rise up to room temperature and stirred overnight. After the dichloromethane was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 25 g, hexane: ethyl acetate=200:10–50) to afford 2.57 g of the intermediate compound (62).

(NMR Data for the Intermediate Compound (62))

$^1$H-NMR (CDCl$_3$) δ ppm: 7.76 (2H, d, J=7.8 Hz), 7.58 (2H, d, J=7.3 Hz), 7.39 (2H, t, J=7.3 Hz), 7.27–7.36 (7H, m), 6.84–6.93 (1H, m), 6.69–6.75 (1H, m), 5.95–6.05 (1H, m), 5.20–5.30 (1H, m), 5.01–5.12 (2H, m), 4.34–4.62 (5H, m), 4.22 (1H, t, J=7.1 Hz), 2.89–3.00 (1H, m), 2.50–2.75 (3H, m), 1.74–1.97 (2H, m), 1.34–1.70 (4H, m), 1.44 (9H, 2s), 1.10–1.34 (24H, m), 0.82–0.98 (15H, m)

SYNTHESIS EXAMPLE 101

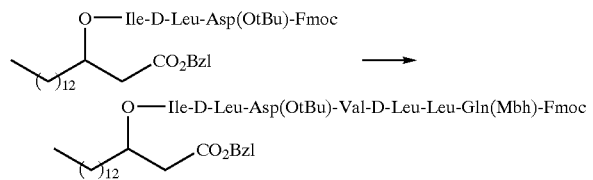

To a solution of the intermediate compound (62) (1.34 g) obtained in Synthesis Example 100 in DMF (14 ml) was added diethylamine (1.4 ml) and the mixture was stirred at room temperature for 3 hours. After the solvent was removed in vacuo, to a solution of the amine derivative thus obtained, the tetrapeptide (9) (1.25 g) obtained in Synthesis Example 71 and HOBt.monohydrate (0.21 g) in a mixed solvent of DMF (25 ml) and dichloromethane (15 ml) was added under ice-cooling WSCI (0.26 g). This solution was stirred under ice-cooling for 2 hours and then allowed to gradually rise up to room temperature and stirred for 2 days. After the solvent was removed in vacuo, to the residue were added chloroform and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, purification was carried out by a silica gel column chromatography (silica gel 50 g, chloroform: methanol=200:0–6) to afford 1.28 g of the intermediate compound (63).

(NMR Data for the Intermediate Compound (63))

$^1$H-NMR (CD$_3$OD) δ ppm: 7.69–7.79 (2H, m), 7.56–7.63 (2H, m), 7.23–7.40 (9H, m), 7.14 (4H, d, J=8.8 Hz), 6.83 (4H, dd, J=1.8, 8.8 Hz), 6.10 (1H, s), 5.18–5.27 (1H, m), 5.03–5.10 (2H, m), 4.21–4.61 (5H, m), 4.13–4.20 (1H, m), 4.00–4.05 (1H, m), 3.75 (6H, s), 2.53–2.91 (4H, m), 2.40 (2H, t, J=7.6 Hz), 2.10–2.19 (1H, m), 1.95–2.06 (2H, m), 1.83–1.93 (1H, m), 1.48–1.81 (10H, m), 1.42 (9H, s), 1.13–1.46 (25H, m), 0.79–1.00 (33H, m)

SYNTHESIS EXAMPLE 102

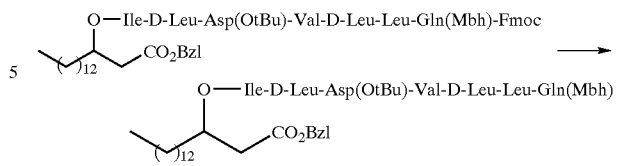

To a solution of the intermediate compound (63) (1.28 g) obtained in Synthesis Example 101 in DMF (15 ml) was added diethylamine (1.5 ml) and the mixture was stirred at room temperature for 3 hours. After the solvent was removed in vacuo, purification was carried out by a silica gel column chromatography (silica gel 20 g, chloroform: methanol=100:0–3.5) to afford 0.82 g of the intermediate compound (64).

(NMR Data for the Intermediate Compound (64))

$^1$H-NMR(CD$_3$OD) δ ppm: 7.27–7.38 (5H, m), 7.13 (4H, d, J=8.3 Hz), 6.84 (4H, d, J=8.8 Hz), 6.07 (1H, s), 5.21–5.29 (1H, m), 5.08–5.12 (2H, m), 4.71–4.79(1H, m), 4.41–4.49 (2H, m), 4.29–4.39 (1H, m), 4.20–4.28 (1H, m), 3.97–4.01 (1H, m), 3.76 (6H, s), 3.30–3.40 (1H, m), 2.89–3.01 (1H, m), 2.62–2.79 (3H, m), 2.36 (2H, t, J=7.8 Hz), 2.09–2.18 (1H, m), 1.83–1.95 (2H, m), 1.51–1.77 (11H, m), 1.43 (9H, s), 1.12–1.47 (25H, m), 0.81–1.01 (33H, m)

SYNTHESIS EXAMPLE 103

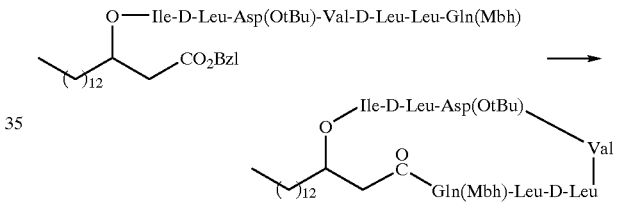

To a solution of the intermediate compound (64) (0.82 g) obtained in Synthesis Example 102 in methanol (25 ml) was added 5% palladium carbon (0.08 g) and the mixture was stirred under hydrogen atmosphere for 4 hours. The palladium carbon was filtered off and the methanol was removed in vacuo to afford a depsipeptide. This intermediate compound was dissolved in THF (130 ml) and N-methylmorpholine (0.13 ml) and HOBt.monohydrate (0.35 g) were added to form Solution A. To a mixed solvent of THF (260 ml) and DMF (130 ml) were added in turn cesium chloride (0.96 g), potassium chloride (0.38 g) and WSCI (0.98 g) to form Solution B. Solution A was added dropwise to Solution B at room temperature over 20 minutes while stirring and the mixture was further stirred at room temperature for 11 days. The reaction solution was diluted with ethyl acetate (150 ml) and the mixture was washed in turn with water, 5% aqueous sodium hydrogen-carbonate, water, 10% aqueous citric acid and water and then dried over anhydrous sodium sulfate. After the solvent was removed in vacuo, the residue was purified by a silica gel column chromatography (silica gel 30 g, chloroform:methanol=200:0–6) and furthermore solidified with diethyl ether and hexane to afford 0.60 g of the cyclic depsipeptide (19) of the invention.

(NMR Data for the Cyclic Depsipeptide (19))

$^1$H-NMR (CD$_3$OD) δ ppm: 7.10–7.16 (4H, m), 6.82–6.89 (4H, m), 6.04–6.09 (1H, m), 5.11–5.25 (1H, m), 4.69–4.76 (1H, m), 4.22–4.51 (5H, m), 4.03–4.13 (1H, m), 3.77 (3H, s), 3.76 (3H, s), 2.64–2.92 (2H, m), 2.51–2.58 (1H, m), 2.15–2.43 (3H, m), 1.81–2.04 (4H, m), 1.51–1.78 (10H, m), 1.44 (9H, s), 1.11–1.48 (25H, m), 0.77–1.05 (33H, m)

SYNTHESIS EXAMPLE 104

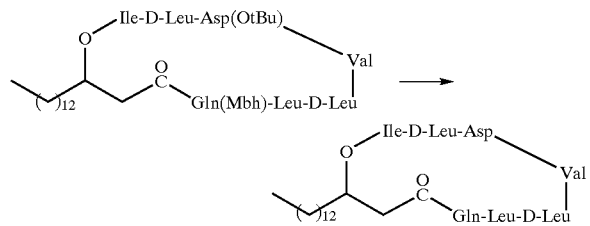

A solution of the cyclic depsipeptide (19) (0.60 g) obtained in Synthesis Example 103 in TFA (7 ml) was stirred at room temperature for 3 hours. After the solvent was removed in vacuo, the residue was neutralized with 5% aqueous sodium hydrogen-carbonate and extracted with a 10% methanolic solution of chloroform. The organic layer was dried over anhydrous sodium sulfate and concentrated, and then purified by a silica gel column chromatography (silica gel 20 g, chloroform:methanol=100:0–40) and furthermore solidified using diethyl ether-hexane to afford 0.33 g of the cyclic depsipeptide (20) of the invention (hereinafter referred to as "Compound 8").

(NMR Data for Compound 8)

$^1$H-NMR (CD$_3$OD) δ ppm: 5.12–5.33 (1H, m), 4.67–4.80 (1H, m), 4.26–4.63 (5H, m), 4.04–4.20 (1H, m), 2.38–2.93 (4H, m), 1.50–2.34 (16H, m), 1.17–1.50 (25H, m), 0.81–1.09 (33H, m)

SYNTHESIS EXAMPLE 105

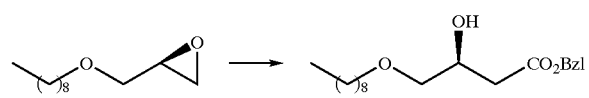

To a 40% ethanolic solution (15 ml) of sodium cyanide (2.11 g) was added a 40% ethanolic solution (6 ml) of (R)-(+)-1,2-epoxy-3-nonyloxypropane (2.73 g). The reaction solution was heated under reflux for 8 hours and then the ethanol was removed in vacuo. To the residue was added under cooling 1N aqueous hydrochloric acid to adjust to pH 4 and the mixture was then extracted with chloroform. The combined chloroform layers were dried over anhydrous sodium sulfate and the solvent was removed in vacuo to afford the intermediate compound carboxylic acid.

A solution of the carboxylic acid thus obtained, triethylamine (1.90 ml) and benzyl bromide (1.61 ml) in DMF (40 ml) was stirred at room temperature overnight. After the solvent was removed in vacuo, ethyl acetate and water were added to the residue. The separated ethyl acetate layer was washed twice with water and then dried over anhydrous sodium sulfate. After the ethyl acetate was removed in vacuo, the residue was purified by a silica gel column chromatography (silica gel 20 g, hexane:ethyl acetate= 200:0–20) to afford 1.51 g of benzyl nonyloxyhydroxybutanoate.

(NMR Data for Benzyl Nonyloxyhydroxybutanoate)

$^1$H-NMR (CDCl$_3$) δ ppm: 7.29–7.39 (5H, m), 5.15 (2H, s), 4.18–4.27 (1H, m), 3.36–3.49 (4H, m), 2.93 (1H, d, J=3.9 Hz), 2.58 (2H, d, J=6.3 Hz), 1.55 (2H, quint., J=6.8 Hz), 1.19–1.36 (12H, m), 0.88 (3H, t, J=6.8 Hz)

SYNTHESIS EXAMPLE 106

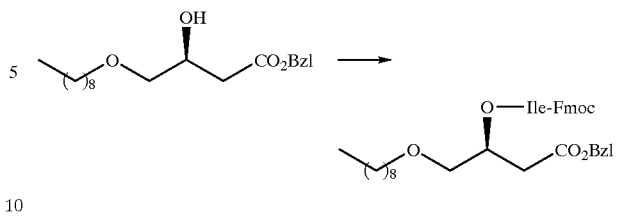

To a solution of the ester (1.50 g) obtained in Synthesis Example 105, Fmoc-L-isoleucine (1.73 g) and dimethylaminopyridine (38 mg) in dichloromethane (30 ml) was added under ice-cooling DCC (1.38 g) and the mixture was stirred under ice-cooling for 2 hours and then allowed to gradually rise up to room temperature and stirred for 3 days. After a precipitate was removed by filtration, the dichloromethane was removed in vacuo. To the residue were added ethyl acetate and 10% aqueous citric acid. The separated organic layer was washed in turn with water, 5% aqueous sodium hydrogencarbonate and water and then dried over anhydrous sodium sulfate. After concentration, purification was carried out by a silica gel column chromatography (silica gel 50 g, hexane:ethyl acetate=200:0–30) to afford 2.41 g of the intermediate compound (65).

(NMR Data for the Intermediate Compound (65))

$^1$H-NMR (CDCl$_3$) δ ppm: 7.76 (2H, d, J=7.8 Hz), 7.60 (2H, d, J=4.9 Hz), 7.40 (2H, t, J=7.3 Hz), 7.27–7.37 (7H, m), 5.39–5.48 (1H, m), 5.32 (1H, d, J=8.8 Hz), 5.12 (2H, s), 4.36–4.42 (2H, m), 4.32 (1H, dd, J=4.9, 8.8 Hz), 4.23 (1H, t, J=6.8 Hz), 3.45–3.60 (2H, m), 3.31–3.45 (2H, m), 2.74 (2H, d, J=6.8 Hz), 1.88 (1H, br s), 1.38–1.56 (2H, m), 1.11–1.34 (14H, m), 0.79–0.98 (9H, m)

SYNTHESIS EXAMPLE 107

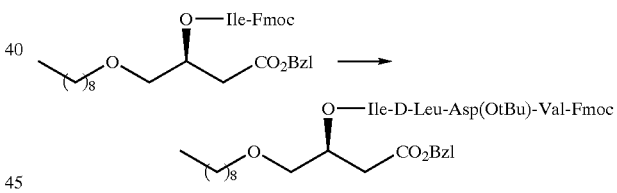

To a solution of the intermediate compound (65) (2.09 g) obtained in Synthesis Example 106 in DMF (30 ml) was added diethylamine (3 ml) and the mixture was stirred at room temperature for 3 hours. After the solvent was removed in vacuo, to a solution of the amine derivative thus obtained, the tripeptide (6) (2.13 g) obtained in Synthesis Example 74 and HOBt.monohydrate (0.52 g) in dichloromethane (25 ml) was added under ice-cooling WSCI (0.66 g). This solution was stirred under ice-cooling for 2 hours and then stirred at room temperature for 2 days. After the solvent was removed in vacuo, to the residue were added ethyl acetate and 10% aqueous citric acid. The separated ethyl acetate layer was washed in turn with water, 5% aqueous sodium hydrogencarbonate and water and then dried over anhydrous sodium sulfate. After the ethyl acetate was removed in vacuo, the residue was purified by a silica gel column chromatography (silica gel 50 g, chloroform:) methanol 200:0–3) and furthermore solidified using diethyl ether and hexane to afford 1.26 g of the desired intermediate compound (66).

(NMR Data for the Intermediate Compound (66))

¹H-NMR (CDCl₃) δ ppm: 7.75 (2H, d, J=7.3 Hz), 7.61 (2H, t, J=7.3 Hz), 7.38 (2H, t, J=7.6 Hz), 7.23–7.36 (8H, m), 7.02 (1H, d, J=7.8 Hz), 6.91 (1H, d, 8.3 Hz), 5.57 (1H, d, J=5.9 Hz), 5.33–5.40 (1H, m), 5.02–5.10 (2H, m), 4.80–4.89 (1H, m), 4.35–4.57 (4H, m), 4.22 (1H, t, J=6.8 Hz), 3.97 (1H, br s), 3.50 (1H, dd, J=5.4, 11 Hz), 3.44 (1H, dd, J=4.4, 11 Hz), 3.28–3.39 (2H, m), 2.85 (1H, dd, J=5.9, 17 Hz), 2.75 (1H, dd, J=5.9, 18 Hz), 2.66 (2H, d, J=6.3 Hz), 2.06–2.15 (1H, m), 1.71–1.93 (4H, m), 1.55–1.67 (2H, m), 1.35–1.51 (2H, m), 1.42 (9H, s), 1.15–1.33 (12H, m), 0.82–1.01 (21H, m)

SYNTHESIS EXAMPLE 108

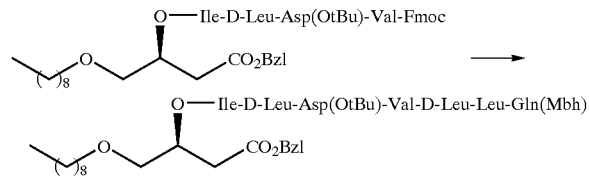

To a solution of the intermediate compound (66) (1.10 g) obtained in Synthesis Example 107 in DMF (10 ml) was added diethylamine (1 ml) and the mixture was stirred at room temperature for 3 hours. After the solvent was removed in vacuo, to a solution of the amine derivative thus obtained, the tripeptide (9) (0.94 g) obtained in Synthesis Example 77 and HOBt.monohydrate (0.18 g) in DMF (10 ml) was added under ice-cooling WSCI (0.22 g). This solution was stirred under ice-cooling for 2 hours and then allowed to gradually rise up to room temperature and stirred for 2 days. After the solvent was removed in vacuo, to the residue were added chloroform and 10% aqueous citric acid. The separated chloroform layer was washed in turn with water, 5% aqueous sodium hydrogencarbonate and water and then dried over anhydrous sodium sulfate. After the chloroform was removed in vacuo, purification was carried out by a silica gel column chromatography (silica gel 30 g, chloroform:ethyl acetate=200:0–60) to afford an intermediate compound.

To a solution of the intermediate compound thus obtained in DMF (18 ml) was added diethylamine (1.8 ml) and the mixture was stirred at room temperature for 3 hours. After the solvent was removed in vacuo, purification was carried out by a silica gel column chromatography (silica gel 30 g, chloroform:methanol=200:0–6) to afford 0.56 g of the intermediate compound (67).

(NMR Data for the Intermediate Compound (67))

¹H-NMR (CDCl₃) δ ppm: 8.31 (1H, d, J=8.3 Hz), 7.52 (1H, d, J=9.3 Hz), 7.44 (1H, d, J=4.9 Hz), 7.24–7.38 (6H, m), 7.21 (1H, d, J=5.4 Hz), 7.14 (4H, dd, J=2.9, 8.8 Hz), 7.00 (1H, d, J=7.8 Hz), 6.82 (4H, dd, J=2.4, 8.8 Hz), 6.67 (1H, d, J=7.8 Hz), 6.17 (1H, d, J=8.3 Hz), 5.33–5.40 (1H, m), 5.13–5.18 (1H, m), 5.10 (2H, s), 4.37–4.55 (3H, m), 3.93–4.01 (2H, m), 3.95 (1H, t, J=5.4 Hz), 3.77 (6H, s), 3.49 (2H, t, J=4.4 Hz), 3.28–3.40 (3H, m), 3.09 (1H, dd, J=3.7, 16 Hz), 2.72 (2H, d, J=6.8 Hz), 2.66 (1H, dd, J=10, 16 Hz), 2.42–2.52 (1H, m), 2.31–2.40 (1H, m), 2.00–2.10 (1H, m), 1.89–1.98 (2H, m), 1.37 (9H, s), 1.34–1.88 (13H, m), 1.12–1.33 (14H, m), 0.80–1.01 (33H, m)

SYNTHESIS EXAMPLE 109

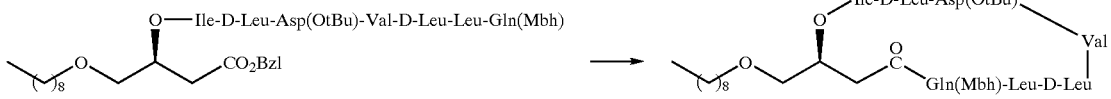

To a solution of the intermediate compound (67) (0.46 g) obtained in Synthesis Example 108 in methanol (20 ml) was added 5% palladium carbon (0.05 g) and the mixture was stirred under hydrogen atmosphere for 3 hours. The palladium carbon was filtered off, the methanol was removed in vacuo and the residue was purified by a silica gel column chromatography (silica gel 20 g, chloroform:methanol= 200:) 0–10) to afford 0.25 g of an intermediate compound. The intermediate compound thus obtained was dissolved in THF (43 ml) and N-methylmorpholine (0.04 ml) and HOBt-.monohydrate (0.12 g) were added to form Solution A. To a mixed solvent of THF (87 ml) and DMF (43 ml) were added in turn cesium chloride (0.32 g), potassium chloride (0.13 g) and WSCI (0.33 g) to form Solution B. Solution A was added dropwise to Solution B at room temperature over one hour while stirring and the mixture was further stirred at room temperature for 7 days. The reaction solution was diluted with ethyl acetate (50 ml) and the mixture was washed in turn with water, 5% aqueous sodium hydrogencarbonate, water, 10% aqueous citric acid and water and then dried over anhydrous sodium sulfate. After the solvent was removed in vacuo, the residue was purified by a silica gel column chromatography (silica gel 20 g, chloroform:methanol=200:) 0–3) to afford 0.18 g of the cyclic depsipeptide (21) of the invention.

(NMR Data for the Cyclic Depsipeptide (21))

¹H-NMR (CDCl₃) δ ppm: 7.69 (1H, d, J=8.8 Hz), 7.37 (1H, d, J=7.8 Hz), 7.16 (4H, dd, J=8.8, 13 Hz), 7.07–7.13 (2H, m), 7.03 (1H, d, J=8.8 Hz), 7.01 (1H, d, J=8.3 Hz), 6.90 (1H, d, 7.8 Hz), 6.86 (4H, dd, J=2.0, 8.3 Hz), 6.63 (1H, br s), 6.22 (1H, d, J=8.3 Hz), 5.08–5.17 (2H, m), 4.36–4.49 (3H, m), 4.19 (1H, dd, J=4.4, 7.3 Hz), 4.11 (1H, dt, J=32.9, 7.6 Hz), 3.86 (1H, dd, J=4.9, 6.3 Hz), 3.79 (6H, 2s), 3.75–3.84 (2H, m), 3.53 (1H, dd, J=4.2,11 Hz), 3.35–3.46 (2H, m), 3.15 (1H, dd, J=4.4, 16 Hz), 2.67 (1H, dd, J=5.4, 15 Hz), 2.49 (1H, dd, J=10, 16 Hz), 2.45 (1H, dd, J=5.1, 15 Hz), 2.27–2.36 (1H, m), 2.17–2.26 (1H, m), 1.99–2.10 (1H, m), 1.47–1.99 (15H, m), 1.41 (9H, s), 1.09–1.44 (12H, m), 0.82–1.00 (33H, m)

SYNTHESIS EXAMPLE 110

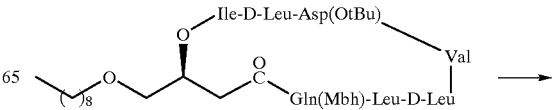

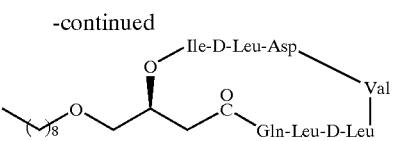

A solution of the cyclic depsipeptide (21) (0.12 g) obtained in Synthesis Example 109 in TFA (3 ml) was stirred at room temperature for 3 hours. After the solvent was removed in vacuo, the residue was neutralized with 5% aqueous sodium hydrogencarbonate and extracted with a 10% methanolic solution of chloroform. The organic layer was dried over anhydrous sodium sulfate and concentrated, and then purified by a silica gel column chromatography (silica gel 5 g, chloroform:methanol 50:0–15) and furthermore solidified using diethyl ether-hexane to afford 0.04 g of the cyclic depsipeptide (22) of the invention.

(NMR Data for the Cyclic Depsipeptide (22))

$^1$H-NMR (DMSO-d6) δ ppm: 9.75 (1H, br s), 9.40 (1H, br s), 8.42–8.50 (1H, m), 8.23 (1H, d, J=8.8 Hz), 7.99 (1H, d, J=8.8 Hz), 7.46–7.61 (1H, m), 7.15 (2H, br s), 6.61 (1H, br s), 5.07 (1H, br s), 4.20–4.45 (5H, m), 4.15 (1H, t, J=8.3 Hz), 4.06 (1H, t, J=7.3 Hz), 3.49–3.57 (2H, m), 3.29–3.44 (2H, m), 2.63–2.73 (2H, m), 2.42 (1H, dd, J=7.3, 14 Hz), 1.90–2.31 (5H, m), 1.73–1.87 (2H, m), 1.33–1.62 (12H, m), 1.17–1.32 (13H, m), 1.06–1.16 (1H, m), 0.73–0.90 (33H, m)

SYNTHESIS EXAMPLE 111

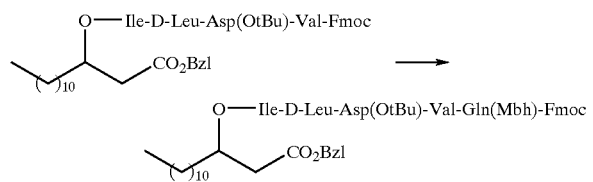

To a solution of the intermediate compound (5) (1.30 g) obtained in Synthesis Example 6 in dimethyl-formamide (13 ml) was added diethylamine (1.3 ml) and the mixture was stirred at room temperature for 2 hours. After the solvent was removed in vacuo, N-α-9-Fmoc-N-γ-Mbh-L-glutamine (0.81 g) and 1-hydroxybenzotriazole-monohydrate (0.21 g) were added and the mixture was dissolved in dichloromethane (30 ml). To this solution was added under ice-cooling 1-ethyl-3-(3-dimethylaminopropyl)carbodiimide-hydrochloride (0.26 g). This solution was stirred under ice-cooling for 2 hours and then allowed to gradually rise up to room temperature and stirred overnight. After the dichloromethane was removed in vacuo, to the residue were added chloroform and 10% aqueous citric acid. The separated chloroform layer was washed in turn with water, 5% aqueous sodium hydrogencarbonate and water and then dried over anhydrous sodium sulfate. After the chloroform was removed in vacuo, the residue was purified by a silica gel column chromatography (silica gel 25 g, chloroform:methanol=200:0–4) and furthermore solidified using ethyl acetate and hexane to afford 1.53 g of the intermediate compound (68).

(NMR Data for the Intermediate Compound (68))

$^1$H-NMR (DMSO-d6) δ ppm: 8.50 (1H, d, J=9.3 Hz), 8.21 (1H, d, J=7.8 Hz), 7.94 (1H, d, J=7.8 Hz), 7.85 (2H, d, J=7.3 Hz), 7.59–7.76 (4H, m), 7.48 (1H, d, J=8.3 Hz), 7.39 (2H, t, J=7.6 Hz), 7.27–7.36 (7H, m), 7.14 (4H, dd, J=2.0, 8.8 Hz), 6.83 (4H, dd, J=2.7, 8.8 Hz), 6.02 (1H, d, J=8.3 Hz), 5.08–5.16 (1H, m), 5.07–5.06 (2H, s), 4.57–4.65 (1H, m), 4.46–4.44 (1H, m), 4.15–4.31 (5H, m), 4.04–4.12 (1H, m), 3.71 (6H, 2s), 2.58–2.71 (3H, m), 2.40–2.55 (1H, m), 2.22–2.34 (2H, m), 1.90–2.00 (2H, m), 1.72–1.85 (2H, m), 1.40–1.60 (5H, m), 1.32 (9H, s), 1.10–1.37 (20H, m), 0.74–0.89 (21H, m)

SYNTHESIS EXAMPLE 112

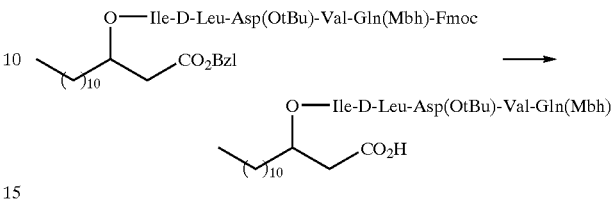

To a solution of the intermediate compound (68) (1.53 g) obtained in Synthesis Example 111 in DMF (20 ml) was added diethylamine (2 ml) and the mixture was stirred at room temperature for 2 hours. After the solvent was removed in vacuo, to a solution of the amine derivative thus obtained in methanol (50 ml) was added 5% palladium carbon (0.15 g) and the mixture was stirred under hydrogen atmosphere for 3 hours. The palladium carbon was filtered off and the methanol was removed in vacuo, the residue was purified by a silica gel column chromatography (silica gel 30 g, chloroform:methanol=200:0–30) to afford 0.77 g of the intermediate compound (69).

(NMR Data for the Intermediate Compound (69))

$^1$H-NMR (CD$_3$OD) δ ppm: 7.22 (2H, d, J=8.3 Hz), 7.14 (2H, d, J=8.8 Hz), 6.88 (2H, d, J=8.8 Hz), 6.85 (2H, d, J=38.8 Hz), 6.04 (1H, s), 5.19–5.27 (1H, m), 4.59–4.65 (2H, m), 4.30 (1H, d, J=4.9 Hz), 4.00–4.06 (1H, m), 3.87 (1H, d, J=37.3 Hz), 3.79 (3H, s), 3.77 (3H, s), 2.87 (1H, dd, J=4.4, 17 Hz), 2.61 (1H, dd, J=8.8, 17 Hz), 2.34–2.52 (3H, m), 2.17–2.34 (3H, m), 1.92–2.07 (2H, m), 1.42 (9H, s), 1.39–1.64 (5H, m), 1.20–1.35 (20H, m), 0.85–1.04 (21H, m)

SYNTHESIS EXAMPLE 113

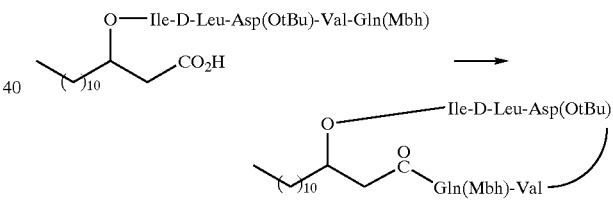

To a solution of the intermediate compound (69) (0.50 g) obtained in Synthesis Example 112 in THF (110 ml) were added N-methylmorpholine (0.10 ml) and HOBt.monohydrate (0.28 g) to form Solution A. To a mixed solvent of THF (220 ml) and DMF (110 ml) were added in turn cesium chloride (0.77 g), potassium chloride (0.31 g) and WSCI (0.79 g) to form Solution B. Solution A was added dropwise to Solution B at room temperature over 20 minutes while stirring and the mixture was further stirred at room temperature for 5 days. The reaction solution was diluted with ethyl acetate (100 ml) and the mixture was washed in turn with water, 5% aqueous sodium hydrogencarbonate, water, 10% aqueous citric-acid and water and then dried over anhydrous sodium sulfate. After the solvent was removed in vacuo, the residue was purified by a silica gel column chromatography (silica gel 30 g, chloroform:methanol= 200:0–6) to afford 0.49 g of the cyclic depsipeptide (23) of the invention.

(NMR Data for the Cyclic Depsipeptide (23))

$^1$H-NMR (CD$_3$OD) δ ppm: 7.11–7.22 (4H, m), 6.81–6.90 (4H, m), 6.09 (1H, s), 5.17–5.30 (1H, m), 4.52–4.59 (1H, m), 4.26–4.50 (2H, m), 4.11–4.17 (1H, m), 3.89–4.03 (1H, m), 3.79 (6H, 2s), 3.00–3.09 (1H, m), 2.69–2.78 (1H, m), 2.29–2.57 (4H, m), 1.84–2.22 (4H, m), 1.39–1.77 (5H, m), 1.44 (9H, s), 1.11–1.39 (20H, m), 0.84–1.01 (21H, m)

SYNTHESIS EXAMPLE 114

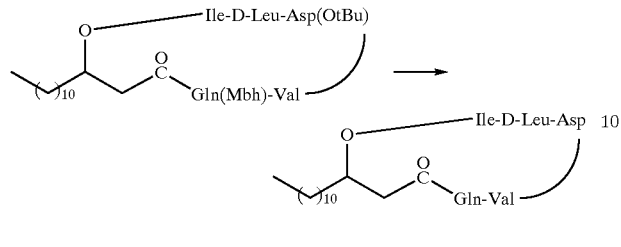

A solution of the cyclic depsipeptide (23) (0.49 g) obtained in Synthesis Example 113 in TFA (5 ml) was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and concentrated and then purified by a silica gel column chromatography (silica gel 20 g, chloroform:methanol=100:0–40) to afford 0.28 g of the cyclic depsipeptide (24) of the invention.

(NMR Data for the Cyclic Depsipeptide (24))

$^1$H-NMR (CD$_3$OD) δ ppm: 5.25–5.34 (1H, m), 4.62 (1H, t, J=5.4 Hz), 4.47 (1H, t, J=7.1 Hz), 4.34 (1H, dd, J=4.6, 8.8 Hz), 4.23 (1H, d, J=8.3 Hz), 4.02 (1H, d, J=5.9 Hz), 2.76 (2H, d, J=5.4 Hz), 2.62 (1H, dd, J=3.4, 16 Hz), 2.55 (1H, dd, J=7.3, 15 Hz), 2.38 (1H, dd, J=6.8, 8.3 Hz), 2.35 (1H, d, J=5.9 Hz), 2.14–2.31 (2H, m), 1.89–2.10 (2H, m), 1.59–1.78 (4H, m), 1.47–1.56 (1H, m), 1.16–1.41 (20H, m), 0.83–1.06 (21H, m)

SYNTHESIS EXAMPLE 115

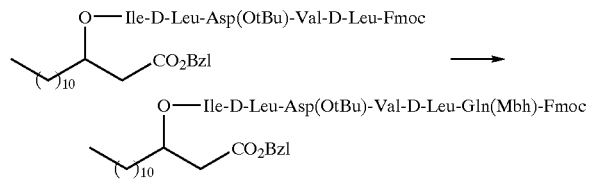

To a solution of the intermediate compound (6) (0.80 g) obtained in Synthesis Example 7 in dimethyl-formamide (8 ml) was added diethylamine (0.8 ml) and the mixture was stirred at room temperature for 4 hours. After the solvent was removed in vacuo, N-α-9-Fmoc-N-γ-Mbh-L-glutamine (0.45 g) and 1-hydroxybenzotriazole.monohydrate (0.12 g) were added and the mixture was dissolved in dichloromethane (15 ml). To this solution was added under ice-cooling WSCI (0.14 g). This solution was stirred under ice-cooling for 2 hours and then allowed to gradually rise up to room temperature and stirred overnight. After removal of the dichloromethane, to the residue were added chloroform and 10% aqueous citric acid. The separated chloroform layer was washed in turn with water, 5% aqueous sodium hydrogencarbonate and water and then dried over anhydrous sodium sulfate. After the chloroform was removed in vacuo, the residue was purified by a silica gel column chromatography (silica gel 30 g, chloroform:methanol=200:0–4) and furthermore solidified using diethyl ether and hexane to afford 1.04 g of the intermediate compound (70).

(NMR Data for the Intermediate Compound (70))

$^1$H-NMR (CD$_3$OD) δ ppm: 7.74–7.78 (2H, m), 7.56–7.69 (2H, m), 7.22–7.42 (9H, m), 7.10–7.17 (4H, m), 6.80–6.86 (4H, m), 6.11 (1H, s), 5.18–5.31 (1H, m), 4.96–5.08 (2H, m), 4.13–4.56 (7H, m), 4.01–4.13 (1H, m), 3.88–3.95 (1H, m), 3.75 (6H, s), 2.37–2.74 (6H, m), 1.96–2.17 (3H, m), 1.50–1.96 (10H, m), 1.10–1.50 (28H, m), 0.76–0.99 (27H, m)

SYNTHESIS EXAMPLE 116

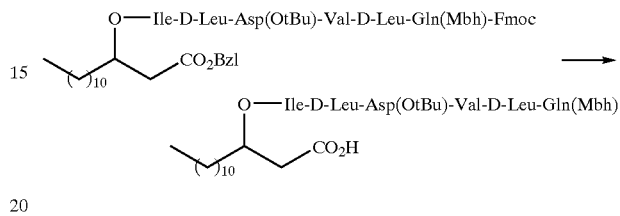

To a solution of the intermediate compound (70) (0.97 g) obtained in Synthesis Example 115 in DMF (10 ml) was added diethylamine (1 ml) and the mixture was stirred at room temperature for 1.5 hours. After the solvent was removed in vacuo, the residue was dissolved in methanol (40 ml), 5% palladium carbon (0.10 g) was added and the mixture was stirred under hydrogen atmosphere for 3 hours. The palladium carbon was filtered off and the methanol was removed in vacuo, and then the residue was purified by a silica gel column chromatography (silica gel 18 g, chloroform:methanol=200:0–20) and furthermore solidified with ethyl acetate-hexane to afford 0.53 g of the intermediate compound (71).

(NMR Data for the Intermediate Compound (71))

$^1$H-NMR (CD$_3$OD) δ ppm: 7.15 (4H, dd, J=4.9, 8.3 Hz), 6.86 (4H, dd, J=3.4, 8.8 Hz), 6.09 (1H, s), 5.21–5.40 (1H, m), 4.37–4.49 (2H, m), 4.19 (1H, d, J=7.3 Hz), 4.15–4.26 (1H, m), 4.04 (1H, d, J=5.9 Hz), 3.91–4.00 (1H, m), 3.77 (6H, s), 2.86–3.02 (1H, m), 2.70–2.80 (1H, m), 2.47–2.60 (2H, m), 2.32–2.44 (2H, m), 1.82–2.01 (1H, m), 1.49–1.82 (8H, m), 1.44 (9H, 2s), 1.14–1.49 (22H, m), 0.80–1.07 (27H, m)

SYNTHESIS EXAMPLE 117

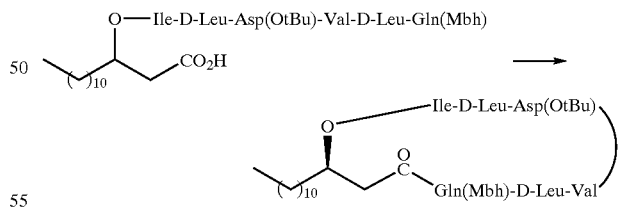

To a solution of the intermediate compound (71) (0.50 g) obtained in Synthesis Example 116 in THF (95 ml) were added N-methylmorpholine (0.09 ml) and HOBt.monohydrate (0.25 g) to form Solution A. To a mixed solvent of THF (190 ml) and DMF (95 ml) were added in turn cesium chloride (0.70 g), potassium chloride (0.28 g) and WSCI (0.71 g) to form Solution B. Solution A was added dropwise to Solution B at room temperature over 20 minutes while stirring and the mixture was further stirred at room temperature for 5 days. The reaction solution was diluted with ethyl acetate (100 ml) and the mixture was washed in turn with water, 5% aqueous sodium hydrogencarbonate, water, 10% aqueous citric acid and water and then dried over anhydrous sodium sulfate. After the solvent was removed in vacuo, the residue was purified by a silica gel column chromatography (silica gel 30 g, chloroform:methanol= 200:0–6) to afford 0.44 g of the cyclic depsipeptide (25) of the invention.

(NMR Data for the Cyclic Depsipeptide (25))

$^1$H-NMR (CD$_3$OD) δ ppm: 7.10–7.17 (4H, m), 6.81–6.89 (4H, m), 6.08 (1H, s), 5.07–5.23 (1H, m), 4.35–4.54 (3H, m), 4.23–4.32 (2H, m), 3.89–3.94 (1H, m), 3.78 (3H, s), 3.77 (3H, s), 2.71–3.04 (3H, m), 2.35–2.53 (4H, m), 2.13–2.45 (1H, m), 1.92–2.08 (2H, m), 1.50–1.81 (9H, m), 1.44 (9H, s), 1.21–1.50 (19H, m), 0.83–1.02 (27H, m)

SYNTHESIS EXAMPLE 118

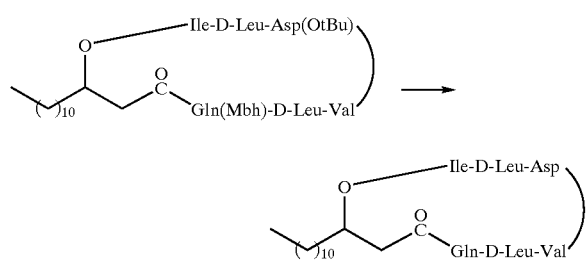

A solution of the cyclic depsipeptide (25) (0.40 g) obtained in Synthesis Example 117 in TFA (5 ml) was stirred at room temperature for 2 hours. After the solvent was removed in vacuo, the residue was neutralized with 5% aqueous sodium hydrogencarbonate and extracted with a 10% methanolic solution of chloroform. The organic layer was dried over anhydrous sodium sulfate and concentrated and then purified by a silica gel column chromatography (silica gel 20 g, chloroform:methanol=100:0–50) and furthermore solidified with diethyl ether-hexane to afford 0.25 g of the cyclic depsipeptide (26) of the invention.

(NMR Data for the Cyclic Depsipeptide (26))

$^1$H-NMR (CD$_3$OD) δ ppm: 5.08 (1H, s), 4.37–4.64 (5H, m), 3.94–3.98 (1H, m), 2.36–3.16 (3H, m), 2.16–2.36 (4H, m), 1.86–2.06 (3H, m), 1.47–1.80 (7H, m), 1.15–1.44 (21H, m), 0.83–1.08 (27H, m)

SYNTHESIS EXAMPLE 119

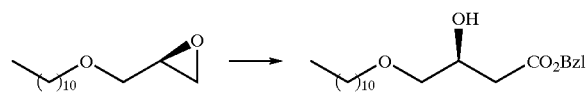

The desired alcohol (0.86 g) was obtained from (R)-(+)-1,2-epoxy-3-undecyloxypropane (2.71 g) in the same manner as described in Synthesis Example 105.

$^1$H-NMR (CDCl$_3$) δ ppm: 7.28–7.41 (5H, m), 5.16 (2H, s), 4.18–4.26 (1H, m), 3.35–3.49 (4H, m), 2.87 (1H, br s), 2.58 (2H, d, J=6.3 Hz), 1.56 (2H, qui., J=6.8 Hz), 1.20–1.35 (16H, m), 0.88 (3H, t, J=6.8 Hz)

SYNTHESIS EXAMPLE 120

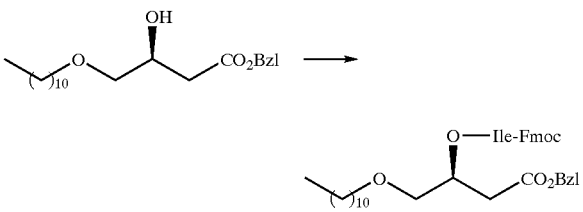

The desired intermediate compound (1.50 g) was obtained starting from the alcohol (0.84 g) obtained in Synthesis Example 119 In the same manner as described in Synthesis Example 106.

$^1$H-NMR (CDCl$_3$) δ ppm: 7.76 (2H, d, J=7.3 Hz), 7.60 (2H, d, J=5.9 Hz), 7.40 (2H, t, J=7.3 Hz), 7.27–7.37 (7H, m), 5.39–5.49 (1H, m), 5.32 (1H, d, J=8.8 Hz), 5.12 (2H, s), 4.36–4.41 (2H, m), 4.32 (1H, dd, J=4.6, 8.8 Hz), 4.23 (1H, t, J=6.8 Hz), 3.55 (1H, dd, J=5.1, 11 Hz), 3.49 (1H, dd, J=4.4, 10 Hz), 3.31–3.45 (2H, m), 2.74 (2H, d, J=6.8 Hz), 1.88 (1H, br s), 1.36–1.56 (2H, m), 1.06–1.34 (18H, m), 0.88 (3H, t, J=6.8 Hz), 0.85–0.94 (6H, m)

SYNTHESIS EXAMPLE 121

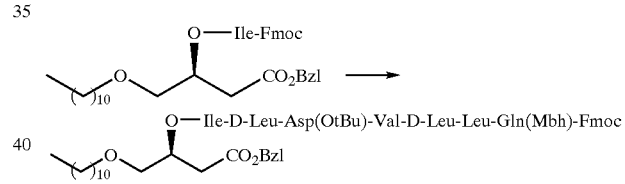

The desired chain depsipeptide (0.77 g) was obtained from the intermediate compound (0.35 g) obtained in Synthesis Example 120 in the same manner as described in Synthesis Example 107.

However, instead of the tripeptide (6), there was used the hexapeptide (0.64 g) which was obtained by debenzylating the hexapeptide (1) obtained in Synthesis Example 49 in the same manner as described in Synthesis Example 17.

$^1$H-NMR (CDCl$_3$) δ ppm: 8.48 (1H, d, J=8.8 Hz), 7.72 (2H, d, J=7.3 Hz), 7.64–7.78 (1H, m), 7.51–7.62 (2H, m), 7.41 (1H, d, J=8.3 Hz), 7.36 (2H, t, J=7.3 Hz), 7.20 (2H, d, J=8.8 Hz), 7.16 (2H, d, J=8.3 Hz), 7.13–7.45 (8H, m), 7.10 (1H, d, J=8.8 Hz), 7.00 (1H, d, J=8.3 Hz), 6.93 (1H, d, J=5.4 Hz), 6.85 (4H, d, J=8.8 Hz), 6.61 (1H, d, J=7.8 Hz), 6.25 (1H, d, J=8.3 Hz), 5.29–5.41 (1H, m), 4.99–5.17 (3H, m), 4.27–4.64 (5H, m), 4.10–4.24 (2H, m), 3.91–4.04 (2H, m), 3.77 (3H, s), 3.76 (3H, s), 3.25–3.57 (4H, m), 3.14 (1H, dd, J=3.4, 15 Hz), 2.62–2.78 (3H, m), 2.44–2.55 (1H, m), 2.30–2.41 (1H, m), 2.14 (1H, br s), 1.42 (9H, S), 1.07–2.08 (32H, m), 0.65–1.05 (33H, m)

SYNTHESIS EXAMPLE 122

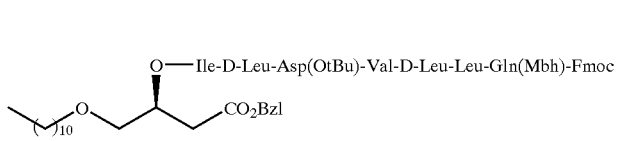

The desired cyclic depsipeptide (27) (0.30 g) was obtained from the chain depsipeptide (0.39 g) obtained in Synthesis Example 121 in the same manner as described in Synthesis Example 52 (3).

(Data for the Cyclic Depsipeptide (27))

$^1$H-NMR (CDCl$_3$) δ ppm: 7.71 (1H, d, J=8.8 Hz), 7.36 (1H, d, J=8.3 Hz), 7.17 (1H, d, J=8.8 Hz), 7.14 (2H, d, J=8.8 Hz), 7.07–7.21 (2H, m), 6.98–7.07 (2H, m), 6.91 (1H, d, J=8.3 Hz), 6.85 (4H, dd, J=1.5, 8.3 Hz), 6.70 (1H, br s), 6.21 (1H, d, J=8.3 Hz), 5.07–5.17 (2H, m), 4.34–4.49 (3H, m), 4.20 (1H, dd, J=4.4, 7.8 Hz), 4.08–4.16 (1H, m), 3.87 (1H, t, J=5.4 Hz), 3.79 (6H, 2s), 3.75–3.84 (2H, m), 3.53 (1H, dd, J=3.9, 10 Hz), 3.36–3.51 (2H, m), 3.14 (1H, dd, J=4.9, 16 Hz), 2.68 (1H, dd, J=5.4, 15 Hz), 2.38–2.53 (2H, m), 2.16–2.37 (2H, m), 1.47–2.15 (16H, m), 1.40 (9H, s), 1.09–1.46 (16H, m), 0.78–1.04 (33H, m)

SYNTHESIS EXAMPLE 123

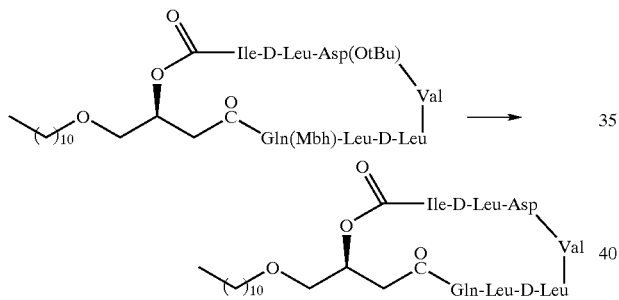

The desired cyclic depsipeptide (28) (0.16 g) was obtained from the cyclic despipeptide (27) (0.28 g) obtained in Synthesis Example 122 in the same manner as described in Synthesis Example 12.

(Data for the Cyclic Depsipeptide (28))

$^1$H-NMR (DMSO-d$_6$+TFA) δ ppm: 8.40 (1H, d, J=8.3 Hz), 8.31 (1H, d, J=6.3 Hz), 8.16 (1H, d, J=7.3 Hz), 7.99 (1H, d, J=5.9 Hz), 7.96 (1H, d, J=7.3 Hz), 7.84 (1H, d, J=8.3 Hz), 7.79 (1H, d, J=8.3 Hz), 7.31 (1H, s), 6.85 (1H, s), 5.07–5.16 (1H, m), 4.44–4.59 (2H, m), 4.12–4.29 (4H, m), 4.07 (1H, t, J=7.6 Hz), 3.48–3.55 (1H, m), 3.26–3.46 (3H, m), 2.58–2.72 (2H, m), 2.35–2.46 (2H, m), 1.95–2.16 (3H, m), 1.68–1.94 (3H, m), 1.32–1.65 (11H, m), 1.11–1.31 (18H, m), 0.71–0.96 (33H, m)

SYNTHESIS EXAMPLE 124

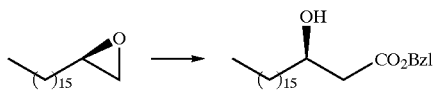

The desired alcohol (0.47 g) was obtained from (R)-1,2-epoxyoctadecane (3.00 g) in the same manner as described in Synthesis Example 105.

$^1$H-NMR (CDCl$_3$) δ ppm: 7.29–7.42 (5H, m), 5.16 (2H, s), 3.97–4.07 (1H, m), 2.84 (1H, br s), 2.56 (1H, dd, J=3.2, 16 Hz), 2.46 (1H, dd, J=9.0, 17 Hz), 1.37–1.67 (4H, m), 1.06–1.36 (26H, m), 0.88 (3H, t, J=6.8 Hz)

SYNTHESIS EXAMPLE 125

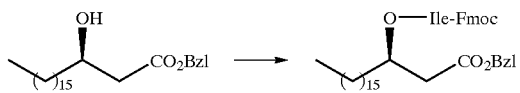

The desired intermediate compound (0.82 g) was obtained from the alcohol (0.45 g) obtained in Synthesis Example 124 in the same manner as described in Synthesis Example 106.

(Data for the Above Intermediate Compound)

$^1$H-NMR (CDCl$_3$) δ ppm: 7.76 (2H, d, J=7.8 Hz), 7.59 (2H, d, J=5.9 Hz), 7.39 (2H, t, J=7.6 Hz), 7.26–7.36 (7H, m), 5.22–5.36 (2H, m), 5.10 (2H, s), 4.34–4.42 (2H, m), 4.31 (1H, dd, J=4.4, 8.8 Hz), 4.22 (1H, t, J=7.1 Hz), 2.69 (1H, dd, J=6.8, 16 Hz), 2.59 (1H, dd, J=5.6, 15 Hz), 1.89 (1H, br s), 1.61 (2H, br s), 1.05–1.48 (30H, m), 0.85–1.00 (6H, m), 0.88 (3H, t, J=6.6 Hz)

SYNTHESIS EXAMPLE 126

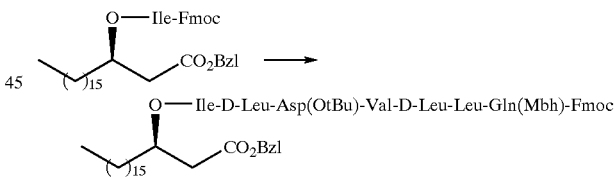

The desired chain depsipeptide (0.69 g) was obtained from the intermediate compound (0.40 g) obtained in Synthesis Example 125 in the same manner as described in Synthesis Example 121.

$^1$H-NMR (CDCl$_3$) δ ppm: 8.48 (1H, d, J=8.8 Hz), 7.73 (2H, d, J=7.3 Hz), 7.69 (1H, d, J=8.8 Hz), 7.55 (2H, dd, J=3.2, 6.8 Hz), 7.42 (1H, d, J=8.3 Hz), 7.37 (2H, t, J=7.3 Hz), 7.20 (2H, d, J=8.3 Hz), 7.17 (2H, d, J=8.3 Hz), 7.15–7.45 (8H, m), 7.04–7.13 (1H, m), 7.01 (1H, d, J=8.3 Hz), 6.93 (1H, d, J=5.9 Hz), 6.85 (4H, d, J=8.3 Hz), 6.54 (1H, d, J=7.8 Hz), 6.25 (1H, d, J=8.3 Hz), 4.98–5.23 (4H, m), 4.27–4.69 (5H, m), 4.10–4.24 (2H, m), 3.92–4.04 (2H, m), 3.77 (3H, s), 3.76 (3H, s), 3.13 (1H, dd, J=3.4, 15 Hz), 2.62–2.76 (2H, m), 2.43–2.58 (2H, m), 2.31–2.41 (1H, m), 2.14 (1H, br s), 1.68–2.08 (5H, m), 1.42 (9H, S), 1.05–1.67 (39H, m), 0.75–1.04 (33H, m)

SYNTHESIS EXAMPLE 127

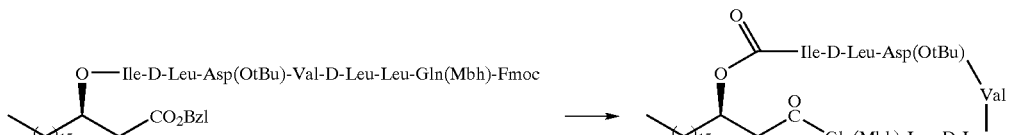

The desired cyclic depsipeptide (27) (0.28 g) was obtained from the chain depsipeptide (0.32 g) obtained in Synthesis Example 126 in the same manner as described in Synthesis Example 122.

(Data for the Cyclic Depsipeptide (27))

$^1$H-NMR (CDCl$_3$) δ ppm: 7.64 (1H, d, J=8.3 Hz), 7.31 (1H, d, J=7.3 Hz), 7.17 (1H, d, J=8.8 Hz), 7.14 (2H, d, J=8.8 Hz), 7.07–7.19 (2H, m), 7.01 (1H, d, J=9.3 Hz), 6.96 (1H, d, J=8.8 Hz), 6.90 (1H, d, J=7.3 Hz), 6.85 (4H, d, J=7.8 Hz), 6.78 (1H, br s), 6.20 (1H, d, J=8.3 Hz), 5.05–5.15 (1H, m), 4.95–5.04 (1H, m), 4.29–4.49 (3H, m), 4.18 (1H, dd, J=4.4, 12 Hz), 4.09–4.21 (1H, m), 3.87 (1H, t, J=5.4 Hz), 3.79 (6H, 2s), 3.15 (1H, dd, J=4.4, 17 Hz), 2.63 (1H, dd, J=4.4, 16 Hz), 2.51 (1H, dd, J=9.8, 17 Hz), 2.30–2.40 (2H, m), 2.19–2.28 (1H, m), 1.54–2.13 (15H, m), 1.40 (9H, s), 1.04–1.48 (30H, m), 0.77–1.02 (33H, m)

SYNTHESIS EXAMPLE 128

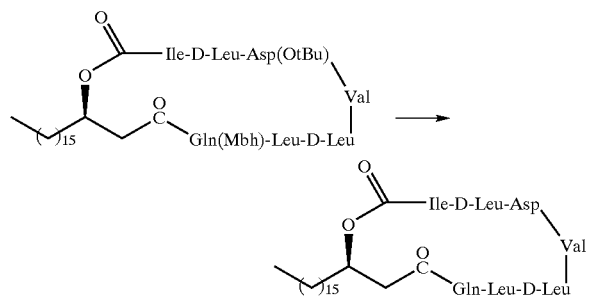

The desired cyclic depsipeptide (28) (0.14 g) was obtained from the cyclic depsipeptide (27) (0.27 g) obtained in Synthesis Example 127 in the same manner as described in Synthesis Example 123.

(Data for the Cyclic Depsipeptide (28))

$^1$H-NMR (DMSO-d$_6$) δ ppm: 12.30 (1H, br s), 8.38 (1H, d, J=6.8 Hz), 8.30 (1H, d, J=7.8 Hz), 8.11 (1H, d, J=7.3 Hz), 7.86 (1H, d, J=8.8 Hz), 7.81–7.96 (3H, m), 7.30 (1H, s), 6.86 (1H, s), 4.91–5.00 (1H, m), 4.45–4.61 (2H, m), 4.12–4.27 (4H, m), 4.08 (1H, t, J=7.3 Hz), 2.65 (2H, d, J=6.3 Hz), 2.27–2.44 (2H, m), 1.96–2.14 (3H, m), 1.67–1.93 (3H, m), 1.08–1.64 (41H, m), 0.68–0.92 (33H, m)

EXAMPLE 1

It will be explained below that the cyclic depsipeptides of the invention show a promoting activity on the production of apolipoprotein E in Hep G2 cells, together with the test procedures used.

The compounds used in the following Examples are as defined below:

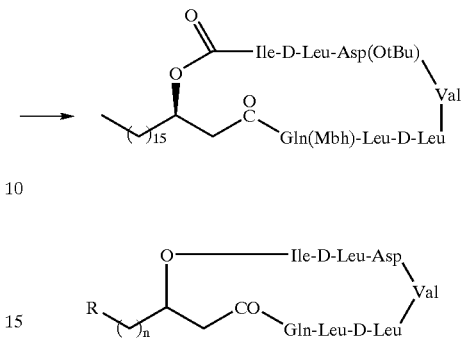

R=isopropyl, n=7 Compound 1
R=isopropyl, n=8 Compound 2
R=isopropyl, n=9 Compound 3

The above Compounds 1, 2 and 3 were obtained according to the process for the production of the Compounds 3, 1 and 4 disclosed in WO 95/32990, respectively; that is to say, by culturing Bacillus sp. No. 4691 strain (FERM BP-5101) capable of producing the Compounds 1–3 of the present invention and extracting and purifying the said cyclic depsipeptides from the cultured broth.

First, 1 ml portions of Hep G2 cells at 1×10$^5$ cells/ml suspended in Dulbecco's modified Eagle medium (manufactured by Nissui Seiyaku Co., Ltd.; hereinafter referred to as "D-MEM medium") containing 10% fetal bovine serum were poured into a 24-well tissue culture plate and cultivation was carried out at 37° C. under atmosphere of a mixed gas composed of 5% carbon dioxide and 95% air. After 3 days, the medium was removed by means of a pipette, 1 ml of fresh D-MEM medium was added and further 10 μl of a methanolic solution of the cyclic depsipeptide of the invention, or Compound 1, 2 or 3, at the concentration as shown in Table 2 was added. After 18 hours, the medium was again replaced (D-MEM medium), 10 μl of a methanolic solution of the cyclic depsipeptide was added and then cultivation was continued at 37° C. for 8 hours to obtain the cultured broths 1–6. The apolipoprotein E produced in the cultured broths 1–6 was assayed by means of an enzyme immunoassay method.

The composition of the buffers used in the enzyme immunoassay is summarized in the following Table 1, wherein PBS represents phosphate-buffered saline, PBS-T represents phosphate-buffered saline having incorporated Tween 20 and the blocking solution is the phosphate buffer containing the immunosuppressive agent derived from lactoprotein "Block Ace", manufactured by Dainippon Pharmaceutical Co., Ltd.

TABLE 1

| | | |
|---|---|---|
| PBS (pH 7.2) | KH$_2$PO$_4$ | 0.2 g |
| | Na$_2$HPO$_4$.12H$_2$O | 2.9 g |
| | NaCl | 8.0 g |
| | KCl | 0.2 g |
| | Distilled water | q.s. |
| | Total amount | 1000 ml |
| PBS-T (pH 7.2) | KH$_2$PO$_4$ | 0.2 g |
| | Na$_2$HPO$_4$.12H$_2$O | 2.9 g |
| | NaCl | 8.0 g |
| | KCl | 0.2 g |
| | Tween 20 | 0.5 g |

TABLE 1-continued

| | | |
|---|---|---|
| | Distilled water | q.s. |
| | Total amount | 1000 ml |
| Blocking soln. (pH 7.2) | Block Ace | 250 ml |
| | $KH_2PO_4$ | 0.2 g |
| | $Na_2HPO_4.12H_2O$ | 2.9 g |
| | NaCl | 8.0 g |
| | KCl | 0.2 g |
| | Distilled water | q.s. |
| | Total amount | 1000 ml |

The mouse antihuman apolipoprotein E monoclonal antibody (manufactured by BYOSIS, S. A., France) was dissolved in a 0.05M aqueous sodium hydrogencarbonate solution (pH 9.5) at a concentration of 5 µl/ml. 50 µl of this solution was poured in portions into a Nunk immunoplate, which was then allowed to stand at 4° C. for 16 hours. After washing thrice with 300 µl of PBS, 300 µl of the blocking solution was added and the mixture was allowed to stand at 37° C. for 2 hours.

It was again washed three times with 300 µl of PBS, 50 µl of the above cultured broth 1 was added and the mixture was allowed to stand at room temperature for 2 hours. After washing three times with 300 µl of PBS-T, 50 µl of a 3000-fold diluted solution (10% aqueous Block Ace solution) of goat anti-apolipoprotein E polyclonal antibody (manufactured by Chemicon Co., Ltd., U.S.A.) was added and the mixture was allowed to stand at room temperature for 2 hours. The mixture was washed three times with 300 µl of PBS-T, a 5000-fold diluted solution (a 10% aqueous solution of Block Ace) of a peroxidase-labeled anti-goat IgG polyclonal antibody (manufactured by Bindingsite Co., Ltd., U.K.) was added and the mixture was allowed to stand at room temperature for 2 hours. After washing five times with 300 µl of PBS-T, 100 µl of a coloring solution (Composition: 0.1M potassium citrate (pH 4.5) 1 ml, 30% aqueous hydrogen peroxide 0.4 µl, orthophenylenediamine 1 mg) was added and the mixture was allowed to stand as such for 2 minutes. The reaction was discontinued by the addition of 100 µl of 2N sulfuric acid, and absorbance at 490 nm was measured using absorbance at 650 nm as a control. An absolute amount of apolipoprotein E in cultured broths 1–6 was determined upon a calibration curve drawn up when a commercially available apolipoprotein E (Chemicon Co., Ltd., U.S.A.) was used as a standard.

The same procedure as described in Example 1 was carried out except that methanol was added instead of the methanolic solution of the cyclic depsipeptide to measure an apolipoprotein E amount, which was used as a control.

A relative apolipoprotein E amount of each sample was represented in terms of a relative value (t) when the control was defined as 100.

As shown in Table 2, it was proved that Compounds 1–3 of the invention have a potent activity of promoting the production of apolipoprotein E at 1 or 5 µM.

TABLE 2

| Compound | Conc. (µM) | Relative amount of apolipoprotein E (%) |
|---|---|---|
| 1 | 1 | 207 |
| | 5 | 256 |
| 2 | 1 | 110 |
| | 5 | 243 |

TABLE 2-continued

| Compound | Conc. (µM) | Relative amount of apolipoprotein E (%) |
|---|---|---|
| 3 | 1 | 147 |
| | 5 | 278 |
| Control | 0 | 100 |

As is seen from the above results, the cyclic depsipeptide of the invention highly promotes the production of apolipoprotein E in Hep G2 cells and thus it is useful as a novel type of a therapeutic agent for neurologic damages or an antidementia agent.

EXAMPLE 2

It will be explained below that the cyclic depsipeptides of the invention represented by the above formula (1') show a promoting activity on the production of apolipoprotein E, an inhibitory activity on the production of apolipoprotein B and a promoting activity on the production of apolipoprotein A1 in Hep G2 cells, together with the test procedures used.

First, 1 ml portions of Hep G2 cells at $1 \times 10^5$ cells/ml suspended in D-MEM medium containing 10% fetal bovine serum were poured into a 24-well tissue culture plate and cultivation was carried out at 37° C. under atmosphere of a mixed gas composed of 5% carbon dioxide and 95% air for 3 days. Thereafter, the medium was removed by means of a pipette, 1 ml of fresh D-MEM medium was added and cultivation was again carried out at 37° C. under atmosphere of a mixed gas composed of 5% carbon dioxide and 95% air for one day. Then, the medium was removed by means of a pipette and washed three times with 0.5 ml of fresh D-MEM medium. 1 ml of fresh D-MEM medium was added and further 10 µl of a solution of the cyclic depsipeptide of the invention or Compound 1, 4, 5, 6, 7 or 8 dissolved in methanol at the concentration as shown in Table 3 was added. Cultivation was further continued at 37° C. for 7 hours to obtain Cultured Broths 7–10. The apolipoprotein E, apolipoprotein B and apolipoprotein Al produced in Cultured Broths 7–10 were assayed. Assay for apolipoprotein E was carried out by using the same procedure as described in Example 1. Assay for apolipoprotein B and apolipoprotein A1 will be as described below.

1) Assay for Apolipoprotein B

The sheep antihuman apolipoprotein B IgG fraction (manufactured by Bindingsite Co., Ltd., U.K.) was dissolved in a 0.05M aqueous sodium hydrogencarbonate solution (pH 9.5) at a concentration of 10 µg/ml. 50 µl of this solution was poured in portions into a Nunk immunoplate, which was then allowed to stand at 4° C. for 16 hours. After washing three times with 300 µl of PBS, 300 µl of the blocking solution was added and the mixture was allowed to stand at 37° C. for 2 hours. It was again washed three times with 300 µl of PBS, 50 µl of the culture solution (the above Cultured Broths 7–10 diluted with 10% Block Ace to 3.3 times volumes, respectively) was added and the mixture was allowed to stand at room temperature for 2 hours. After washing three times with 300 µl of PBS-T, 50 µl of a 0.5% solution of sheep antihuman apolipoprotein B peroxidase labeled preparation (manufactured by Bindingsite Co., Ltd., U.K.) (10% aqueous "Block Ace" solution) was added and the mixture was allowed to stand at room temperature for 2 hours. After washing five times with 300 µl of PBS-T, 100 µl of a coloring solution (Composition: 0.1M potassium citrate (pH 4.5) 1 ml, 30% aqueous hydrogen peroxide 0.4 µl, orthophenylene-diamine 1 mg) was added and the mixture was allowed to stand as such for 2 minutes. The reaction was discontinued by the addition of 100 µl of 2N sulfuric acid, and absorbance at 490 nm was measured using absorbance at 650 nm as a control. The absorbance obtained was defined as that of apolipoprotein B. An absolute amount of apolipoprotein B was determined upon a calibration curve drawn up when a commercially available low density lipoprotein (manufactured by Sigma, U.S.A.) was used as a standard.

The same procedure as described in Example 1 was carried out except that methanol was added instead of the methanolic solution of the cyclic depsipeptide to measure an apolipoprotein B amount, which was used as a control.

A relative apolipoprotein B amount of the present cyclic depsipeptides was represented in terms of a relative value (%) when the control was defined as 100.

2) Assay for Apolipoprotein A1

The mouse antihuman apolipoprotein A1 monoclonal antibody (manufactured by Medix Biotec, U.S.A.) was dissolved in a 0.05M aqueous sodium hydrogencarbonate solution (pH 9.5) at a concentration of 10 µg/ml. 50 µl of this solution was poured in portions into a Nunk immunoplate, which was then allowed to stand at 4° C. for 16 hours. After washing three times with 300 µl of PBS, 300 µl of the blocking solution was added and the mixture was allowed to stand at 37° C. for 2 hours and then at 4° C. for 16 hours.

It was again washed three times with 300 µl of PBS, 100 µl of the above Cultured Broths 7–10 was added and the mixture was allowed to stand at room temperature for 2 hours. After washing three times with 300 µl of PBS-T, 50 µl of a 2000-fold diluted solution of sheep anti-apolipoprotein A1 peroxidase labeled preparation (manufactured by Bindingsite Co., Ltd., U.K.) (10% aqueous "Block Ace" solution) was added and the mixture was allowed to stand at room temperature for 1.5 hours. After washing three times with 300 µl of PBS-T, 100 µl of a coloring solution (Composition: 0.1M potassium citrate (pH 4.5) 1 ml, 30% aqueous hydrogen peroxide 0.4 µl, ortho-phenylenediamine 1 mg) was added and the mixture was allowed to stand as such for 2 minutes. The reaction was discontinued by the addition of 100 µl of 2N sulfuric acid, and absorbance at 490 nm was measured using absorbance at 650 nm as a control. An absolute amount of apolipoprotein A1 was determined upon a calibration curve drawn up when a commercially available apolipoprotein Al (manufactured by Sigma, U.S.A.) was used as a standard.

The same procedure as described in Example 2 was carried out except that methanol was added instead of the methanolic solution of the cyclic depsipeptide to measure an apolipoprotein Al amount, which was used as a control.

A relative apolipoprotein Al amount of the present cyclic depsipeptides was represented in terms of a relative value (%) when the control was defined as 100.

As shown in Table 3, it was proved that the cyclic depsipeptides of the invention have a potent activity of promoting the production of apolipoprotein E at 1 or 5 µM. Also, it was proved that Compounds 3–7 highly promote the production of apolipoprotein A1 and also have a potent inhibitory activity on the production of apolipoprotein B.

TABLE 3

|  | Conc. ($\mu$M) | Relative amount of apolipoprotein E (%) | Relative amount of apolipoprotein B (%) | Relative amount of apolipoprotein A1 (%) |
|---|---|---|---|---|
| Compound 4 | 1 | 457 | 43 | 147 |
| Compound 4 | 5 | 1042 | 25 | 161 |
| Compound 3 | 1 | 359 | 64 | 124 |
| Compound 3 | 5 | 851 | 21 | 146 |
| Compound 5 | 1 | 132 | 91 | 123 |
| Compound 6 | 1 | 198 | 72 | 142 |
| Compound 7 | 1 | 163 | 76 | 135 |
| Compound 8 | 1 | 423 | 71 | 96 |
| Control | 0 | 100 | 100 | 100 |

As is seen from the above results, the cyclic depsipeptide of the invention represented by the above formula (1) markedly promotes the production of apolipoprotein E or apolipoprotein A1 in Hep G2 cells at a low concentration and markedly inhibits the production of apolipoprotein B, and thus it is useful as a therapeutic agent for hyperlipemia.

PREPARATION EXAMPLES

Preparation Example 1 Tablets (per Tablet)

| Compound 4 | 20 mg |
|---|---|
| Magnesium silicate | 20 mg |
| Lactose | 98.5 mg |
| Hydroxypropylcellulose | 7.5 mg |
| Magnesium stearate | 1 mg |
| Hydrogenated vegetable oil | 3 mg |
| Total | 150 mg |

Compound 4, magnesium silicate and lactose were admixed and kneaded with an alcoholic solution of hydroxypropylcellulose and then granulated to appropriate particle size, dried, and sized. Then, magnesium stearate and hydrogenated vegetable oil were added and blended to form uniform granules. The granules were then prepared to tablets, each having a diameter of 7.0 mm, a weight of 150 mg and a hardness of 6 kg, by means of a rotary tableting machine.

Preparation Example 2 Granules

| Compound 4 | 10 mg |
|---|---|
| Magnesium oxide | 40 mg |
| Calcium hydrogenphosphate | 38 mg |
| Lactose | 10 mg |
| Hydroxypropylcellulose | 20 mg |

All the materials except for hydroxypropyl-cellulose were uniformly admixed, kneaded with an alcoholic solution of hydroxypropylcellulose and then granulated by means of an extrusion granulation machine and dried to form granules. The granules were sized so as to pass through a 12 mesh sieve and remain on a 48 mesh sieve, thereby forming granules.

Preparation Example 3 Syrups

| | |
|---|---|
| Compound 4 | 1.000 g |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavoring agent | 0.200 g |
| Glycerol | 0.150 g |
| 96% Ethanol | 0.500 g |
| Purified water | q.s. |
| Total | 100 ml |

Sucrose, D-sorbitol, ethyl paraoxybenzoate, propyl paraoxybenzoate and Compound 4 were dissolved in 60 g of purified water (warm water). After cooling, a solution of flavoring agent in glycerol and ethanol was added and then to the mixture was added purified water to make up a volume to 100 ml.

Preparation Example 4 Injections

| | |
|---|---|
| Sodium salt of Compound 4 | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and sodium salt of Compound 4 were dissolved in distilled water to make up a total amount to 10.0 ml.

Preparation Example 5 Suppositories

| | |
|---|---|
| Compound 4 | 2 g |
| Macrogol 4000 | 20 g |
| Glycerol | 78 g |
| Total | 100 g |

Compound 4 was dissolved in glycerol and then macrogol 4000 was added and dissolved by warming. Then, the mixture was injected into a suppository die and solidified by cooling to prepare suppositories, each weighing 1.5 g.

Industrial Applicability

The cyclic depsipeptides of the present invention have a promoting activity on the production of apolipoprotein E, an inhibitory activity on the production of apolipoprotein B and a promoting activity on the production of apolipoprotein A1. Since apolipoprotein E has a repairing action on neurologic damages, the cyclic depsipeptides of the invention having an activity of promoting the production of apolipoprotein E are useful as a therapeutic agent for neurologic damages, especially an antidementia agent. Moreover, since apolipoprotein B is a main apolipoprotein of a low density lipoprotein cholesterol (LDL cholesterol) known as a "bad" cholesterol and apolipoprotein A1 is a main apolipoprotein of a high density lipoprotein cholesterol (HDL cholesterol) known as a "good" cholesterol, the cyclic depsipeptides of the invention having an action of inhibiting the production of apolipoprotein B and an action of promoting the production of apolipoprotein A1 are useful as a therapeutic agent for hyperlipemia.

What is claimed is:

1. A method for promoting production of apolipoprotein E, which comprises administering to a patient in need thereof one or more cyclic depsipeptide of the formula (1) as an active ingredient:

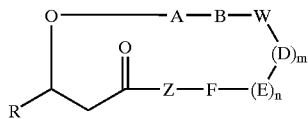
(1)

wherein:
R is a straight or branched alkyl group of 5 to 20 carbon atoms, or a straight or branched alkoxymethyl group of 5–15 carbon atoms; A, B, D, E and F are each independently a residue of an amino acid selected from the group consisting of alanine, valine, leucine, isoleucine, serine, threonine, lysine, hydroxylysine, arginine, cysteine, methionine, phenylalanine, tyrosine, tryptophan, histidine, proline, 4-hydroxyproline, piperizine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperizylalanine, 3-(2-naphthyl)alanine, βcyclohexylalanine, β-t-butylalanine, 9-anthracenylalanine, α-methylalanine, 2-aminobutanoic acid, and an N—(C$_1$–C$_4$) alkyl derivative of any of the above foregoing amino acid residues; W and Z are independently a residue of an amino acid selected from the group consisting of aspartic acid, asparagine, glutamic acid and glutamine; and m and n are independently 0 or 1, wherein any free amino group, any free carboxyl group or any free ω-carbamido group of said amino acid residue in A, B, D, E, F, W and Z is optionally protected by a protecting group used in peptide chemistry. further wherein when said amino acid residue in A, B, D, E, F, W and Z is a residue of lysine, hydroxylysine, glutamic acid or aspartic acid, the amino group or carboxyl group capable of being bound to an adjacent amino acid by peptide linkage is optionally located at either the α-position or the ω-position, or a pharmacologically acceptable salt thereof.

2. The method as claimed in claim 1, which comprises administering as an active ingredient one or more cyclic depsipeptides of the formula (1) wherein A is isoleucine or alanine; B is leucine, alanine, β-t-butylalanine, valine or phenylalanine; D is valine or alanine; E is leucine, alanine, β-t-butylalanine, valine or phenylalanine; F is leucine, alanine, β-t-butylalanine, valine or phenylalanine; W is aspartic acid or glutamic acid; and Z is glutamine or asparagine; m and n are 0 or 1; and R is a straight alkyl group or alkoxymethyl group of 6 to 12 carbon atoms, or a pharmaceutically acceptable salt thereof.

3. The method as claimed in claim 1, which comprises administering as an active ingredient one or more cyclic depsipeptides of the formula (1) wherein A is isoleucine or alanine; B is D-leucine, D-alanine, D-β-t-butylalanine, D valine or D-phenylalanine; E is D-leucine, D-alanine, D-β-t butylalanine, D-valine or D-phenylalanine; F is leucine, alanine, β-butylalanine, valine or phenylalanine; W is aspartic acid or glutamic acid; and Z is glutamine or asparagine; m and n are 0 or 1; and R is a straight alkyl group or alkoxymethyl group of 6 to 12 carbon atoms, or a pharmaceutically acceptable salt thereof.

4. The method as claimed in claim 1, wherein said one or more cyclic depsipeptides of the formula (1) have any of the following formulae:

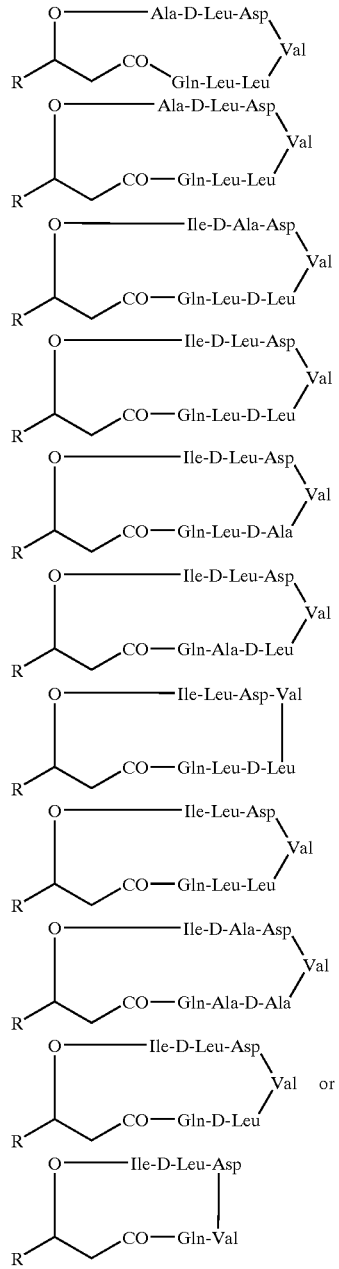

wherein R is as defined above.

5. The method as claimed in claim 1, wherein said one or more cyclic depsipeptides of the formula (1) have the formula:

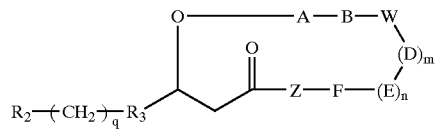

wherein, $R_2$ is methyl or isopropyl; $R_3$ is a direct bond or —OCH$_2$—; and q is an integer of 2–10.

6. A cyclic depsipeptide of the formula (1'):

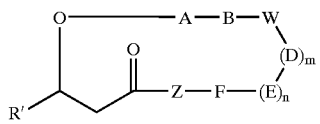

wherein:
R is a straight or branched alkyl group of 5–20 carbon atoms, or a straight or branched alkoxymethyl group of 5–15 carbon atoms; A, B, D, E and F are each independently a residue of an amino acid selected from the group consisting of alanine, valine, leucine, isoleucine, serine, threonine, lysine, hydroxylysine, arginine, cysteine, methionine, phenylalanine, tyrosine, tryptophan, histidine, proline, 4-hydroxyproline, piperizine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperizylalanine, 3-(2-naphthyl)alanine,β-cyclohexylalanine, β-t-butylalanine, 9-anthracenylalanine, α-methylalanine, 2-aminobutanoic acid, and an N—($C_1$–$C_4$) alkyl derivative of any of the foregoing amino acid residues; W and Z are independently a residue of an amino acid selected from the group consisting of aspartic acid, asparagine, glutamic acid and glutamine; and m and n are independently 0 or 1, wherein any free amino group, any free carboxyl group or any free ω-carbamido group of said amino acid residue in A, B, D, E, F, W, and Z is optionally protected by a protecting group used in peptide chemistry, further wherein when said amino acid residue in A, B, D, E, F, W and Z is a residue of lysine, hydroxylysine, glutamic acid or aspartic acid, the amino group or carboxyl group capable of being bound to an adjacent amino acid by peptide linkage is optionally located at either the α-position or the ω-position, provided that there are excluded the cases wherein m and n are 1, A is isoleucine, B is leucine, W is aspartic acid, D is valine, E is leucine, F is leucine, Z is glutamic acid or glutamine and R' is a group of the formula $R_1$–$(CH_2)_p$— wherein $R_1$ is methyl, isopropyl, sec-butyl or isobutyl and p is an integer of 5–15, or a pharmacologically acceptable salt thereof.

7. The cyclic depsipeptide as claimed in claim 6, wherein A is isoleucine or alanine, B is leucine, alanine, β-t-butylalanine, valine or phenylalanine, D is valine or alanine, E is leucine, alanine, β-t-butylalanine, valine or phenylalanine, F is leucine, alanine, β-t-butylalanine, valine or phenylalanine, W is aspartic acid or glutamic acid, and Z is glutamine or asparagine, m and n are 1, and R' is a straight alkyl group or alkoxymethyl group of 6–12 carbon atoms, or a pharmaceutically acceptable salt thereof.

8. The cyclic depsipeptide as claimed in claim 6, wherein A is isoleucine or alanine, B is D-leucine, D alanine, D-β-t-butylalanine, D-valine or D-phenylalanine, E is D-leucine, D-alanine, D-β-t-butylalanine, D-valine or D phenylalanine, F is leucine, alanine, β-t-butylalanine, valine or phenylalanine, W is asparatic acid or glutamic acid, and Z is glutamine or asparagine, m and n are 1, and R' is a straight alkyl group or alkoxymethyl group of 6–12 carbon atoms, or a pharmaceutically acceptable salt thereof.

9. The cyclic depsipeptide as claimed in claim 6 having any of the following formulae:

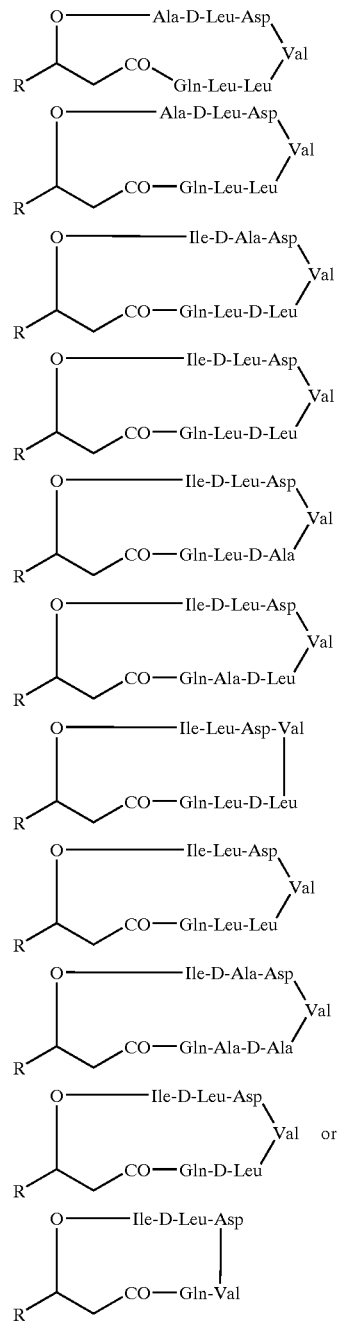

10. The cyclic depsipeptide as claimed in claim 6 having the formula:

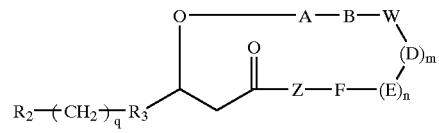

wherein, $R_2$ is methyl or isopropyl; $R_3$ is a direct bond or —$OCH_2$—; and q is an integer of 2–10.

11. A pharmaceutical composition which comprises a cyclic depsipeptide of the formula (1')

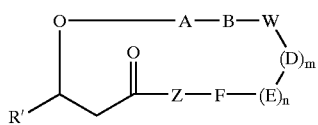

(1')

wherein:

R' is a straight of branched alkyl group of 5 to 20 carbon atoms, or a straight or branched alkoxymethyl group of 5 to 15 carbon atoms; A, B, D, E and F are each independently a residue of an amino acid selected from the group consisting of alanine, valine, leucine, isoleucine, serine, threonine, lysine, hydroxylysine, arginine, cysteine, methionine, phenylalanine, tyrosine, tryptophan, histidine, proline, 4-hydroxyproline, piperizine-4-carboxylic acid, homoproline, octahydroindole-2-carboxylic acid, norvaline, norleucine, β-t-butylglycine, cyclohexylglycine, azetidine-2-carboxylic acid, 3-(3-pyridyl)alanine, (3-N-methyl)piperizylalanine, 3-(2-naphthyl)alanine, β-cyclohexylalanine, β-t-butylalanine, 9-anthracenylalanine, β-methylalanine and 2-aminobutanoic acid or an N—($C_1$–$C_4$)alkyl derivative of said amino acid residue; W and Z are independently a residue of an amino acid selected from the group consisting of aspartic acid, asparagine, glutamic acid and glutamine; and m and n are independently 0 or 1; and wherein a free amino group, a free carboxyl group or a free ω-carbamido group of said amino acid residue may be protected by a protecting group commonly used in peptide chemistry and, when said amino acid residue in the above A, B, D, E, F, W and Z is a residue of lysine, hydroxylysine, glutamic acid or aspartic acid, the amino group or carboxyl group capable of being bound to an adjacent amino acid by peptide linkage may be located at either the α-position or the ω-position; provided that there are excluded the cases wherein m and n are 1, A is isoleucine, B is leucine, W is aspartic acid, D is valine, E is leucine, F is leucine, Z is glutamic acid or glutamine and R' is a group of the formula $R_1$–$CH_2)_p$— wherein $R_1$ is methyl, isopropyl, sec-butyl or isobutyl and p is an integer of 5–15, or a pharmaceutically acceptable salt thereof, and a pharmaceutically acceptable excipient.

12. A method for inhibiting production of apolipoprotein B, which comprises administering to a patient in need thereof one or more cyclic depsipeptides as claimed in claim 6 or a pharmaceutically acceptable salt thereof.

13. A method for promoting production of apolipoprotein A1, which comprises administering to a patient in need thereof one or more of the cyclic depsipeptides as claimed in claim 6 or a pharmaceutically acceptable salt thereof.

14. A method for treating hyperlipemia, which comprises administering to a patient in need thereof one or more of the cyclic depsipeptides as claimed in claim 6 or a pharmaceutically acceptable salt thereof.

* * * * *

UNITED STATES PATENT AND TRADEMARK OFFICE
CERTIFICATE OF CORRECTION

PATENT NO. : 6,858,585 B1
DATED : February 22, 2005
INVENTOR(S) : Yanai et al.

It is certified that error appears in the above-identified patent and that said Letters Patent is hereby corrected as shown below:

<u>Title page,</u>
Items [45] and [*] Notice, should read as follows:
-- [45] **Date of Patent: *Feb. 22, 2005**

[*] Notice: Subject to any disclaimer, the term of this patent is extended or adjusted under 35 U.S.C. 154(b) by 0 days.

This Patent is subject to a terminal disclaimer. --

Signed and Sealed this

Fourteenth Day of June, 2005

JON W. DUDAS
*Director of the United States Patent and Trademark Office*